(12) United States Patent
Boveja et al.

(10) Patent No.: US 11,206,984 B1
(45) Date of Patent: *Dec. 28, 2021

(54) METHODS AND SYSTEM FOR CARDIAC MAPPING FOR ATRIAL FIBRILLATION USING BALLOON BASED CATHETERS UTILIZING MEDICAL IMAGES (CT OR MRI IN SEGMENTS) AND LEFT VENTRICULAR LEAD PLACEMENT FOR CARDIAC RE-SYNCHRONIZATION THERAPY (CRT)

(71) Applicants: Birinder R. Boveja, Milwaukee, WI (US); Angely Widhany, Greenfield, WI (US)

(72) Inventors: Birinder R. Boveja, Milwaukee, WI (US); Angely Widhany, Greenfield, WI (US)

(73) Assignee: AMERICAN MEDICAL TECHNOLOGIES, LLC, Wauwatosa, WI (US)

( * ) Notice: Subject to any disclaimer, the term of this patent is extended or adjusted under 35 U.S.C. 154(b) by 166 days.

This patent is subject to a terminal disclaimer.

(21) Appl. No.: 16/571,109

(22) Filed: Sep. 14, 2019

Related U.S. Application Data

(63) Continuation-in-part of application No. 15/817,664, filed on Nov. 20, 2017, now Pat. No. 10,413,185.
(Continued)

(51) Int. Cl.
*A61B 5/00* (2006.01)
*A61B 5/01* (2006.01)
(Continued)

(52) U.S. Cl.
CPC .......... *A61B 5/0044* (2013.01); *A61B 5/0082* (2013.01); *A61B 5/015* (2013.01); *A61B 5/361* (2021.01); *A61B 6/481* (2013.01); *A61B 34/20* (2016.02); *G06T 7/0012* (2013.01); *A61B 5/0035* (2013.01); *A61B 5/283* (2021.01); *A61B 6/485* (2013.01); *A61B 8/5261* (2013.01);
(Continued)

(58) Field of Classification Search
CPC combination set(s) only.
See application file for complete search history.

(56) References Cited

U.S. PATENT DOCUMENTS 5,348,554 A 9/1994 Imran et al.
6,052,618 A 4/2000 Dahlke et al.
(Continued)

*Primary Examiner* — George Manuel

(57) ABSTRACT

Methods and system for atrial fibrillation mapping utilizing cardiac mapping based on medical image(s). The methods and system also adapted for any balloon based catheters including cryoballoon catheter, laser balloon catheter, or "hot balloon" catheter, as well as circular catheters. The methods and system includes overlaying of two or more images on top of each other (where the images are of various types or modalities) and aligning the images, where the transparency between the images can be adjusted for navigating and optimal placement of the balloon based catheters or circular catheters. The cardiac system also adopted for guiding optimal placement of the left ventricular (LV) lead placement for cardiac re-synchronization (CRT) therapy, and for mapping and displaying activation times from various branches of the coronary sinus for optimizing CRT therapy.

20 Claims, 51 Drawing Sheets

Related U.S. Application Data which is a continuation-in-part of application No. 15/209,265, filed on Jul. 13, 2016, now Pat. No. 9,820,802, which is a continuation-in-part of application No. 14/709,445, filed on May 11, 2015, now Pat. No. 9,393,071, which is a continuation-in-part of application No. 13/718,284, filed on Dec. 18, 2012, now Pat. No. 9,033,968.

(60) Provisional application No. 61/630,771, filed on Dec. 19, 2011.

(51) Int. Cl.
*G06T 7/00* (2017.01)
*A61B 6/00* (2006.01)
*A61B 34/20* (2016.01)
*A61B 5/361* (2021.01)
*A61B 8/08* (2006.01)
*A61B 18/00* (2006.01)
*A61B 5/283* (2021.01)

(52) U.S. Cl.
CPC .............. *A61B 2018/00577* (2013.01); *A61B 2034/2051* (2016.02)

(56) References Cited

U.S. PATENT DOCUMENTS

| | | |
|---|---|---|
| 7,819,817 B2 | 10/2010 | Rahn |
| 8,224,422 B2 | 7/2012 | Mottola |
| 8,271,095 B2 | 9/2012 | O'Sullivan |
| 8,273,016 B2 | 9/2012 | O'Sullivan |
| 8,303,505 B2 | 11/2012 | Webler et al. |
| 8,355,801 B2 | 1/2013 | O'Sullivan |
| 9,078,567 B2 | 7/2015 | Fuimaono et al. |
| 9,147,289 B2 | 9/2015 | Bourier et al. |
| 9,439,735 B2 | 9/2016 | Guttman et al. |
| 9,468,485 B2 | 10/2016 | Wittenberger et al. |
| 10,402,975 B2 | 9/2019 | Park et al. |
| 2006/0095022 A1* | 5/2006 | Moll ................ A61B 46/10 606/1 |
| 2014/0012155 A1 | 1/2014 | Flaherty et al. |
| 2016/0143522 A1 | 5/2016 | Ransbury et al. |

* cited by examiner

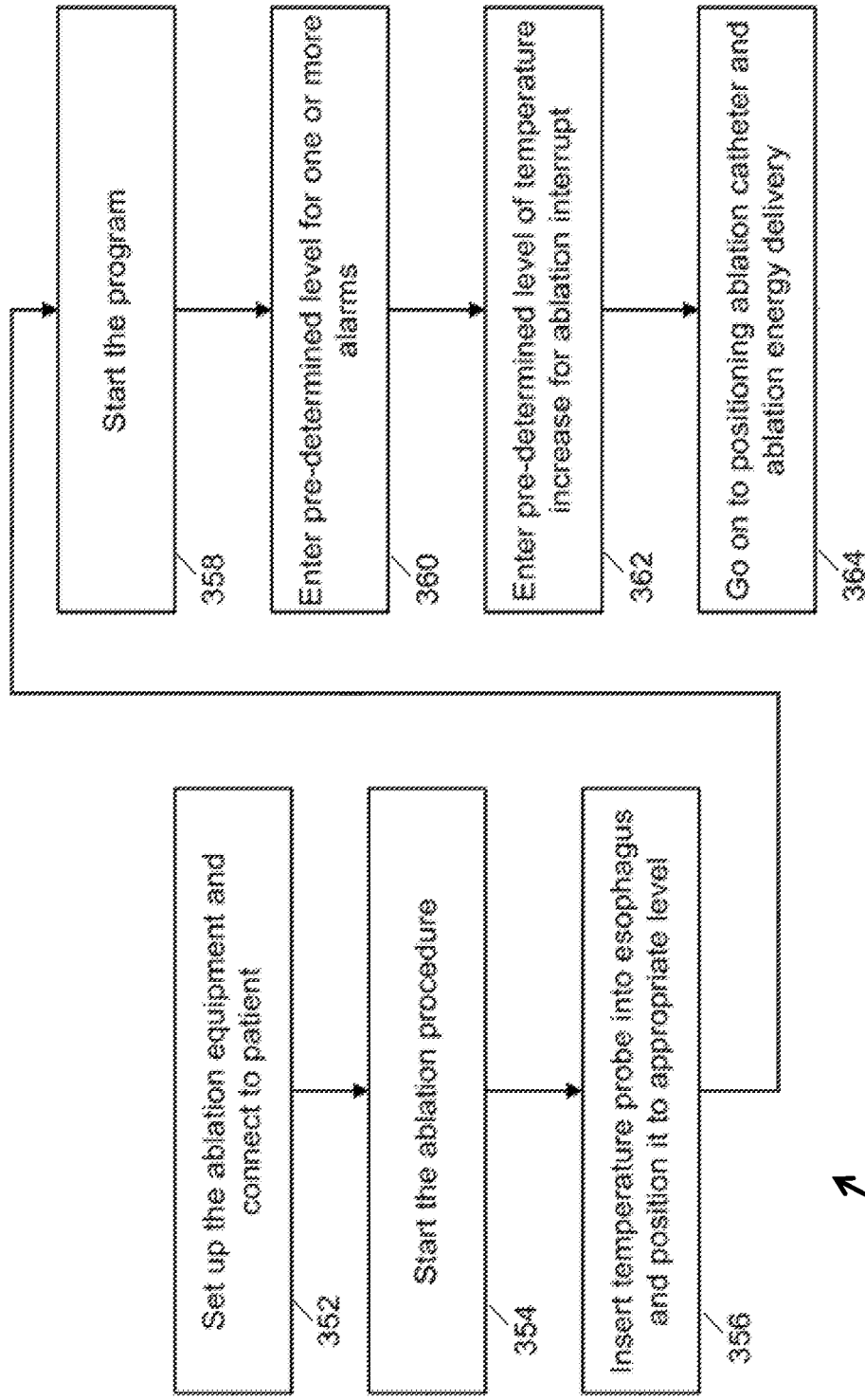

Live and Recorded Images in high resolution

Live and Recorded Images in high resolution 629  2nd Recorded "dye" injection

Recorded "dye" injection  638

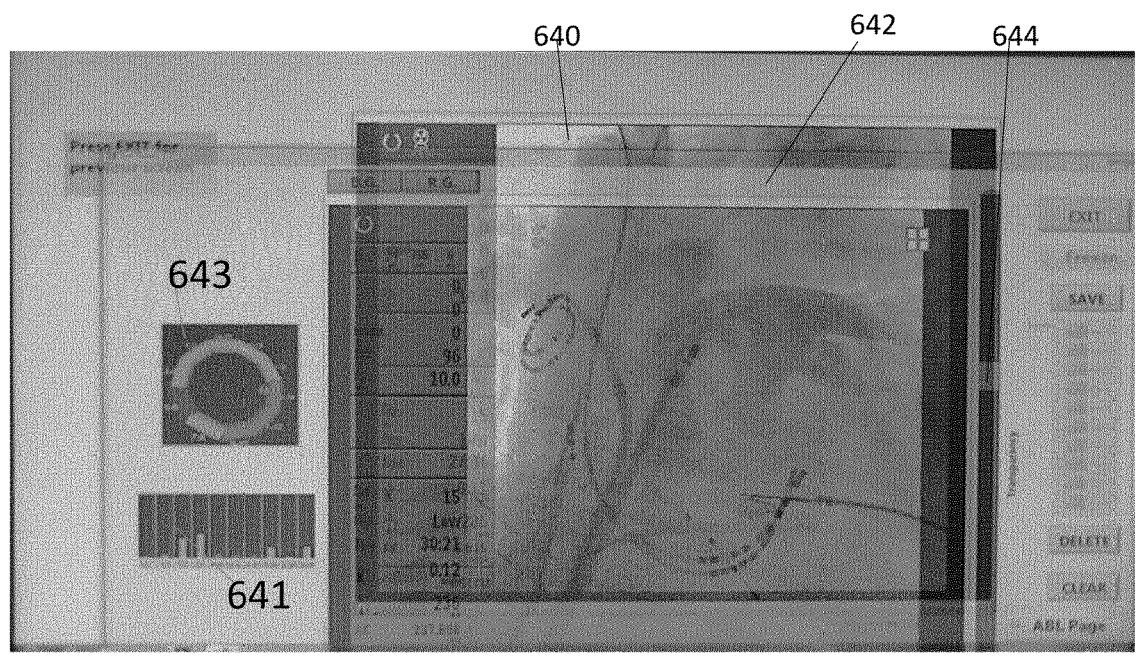
Live fluoroscopy overlaid on recorded dye injection image with signals from circular catheter
FIG 41
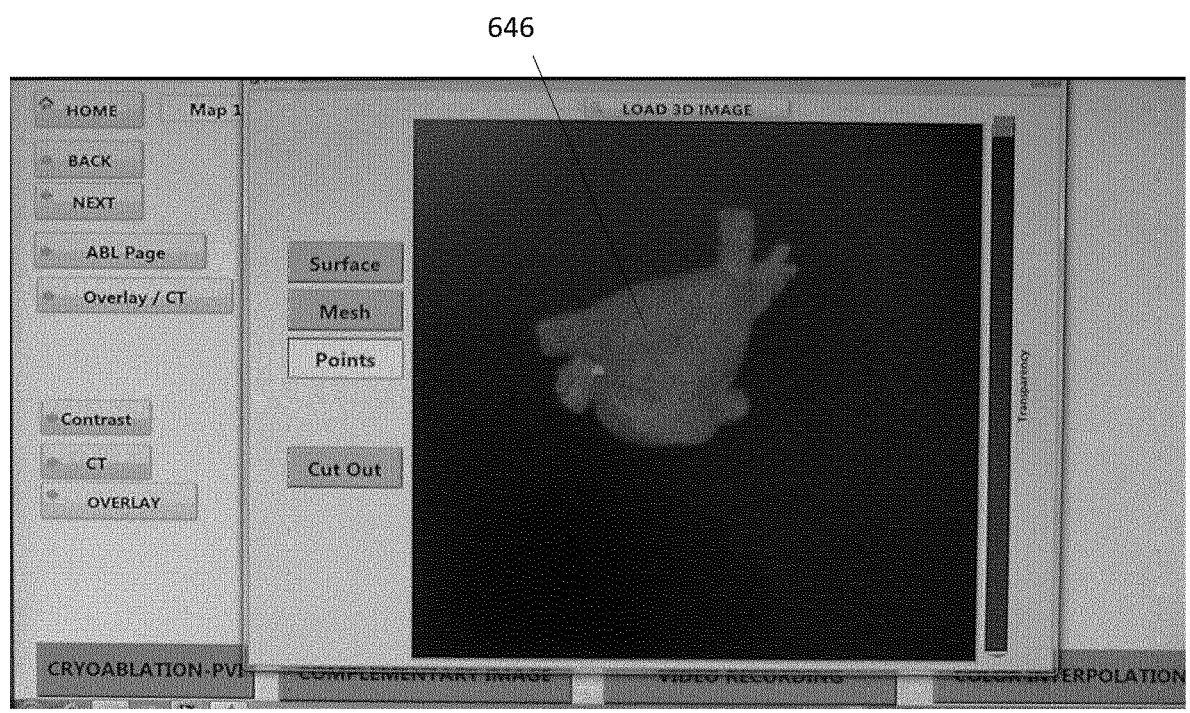
FIG 42　　　　Patient's CT CT overlaid on contrast image CT overlaid on contrast image with live fluoro overlayed and signals from circ. Catheter (contrast + CT+ live fluoro + signals)

Prior Art

Real time flouroscope image with catheters side by side dye injected cardiac venal image used to eye ball insertion of catheters

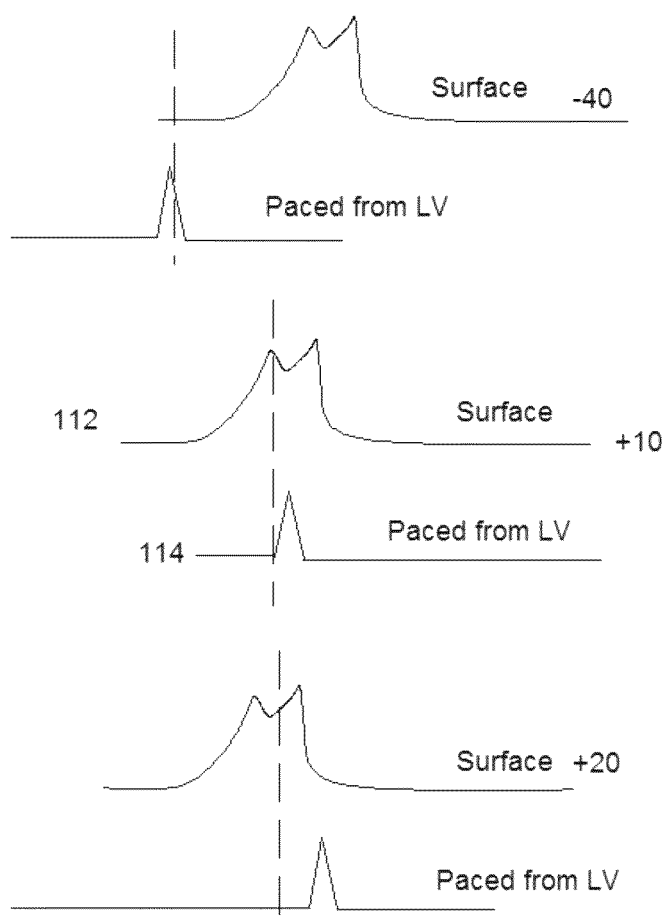
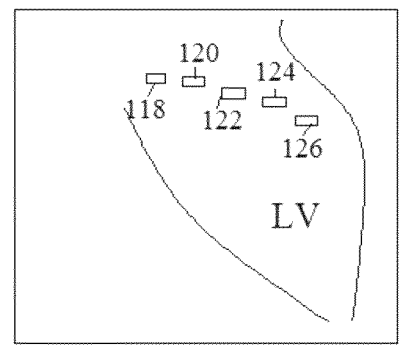
FIG. 63

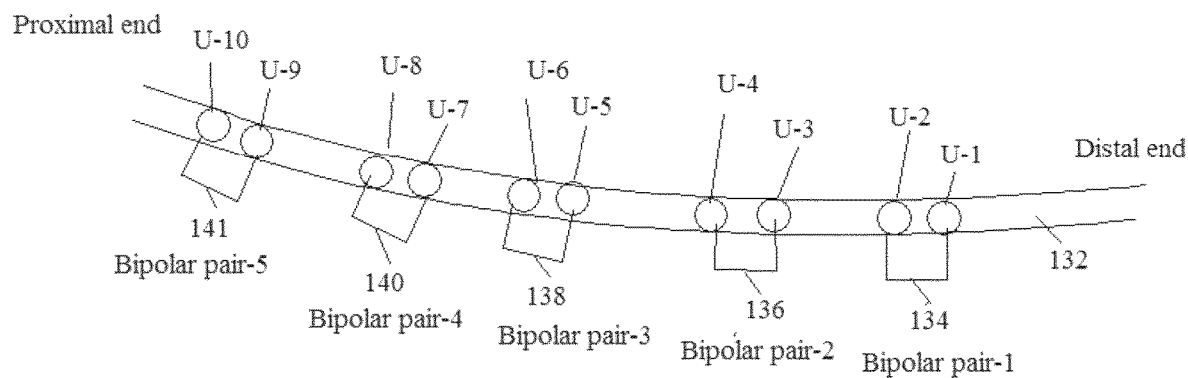
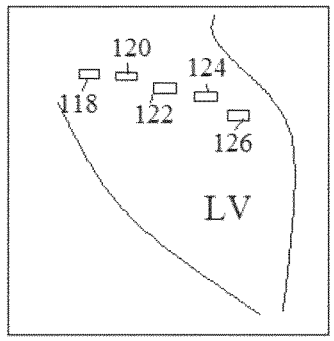
FIG. 64

| Cofigration | Relative time |
|---|---|
| Bipolar pair-5 | -50 |
| Bipolar pair-4 | +10 |
| Bipolar pair-3 | -30 |
| Bipolar pair-2 | -20 |
| Bipolar pair-1 | -10 |
| Unipolar | |
| U -1 | -60 |
| U -2 | +50 |
| U -3 | +70 |
| U -4 | -55 |
| U -5 | -30 |
| U -6 | -15 |
| U -7 | -45 |
| U -8 | -20 |
| U -9 | -25 |
| U -10 | -40 |

Table 144

|     | LAT (mSec) | Volt (mV) | Slew rate |
| --- | --- | --- | --- |
| 1 | -10 | 2.0 | 0.4 |
| 2 | +10 | 2.5 | 0.6 |
| 3 | +50 | 1.5 | 0.8 |
| 4 | +80 | 0.7 | 0.4 |
| 5 | -15 | 0.6 | 0.8 |
| 6 | -89 | 0.5 | 0.6 |
| 7 | -90 | 1.7 | 0.7 |
| 8 | +2 | 2.6 | 1.0 |
| 9 | -10 | 2.5 | 0.9 |
| 10 | -15 | 3.0 | 0.8 |
| 11 | -30 | 1.1 | 0.5 |
| 12 | -40 | 1.2 | 0.7 |
| 13 | +10 | 1.3 | 0.7 |
| 14 | 0 | 0.5 | 0.7 |
| 15 | -16 | 1.5 | 0.8 |
| 16 | -14 | 2.0 | 0.4 |
| 17 | +50 | 2.1 | 1.2 |
| 18 | +60 | 2.2 | 1.1 |
| 19 | +70 | 2.3 | 1.0 |
| 20 | -80 | 0.6 | 0.7 |
| . |  |  |  |
| . |  |  |  |
| . |  |  |  |
| 100 | +50 | 0.25 | 0.7 |

FIG. 66

METHODS AND SYSTEM FOR CARDIAC MAPPING FOR ATRIAL FIBRILLATION USING BALLOON BASED CATHETERS UTILIZING MEDICAL IMAGES (CT OR MRI IN SEGMENTS) AND LEFT VENTRICULAR LEAD PLACEMENT FOR CARDIAC RE-SYNCHRONIZATION THERAPY (CRT)

This application is a Continuation-In-Part (CIP) of U.S. application Ser. No. 15/817,664 filed Nov. 20, 2017, having the projected U.S. Pat. No. 10,413,185 and issue date of Sep. 17, 2019, which is a Continuation-In-Part (CIP) of U.S. application Ser. No. 15/209,265 filed Jul. 13, 2016.

FIELD OF DISCLOSURE

The present disclosure relates to cardiac mapping for atrial fibrillation ablations, more specifically to methods and system of mapping for atrial fibrillation ablations utilizing a balloon based catheter with optional esophageal temperature monitoring, and for guiding left ventricular (LV) lead placement and mapping.

BACKGROUND

General Background of Atrial Fibrillation

Atrial fibrillation (AF) is the most prevalent cardiac arrhythmia. It affects 1% to 2% of the general population with an important increase in incidence with age. In the United States it is estimated that over 5 million people have atrial fibrillation, and because of our aging population the prevalence of this arrhythmia will increase significantly over the next decade.

Atrial fibrillation is associated with increased morbidity and mortality, and in particular, a general decrease in quality of life for those afflicted with atrial fibrillation. AF can also causes tachycardia mediated cardiomyopathy or worsening of pre-existing heart failure. Moreover, AF is known to increase the mortality risk 1.5-2 fold with the risk for stroke increasing five-fold. Patients are at an increased risk of stroke unless they are treated adequately with anticoagulants. Anticoagulant treatment however, increases the patient's risk of bleeding, which carries with it is own set of dangers. Medications currently available for treating atrial fibrillation have proven to be only moderately effective in decreasing the incidence of recurrent atrial fibrillation, and these medications do not decrease the patient's risk of having a stroke.

One method of treating atrial fibrillation has been to perform ablation of selected areas of the left atrium. There is strong evidence to suggest that ablating these areas of the left atrium serves to cure or prevent further incidences of atrial fibrillation, which thereby has shown to reduce the risk of stroke and reduce the necessity of anticoagulant therapy. Typically, ablation of this type is carried out via an intravascular catheter using radiofrequency or microwave energy to cause thermal changes to the selected parts of the left atrial tissue.

Besides having a good safety profile, catheter ablation therapy for AF has proved effective in establishing and maintaining sinus rhythm. Ablation for atrial fibrillation is now the most commonly performed procedure in most laboratories.

It is well known that pulmonary vein isolation (PVI) is an accepted treatment modality for paroxysmal atrial fibrillation. Since pulmonary veins are the dominant initiating source of atrial fibrillation, the source of atrial fibrillation can be abolished by pulmonary vein isolation (PVI). Pulmonary vein isolation (PVI) involves rendering the tissue between pulmonary veins and the left atrium (LA) to be electrically inactive by an ablation procedure, for all the pulmonary veins. There are normally four pulmonary veins (PV), but many times there are variations in the pulmonary vein anatomy. Generally, the aim is to electrically isolate all the pulmonary veins (i.e. create bidirectional block) such that any triggers arising in the pulmonary veins are not conducted to the left atrium (LA).

Frequently these ablation procedures are performed using balloon based catheters. There are various types of balloon based catheters such as laser balloons, cryoballoons and other types of balloon based catheters for arial fibrillation ablations. Cryo ablations are performed utilizing a cryoballoon catheter, such as one available from Medtronic Inc. The ultimate purpose of cryoablation is to freeze tissue in a discrete and focused fashion to destroy cells in a precisely targeted area. Generally in cryo ablations tissue hypothermia causes cardiomyocytes to become less fluidic as metabolism slows, the ion pumps to lose transport capabilities, and the intracellular pH to become more acidic.

In addition to cryoballoon catheters, other balloon based catheters are also utilized. In one type of balloon based catheter, a laser energy is delivered from inside the balloon for point-by-point pulmonary vein isolation. In another type of balloon catheter, heating is applied for pulmonary vein isolation instead of freezing as with the Arctic Front® cryoballoon catheter.

In the method and system of this disclosure, any of these balloon based catheter may be used for atrial fibrillation ablation utilizing a fluoroscopy and/or medical images based cardiac mapping system of the current invention.

Other forms of ablation energy are also sometimes used, though currently they are not as common. These include, microwave energy ablations, laser ablation, and high frequency ultrasound (HIFU) ablations among others, and their use is within the scope of this disclosure. Even though the cardiac image mapping system disclosed here is described in conjunction with cyroablations, it can be used for other energy forms of ablation, such as RF, Microwave, high intensity focused ultrasound (HIFU), hot balloon and laser ablations.

For RF ablations, a contact force catheter is frequently utilized. Also, for RF ablations a non-fluoroscopic mapping system is frequently utilized. Generally, non-fluoroscopic mapping systems may be impedance based such as St Jude's Navix/Velociy system, or magnetic based such as Biosense Webster Carto mapping system.

For a non-fluoroscopic 3-D mapping system to have utility, the catheters must have sensors which communicate with and which can be registered with the image generated by the mapping system, especially the ablation catheters.

Cryoballoon ablations is one type of ablation procedure whose popularity is increasing rapidly due to many advantages that it offers over RF ablations. One big advantage of cryoballoon ablations is that the whole pulmonary vein is ablated at once, instead of point by point ablations when performed with RF energy catheters.

Cryoballoon catheters do not have sensors for registering to impedance or magnetic based 3D mapping system.

A cryoballoon catheter generally consists of a hollow shaft with a closed distal end containing a cooling electrode tip, integrated thermocouple deice and three proximal ring electrodes for recording and pacing. A console that contains the cryorefrigerant fluid. The cooling liquid travels through the inner delivery lumen to the catheter tip, where the cryorefrigerant is pressurized and released. This accelerated liquid-to-gas phase results in rapid cooling of the distal tip. The gas is then conducted away from the catheter tip through a second coaxial return lumen maintained under vacuum and evacuated in the hospital medical gas disposal system.

The console allows the operator two different modes of operation. The first is the cryomapping mode in which the tip is cooled to a temperature not lower than −30 C for a maximum of 80 seconds so as to prevent irreversible tissue damage. The second mode is cryoablation, which results in cooling of the catheter tip to at least −50 C for a programmable period (nominally 4 minutes), producing the permanent lesion. The cryomapping mode can be used for an indefinite number of times before cryoablation. Cryoablation may be initiated at any time during a cryomapping application or, from the onset, if the operator wishes to forego the cryomapping function.

Advantages of Cryo Ablations Include:
Catheter stability—Hyperthermia generated at the distal cooling electrode, the trial catheter adheres to tissue affording greater catheter stability. The operator may let go of the catheter once it is adhered onto the endocardial surface. The programmed electrical stimulation may be performed during cryoablation without concern for catheter dislodgement. Moreover brushing effects that occurred during beat-to-beat rocketing heart motions and with respiratory variations are eliminated Minimal risk of thromboembolism—To compare the propensity for RF and cryo ablation to produce hot thrombus on the surface of the ablation lesion, a randomize preclinical study was conducted involving 197 ablation lesions in 22 dogs at right atrial, right front, left ventricular sites RF energy was five times more thermogenic than cryoablation, as confirmed by results of historical morphometric analysis seven days after ablation moreover, thrombus volume was significantly greater with RF compared with cryoablation. Interestingly, the extent of IPO thermic injury was positively correlated with thrombus spoke. This was unlike bioenergy, in which lesion that mentions are not predictive of thrombus ice.

Moreover, cryothermal ablation lesions are associated with a lesser degree of platelet and coagulation cascade activation when compared with RF ablation.

Minimal risk to vascular structures—Concerns have been raised regarding RF ablation adjacent to or within coronary venous system or TVs, with venous injury (including acute perforation and tampanode, and/or delayed fibrosis/stenosis), acute or sub acute and/or luminal venous thrombosis, and collateral damage to the esophagus and/or adjacent coronary arteries being reported. Perforation, or not, and coronary artery stenosis are potential complications. The circumflex and/or coronary artery may course in close proximity to the arrhythmia substrate. Moreover, the AV nodal artery passes near the mouth of the coronary sinus, the ablation may conceivably damage this vessel. Preclinical studies suggest a lower incidence of coronary artery stenosis following cryoablation compared with RF ablation.

Painless ablation—RF ablation may be painful to the patient under conscious sedation through direct stimulation of cardiac sensory nerves or pericardial or collateral Whisler visceral irritation, particularly when ablating your thin-walled or venous structures such as posterior left atrium, coronary sinus, or posterior cable tricuspid Isthmus. In contrast to our FCA, several studies have noted that again perception, as assessed by standard Likert scale, is significantly less with cryoablation. This first select procedures associated with substantial patient discomfort, the use of cryoablation may theoretically result in lower anesthetic and analgesic requirements. This is especially relevant for electrophysiology laboratories that do not use general anesthesia. However, it should be noted that in the case of AF ablation, a rare incidence of transient ice cream headache has been described during ablation.

Visualization by ultrasound—The ability to visualize formation of ice ball by ultrasonic means was likewise demonstrated in preclinical transcatheter cryoablation studies. This feature of cryoablation has proved helpful in defining optimal freezing parameters.

General Disclosure

In the methods and system of this disclosure, medical images based cardiac mapping/electrophysiology tools is disclosed for cardiac ablations for arrhythmias. The methods and system of this disclosure can be employed with a methodology for monitoring esophageal temperature. In another embodiment, the mapping system and mapping methodology can also be used without the use of temperature monitoring. The methods and system of this disclosure can be used for atrial fibrillation (AF) ablations or pulmonary vain isolation (PVI). The method and system of the current disclosure is particularly useful for any balloon based catheter used in ablation. This disclosure can be employed for cryoballoon catheter, laser balloon catheter, hot balloon catheter, radio frequency (RF) catheters or circular diagnostic catheters for atrial fibrillation ablation techniques/methodologies.

The overall concept of this disclosure is shown in conjunction with FIGS. 1A, 1B, and 1C. Shown in FIG. 1A, a patient's surface and intracardiac signals 566 are brought into the mapping system/computer workstation 550 via interface electronics (not shown). The interface electronics circuitry includes signal amplification, signal conditioning and analog to digital (A/D) conversion. The patient's 552 medical images 557 are also brought into the mapping system/computer workstation 550. The medical images may include a combination of live, real-time images (e.g. fluoroscopy) and stored images (e.g. 3D CT images). The medical images may include fluoroscopy 558, ICE Ultrasound 560, CT images 562, MRI 564 images and others 565. Other images 565 may include computer model of a chamber created with the use of sensors, or with ultrasound based catheters.

The mapping system/computer workstation 550 is configured and programmed to process and manipulate the various images and electrical signals and display them in a manner that is useful to the physician 554, while performing the procedure. Such procedures include ablations for atrial fibrillation and other arrhythmias.

The patient's 552 esophageal temperature may, additionally be monitored 503, and based on pre-determined levels, alarms and/or automatic interrupt may also be activated in the method and system of this disclosure.

As shown in FIG. 1B, various images that are brought into the mapping system/computer workstation 550 are processed. In some cases the images are overlaid or stacked 505 on top of each other in layers. The images (when stacked and overlaid) may also be manipulated in order for them to be aligned with each other. This may be for two images or more images. In some cases more than two images are stacked 505. The system is configured such that two or more layers of images can be overlaid on top 505 of each other and the transparency of the images can be adjusted by an operator, to provide useful information regarding anatomy, and especially for the placement of a catheter in an appropriate position such as appropriate position in the left atrium, pulmonary vein ostium (OS) or other appropriate structures.

Also disclosed are methods and system for tagging or marking on the images, such as marking ablation sites for cryoballoon ablations, and storing images (shown in conjunction with FIG. 1C). The ablation tags marked for cryoballon ablations may be displayed in a review screen to aid in ablations performed with any balloon catheter, for example a cryoballoon catheter for pulmonary vein isolation for atrial fibrillation ablations. Same can be done with other balloon based catheters The general methodology for the system is described in conjunction with the flow diagram in FIG. 1D for cryoballoon ablations and FIG. 1E for radiofrequency ablations.

For cryoballoon ablations, as shown in conjunction with FIG. 1D, at the beginning of the procedure (step 450), the patient is connected to the fluoroscopy and/or medical imaging based mapping step 452. Generally, an esophageal probe is placed at the appropriate level of the esophagus for measuring esophageal temperature (steps 454 & 456) and connected to the mapping system 458. In one embodiment the temperature monitoring is part of the current mapping system. In another embodiment, the temperature monitoring is separate from the current mapping system, and may utilize a separate system available in the procedure room such as a separate cardiac monitoring/recording system, or a separate stand-alone temperature monitoring system.

In the setup of the Mapping System 458, fluoroscopy and/or medical images (e.g. intracardiac echo or ICE) are acquired into the mapping system (step 464), as well as, patient's electrical signals (both intracardiac and surface EKG) as shown in step 460. Esophageal temperature is also acquired into the Mapping System 458, and temperature based alarms and/or automatic shutoff is programmed in the computer at the beginning of the case, based on change from the baseline temperature.

The role of the mapping system is to help place the cryoballoon catheter or other balloon based catheter in the appropriate location within the left atrium and around pulmonary veins. To this end, high resolution images are recorded in the system with contrast medium ("dye") injections. The recordings may be done manually by the operator who manually starts and stop the recordings, or may be done in an automatic fashion utilizing optical character recognition (OCR) as a switch, described later in this disclosure.

Once the detailed images of the pulmonary veins are recorded, (step 466) the live fluoroscopy images are superimposed on the "enhanced" images of the pulmonary veins (obtained with "dye" injections), as shown in step 468 and described later in this application. Once the two images are superimposed, a transparency factor between the live image and recorded image is adjusted (step 470) to guide the physician in placing the balloon catheter in the appropriate position, step 472. Once the cryoballon is placed appropriately, freezing or cryoablation is started at physician's orders.

Advantageously, in this procedure the system not only guides in the optimal visual placement of the cryoballoon, but also monitors the esophageal temperature (optional), and the system acts to activate alarms and/or cut-off the ablation energy delivery based on pre-determined criteria as was set in step 462.

As well known in the art, atrial fibrillation ablations may be performed utilizing radiofrequency (RF) ablation or cryoablations (or other forms of energy). The system described in this disclosure may be used for RF or cryoablations (or other forms of energy). The flowchart in FIG. 1E describes similar steps for RF ablations. These are steps 480 from beginning of procedure to step 508 to the end of the procedure. Even though the methodology for sequence of events is similar, radiofrequency ablations is generally a much more lengthier procedure as the ablation lesions are performed point by point via a much smaller catheter, typically also containing means for contact force sensing.

The posterior wall of the left atrium is particularly targeted for ablation because the pulmonary veins enter the atrium at this area of the left atrium, encircling the pulmonary veins with continuous rings of lesions in this procedure. The esophagus may however be, in a position so as to overlie one or more of these circles, thereby making the desired encirclement difficult or impossible.

A significant and lethal complication of atrial fibrillation ablation is the accidental creation of an atrial esophageal fistula following the development of lesions on the posterior wall of the left atrium. Because the esophagus is generally in close position to the posterior wall of the left atrial, thermal injury may be communicated to the esophageal wall resulting in disruption of the wall and formation of the atrial esophageal fistula. Thermal esophageal lesions are believed to be precursors of fistula formation. Post ablation esophageal wall changes (erosion or ulceration) are reported to occur in up to 47% of patients. Such a monitoring method and system of real time temperature monitoring can detect rapid esophageal heating during radiofrequency ablation, or cooling during cryoablation.

Although the pathophysiology of left atrial-esophageal (LA-Eso) fistula formation is not fully understood, it is clear that thermal injury to the esophagus during ablation of the left atrium (LA) posterior wall plays a crucial role in triggering the cascade of events that eventually result in the development of LA-Eso fistula.

Currently, the most commonly used clinical strategy to minimize esophageal thermal injury during AF ablation involves limiting the magnitude of power 25 to 35 W, as well as the duration (<30 s), of RF applications placed along the posterior wall of the LA. A major limitation of this approach is that it fails to account for the variability in the thickness of the posterior LA wall and the presence of peri-esophageal connective tissue—important determinants of esophageal heating. Thus, empirically limiting the power and duration of RF applications may be insufficient to prevent esophageal thermal injury in all patients. RF power delivery during AF ablation, guided by luminal esophageal temperature (LET) monitoring is associated with less frequent esophageal injury compared with a strategy of power limitation alone.

Also, it is known that successful atrial fibrillation ablation may require the introduction of lesions near the location of the inferior right pulmonary vein, which is located in close proximity to the phrenic nerve. Thus, it has become more common for accidental injury to the phrenic nerve to occur. The phrenic nerve is responsible for operation of the diaphragm, and thus, injury to the phrenic nerve can be quite catastrophic.

Luminal esophageal temperature (LET) monitoring is the most common strategy to minimize esophageal injury during atrial fibrillation (AF) ablation procedures. The esophageal probe may have one thermistor, or the esophageal probe may have multiple sensors on the body of the probe for measuring temperature from a length of the esophagus.

In addition to the foregoing, fractionated electrograms and vagal plexi are also frequently present on the posterior wall of the left atrium. These are also common targets of atrial fibrillation ablation. Again, the location of the esophagus may hinder application of this sufficient energy to successfully ablate enough energy of the left atrium to prevent recurrence of atrial fibrillation.

Since esophageal injury during RF ablation in the left atrium is thermal injury, and because of the need for preventing injury to the esophagus, there is a real need for a method and system for, a) activating various levels of alarms based on esophageal temperature monitoring, b) cooling the esophagus, and/or c) automatically interrupting the energy delivery of the ablation circuit, whenever the esophageal temperature reaches a predetermined critical level.

SUMMARY OF THE DISCLOSURE

The current disclosure discloses methods and system for atrial fibrillation ablations utilizing a fluoroscopy medical image(s) based cardiac mapping system, which is also adapted for balloon based catheters including cryoballoon catheter. The method and system incorporates overlaying two or more sets of images on top of each other where the transparency between the images can be adjusted as an aid in the optimal placement of the balloon based catheters. Further, tags and markers are also placed on fluoroscopic and/or other medical images indicative of where the tissue that has been ablated. The method and system also optionally comprises the ability to monitor esophageal temperature, and to activate alarms and/or energy delivery interrupt based on pre-determined esophageal temperature parameters.

Accordingly, one objective of the disclosure is for a computer based system to overlay fluoroscopic and/or other medical images to aid in placing a balloon based catheter in the appropriate location with left atrial chamber or around pulmonary vein for performing pulmonary vein isolations for treatment of atrial fibrillation.

In another aspect of the disclosure, the cardiac system is a combination system comprising of a fluoroscope or medical images based cardiac mapping system and a temperature control system.

In another aspect of the disclosure, the fluoroscope and/or medical images based cardiac mapping system provides guidance to the physician for proper placement of cryoballoon catheter for cryoablation.

In another aspect of the disclosure, the system can be any balloon based catheters that are utilized for atrial fibrillation ablations or pulmonary vein isolations.

In another aspect of the disclosure, the fluoroscope or medical images based cardiac mapping system provides guidance to the physician for proper placement of a circular catheter for radiofrequency (RF) ablations.

In another aspect of the disclosure, the fluoroscope and/or medical images based cardiac mapping system utilizes fluoroscopy for electroanatomical mapping.

In another aspect of the disclosure, the fluoroscope or medical images based cardiac mapping system utilizes intra-cardiac echo (ICE) for electroanatomical mapping.

In another aspect of the disclosure, the fluoroscope or medical images based cardiac mapping system utilizes a combination of fluoroscopy and intra-cardiac echo (ICE) for electroanatomical mapping.

In another aspect of the disclosure, the system utilizes fluoroscopy and 2D ICE along with the electrical signals for cardiac mapping.

In another aspect of the disclosure, the system utilizes fluoroscopy, 2D ICE and CT images along with the electrical signals for cardiac mapping.

In another aspect of the disclosure, the system utilizes fluoroscopy, 2D ICE and 3D ICE along with the electrical signals for cardiac mapping.

In another aspect of the disclosure, the fluoroscope or medical images based cardiac mapping system utilizes computed tomography (CT) for electroanatomical mapping.

In another aspect of the disclosure, the fluoroscope or medical images based cardiac mapping system utilizes magnetic resonance imaging (MRI) for electroanatomical mapping.

In another aspect of the disclosure, the medical images based cardiac mapping system utilizes real-time magnetic resonance imaging (MRI) for electroanatomical mapping.

In another aspect of the disclosure, the medical images based cardiac mapping system utilizes a combination of different type of imaging modality for electroanatomical mapping.

In another aspect of the disclosure, the fluoroscope or medical images based cardiac mapping system utilizes a combination of recorded high resolution fluoroscopy and live fluoroscopy for electroanatomical mapping.

In another aspect of the disclosure, the mapping system is intended for aiding the physician perform atrial fibrillation procedures utilizing balloon based catheters.

In another aspect of the disclosure, the balloon based catheter is for cryoballon ablations.

In another aspect of the disclosure, the balloon based catheter may be for laser ablation of pulmonary veins.

In another aspect of the disclosure, the balloon based catheter may be for heating ablation for pulmonary vein isolation.

In another aspect of the disclosure, the medical images utilized are one or more from a group comprising of, stored fluoroscopy image, stored fluoroscopy video, recorded high resolution fluoroscopy with contrast medium (dye) injection, CT images, MRI images, ultrasound images, 3D fluoroscopy models, electrical impedance based computer image model, magnetic system based computer model, impedance and magnetic based computer model, or ultrasound catheter based image model.

In another aspect of the disclosure, two or more types of images may be overlaid on top of each other, where the operator can adjust a transparency factor between the images to take advantage of more detailed anatomy for a guide in placement of the catheter.

In another aspect of the disclosure, the overlaying of two or more sets of images includes live fluoroscopy image(s) with 3D volume rendered CT or MRI images.

In another aspect of the disclosure, the overlaying of two or more sets of images includes live fluoroscopy image(s) with 3D volume rendered CT or MRI images, where the CT or MR images are incorporated in segments, where each segment corresponds to a distinct anatomical structure.

In another aspect of the disclosure, the overlaying of two or more sets of images includes live fluoroscopy image(s) with 3D volume rendered CT or MRI images, where the CT or MR images are incorporated in segments, where each segment corresponds to a distinct anatomical structure, and each segment can be individually turned ON or turned OFF.

In another aspect of the disclosure, a combination of 3D volume rendered segments can selectively be turned ON and turned OFF, in any combination.

In another aspect of the disclosure, 3D CT or MRI volume rendered segments can be overlaid on the live fluoroscopy image, for guiding the placement of a balloon based catheter.

In another aspect of the disclosure, 3D CT or MRI volume rendered segments can be registered to the live fluoroscopy image, for guiding the placement of a balloon based catheter.

In another aspect of the disclosure, the placement of balloon based catheter is around left atrium or around pulmonary veins.

In another aspect of the disclosure, the overlaying of two or more sets of images includes a recorded fluoroscopy image(s) with contrast medium injection and a live fluoroscopy image(s).

In another aspect of the disclosure, the overlaying of two or more sets of images includes a recorded fluoroscopy image(s) with contrast medium injection and a CT image model.

In another aspect of the disclosure, a CT image (model) is displayed next to two layers of fluoroscopy images on top of each other.

In another aspect of the disclosure, the overlaying of two or more sets of images includes a recorded fluoroscopy image(s) with contrast medium injection and 2D ICE images for use in cardiac mapping.

In another aspect of the disclosure, the overlaying of two or more sets of images includes a recorded fluoroscopy image(s) with contrast medium injection and 3D ICE images for use in cardiac mapping.

In another aspect of the disclosure, the overlaying of two or more sets of images includes 2D ICE images and a CT image model for use in cardiac mapping.

In another aspect of the disclosure, the overlaying of two or more sets of images includes 3D ICE images and a CT image model for use in cardiac mapping.

In another aspect of the disclosure, the overlaying of two or more sets of images includes a recorded fluoroscopy image(s) with contrast medium injection, a CT image model, live fluoroscopy image(s).

In another aspect of the disclosure, the coding may utilize software which is one from a group comprising LAB WINDOWS/CVI, LABVIEW (National Instruments Corp.), C, Microsoft Visual C++, Dot Net framework, MATLAB, and Microsoft Visual Basic, or any functional equivalent software language.

In another aspect of the disclosure, the markers or tags are placed on fluoroscopy and/or medical image(s) which are indicative of where tissue ablation was performed.

In another aspect of the disclosure, the markers or tags may be on a two dimensional images(s) or three dimensional models.

The current disclosure also discloses novel methods and system for increasing safety of atrial fibrillation ablations by monitoring and interrupting energy delivery of ablation procedure, based on increases in the esophageal temperature.

The method and system of this disclosure also comprises a computer with software configured and programmed to set one or more alarms and/or computer based interrupt (shut-off) based on pre-selected levels during a cardiac ablation procedure, more specifically an atrial fibrillation procedure. Such levels can be, but not limited to, elevation in temperature level(s), or time duration of such elevation of temperature levels. The physician may select the level(s) or settings of one or more variables to suit individual patient needs. The method is configured to either set off alarm(s) or shut off the energy for the procedure or both. The baseline temperature, elevation in temperature level(s), or time duration or delay of such elevation of temperature levels have a range for the physician to select from. The range for duration may be from milli-seconds to several seconds In one aspect of the disclosure, when esophageal temperature increases above a first level predetermined threshold, an audio alarm is activated.

In another aspect of the disclosure, when esophageal temperature increases above a first level of predetermined threshold, an audio and visual alarm is activated.

In another aspect of the disclosure, when esophageal temperature increases above a second level predetermined threshold, a higher level of audio alarm is activated.

In another aspect of the disclosure, the predetermined event may be an increased level of esophageal temperature.

In another aspect of the disclosure, the predetermined event may be the rate of change of esophageal temperature.

In another aspect of the disclosure, the esophageal probe may comprise ten temperature sensors.

In one embodiment, the computer logic for esophageal temperature monitoring and corresponding alarms and interrupt logic is in a stand-alone computer in parallel to the patient monitoring system.

In another embodiment, the computer logic for esophageal temperature monitoring and corresponding alarms and/or interrupt logic is in a stand-alone computer where the esophageal signals to the stand-alone computer are obtained from the patient monitoring system.

In another embodiment, the computer logic for esophageal temperature monitoring and corresponding alarms and interrupt logic is in a stand-alone computer used independently of the patient monitoring system.

In another embodiment, the computer logic for esophageal temperature monitoring and corresponding alarms and interrupt logic and circuitry is incorporated within the patient monitoring system.

In another embodiment, the computer logic for esophageal temperature monitoring and corresponding alarms and interrupt logic and circuitry is incorporated within a 2-D or 3-D mapping system.

In another embodiment, the computer logic for esophageal temperature monitoring and corresponding alarms and interrupt logic and circuitry is incorporated within a fluoroscopy or medical images based cardiac mapping system.

In one embodiment, the cardiac system is used for guiding cardiac re-synchronization therapy.

In another embodiment, the cardiac system is used for aiding in the proper placement of left ventricular lead.

In another embodiment, the computer based system makes a table of timing information based on temporarily placing a left ventricular lead in different branches of the coronary sinus.

In another embodiment, the computer based cardiac system displays a map of timing of different locations based on different branches of the coronary sinus.

In another embodiment, the map is placed on a display screen superimposed on live fluoroscopy images.

In another embodiment, the map is color coded to display early activation and late activation times.

Various other features, objects and advantages of the disclosure will be made apparent from the following description taken together with the drawings.

BRIEF DESCRIPTION OF THE DRAWINGS

For the purpose of illustrating this disclosure, there are shown in accompanying drawing forms which are presently preferred, it being understood that the disclosure is not intended to be limited to the precise arrangement and instrumentalities shown.

FIG. 10 is an overall flow diagram of the method of the concept for temperature monitoring and ablation interrupt.

FIG. 22 is a flow diagram showing the steps for automatically recording multiple video loops from fluoroscopy, while the fluoroscopy is on.

FIG. 32 is a block diagram depicting CT images overlaid on top of recorded fluoroscopy images and live fluoroscopy overlaid on top of that.

FIG. 36 is a block diagram depicting MRI imaging overlaid on recorded fluoroscopy, and live fluoroscopy overlaid on top of that.

FIG. 41 is a diagram showing an example of one implementation where live fluoroscopy and recorded are overlaid on top of each other and the transparency between the two images has been adjusted. Further, electrical signals are also displayed on the top image.

FIG. 42 is a diagram showing an example of a CT image with volume rendering which can be combined with fluoroscopy and/or other types of medical images.

FIG. 63 is a diagraming depicting different timing measurements from LV lead pacing sites.

FIG. 64 is diagram which depicts timing from various electrode pairs of an implantable LV lead.

FIG. 66 is a table showing relative timing information stored in a table from various sites for the purpose of displaying an activation map.

DETAILED DESCRIPTION OF THE DISCLOSURE

Figure 1A:
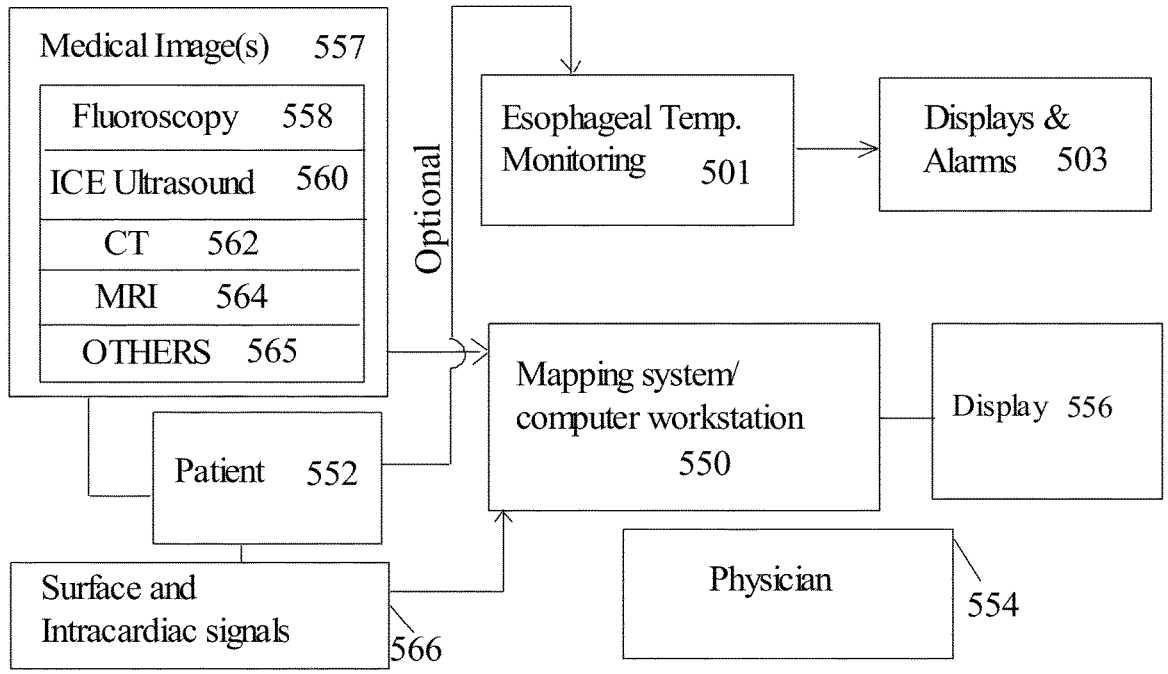
FIG. 1A is a block diagram showing overall concept of medical imaging based mapping system and temperature monitoring.
Figure 1B:
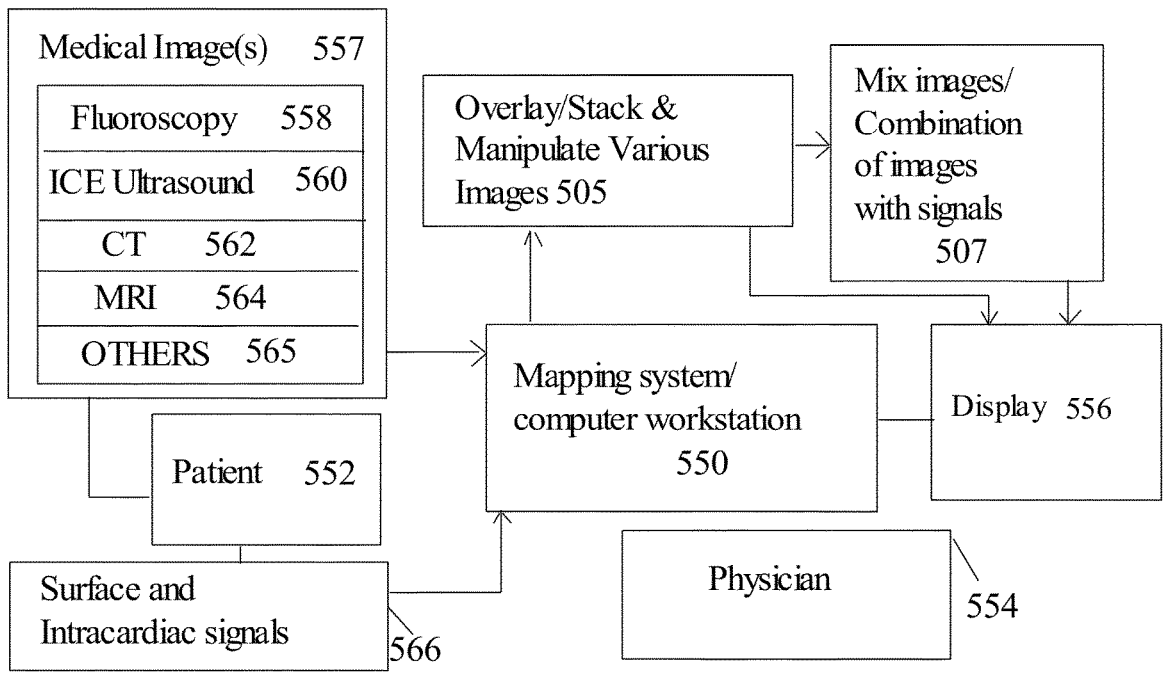
FIG. 1B is a block diagram showing the concept of the mapping system including overlaying/stacking of various images and combining various images with signals.
Figure 1C:
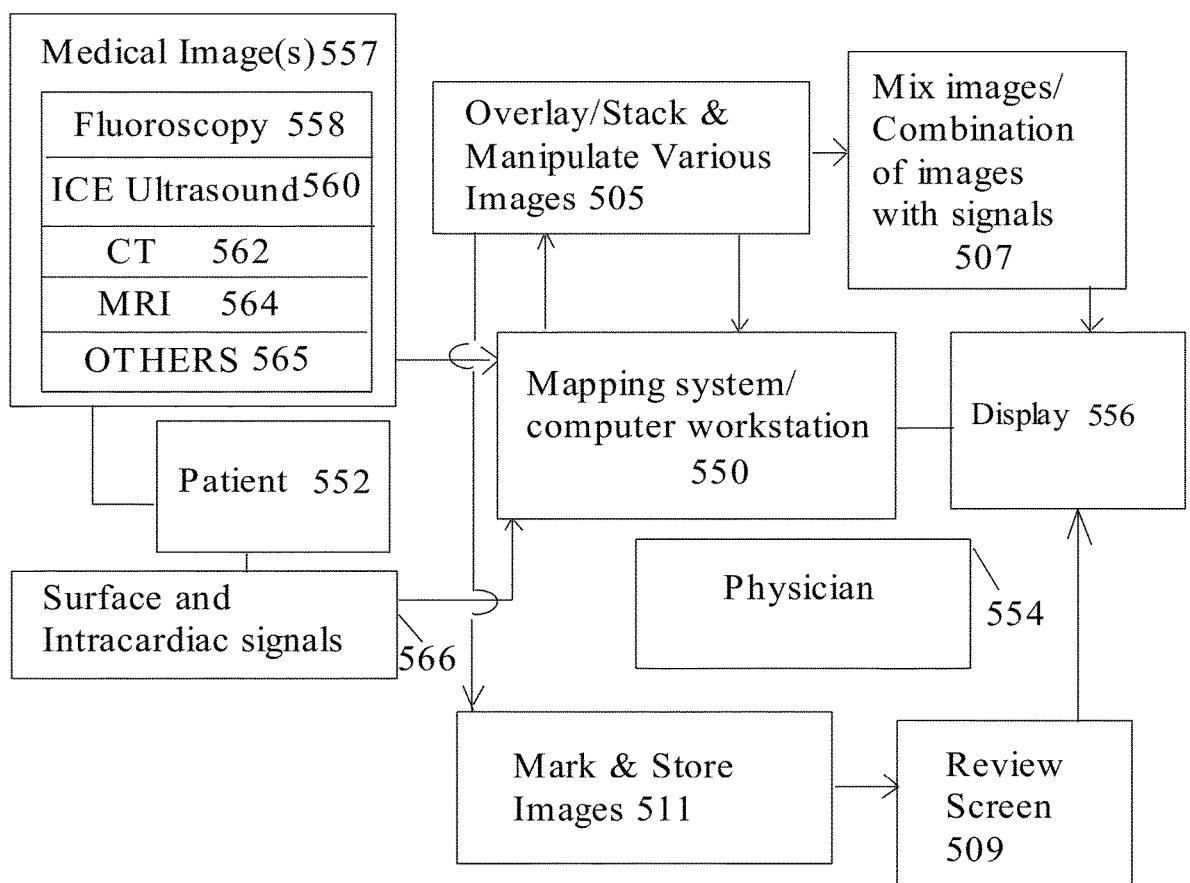
FIG. 1C is a block diagram showing the concept of the mapping system including overlaying/stacking of various images and marking and storing images.
Figure 1D:
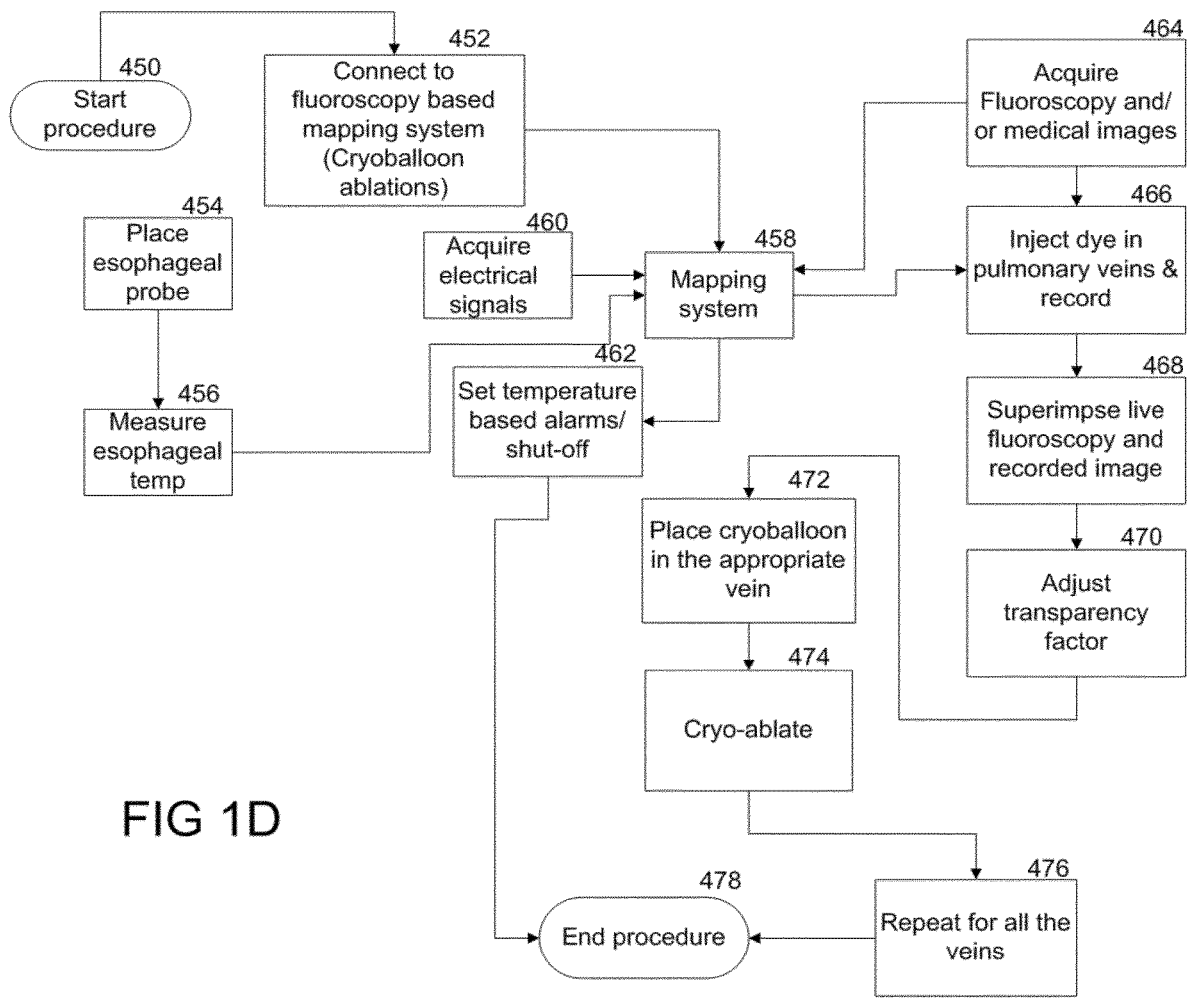
FIG. 1D is a flow diagram detailing connecting and operating temperature monitoring system and mapping system for cryoballoon ablations.
Figure 1:
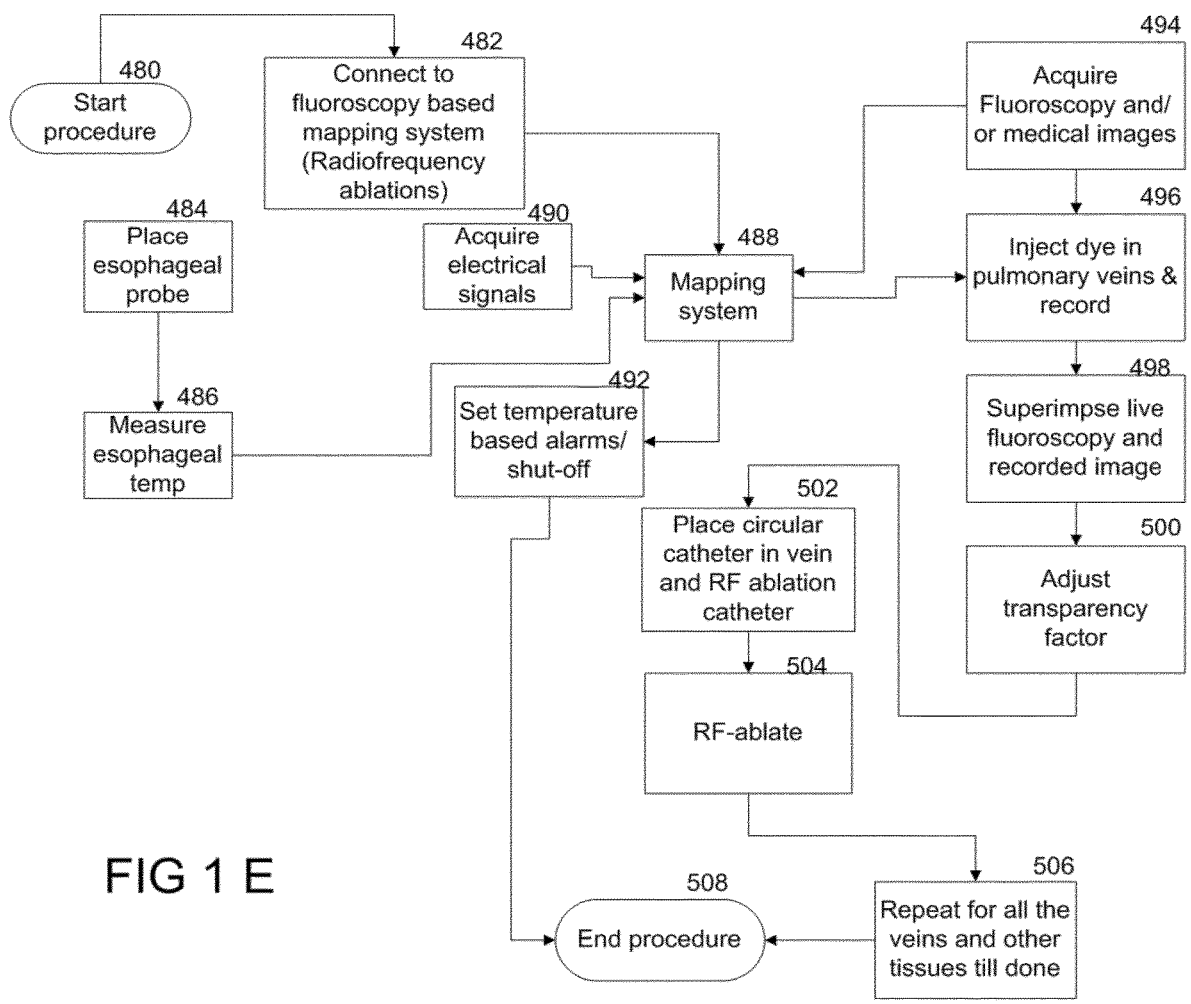
FIG. 1E is a flow diagram detailing connecting and operating temperature monitoring system and mapping system for radiofrequency (RF) ablations.
FIG. 1F is a block diagram of the concept of alarms and computer controlled interrupt based on esophageal temperature for atrial fibrillation ablations.

The following description is of the best mode presently contemplated for carrying out the disclosure. This description is not to be taken in a limiting sense, but is made merely for the purpose of describing the general principles of the disclosure.

In the methods and system of this disclosure, medical images based cardiac mapping/electrophysiology tools is disclosed for cardiac ablations for arrhythmias. The methods and system of this disclosure can be employed with a methodology for monitoring esophageal temperature. In another embodiment, the mapping system and mapping methodology can also be used without the use of temperature monitoring.

Definitions

Cardiac mapping systems are navigation and/or guidance systems used during a cardiac ablation procedure which includes making maps, guiding physicians to the optimal placement of the catheters. Cardiac mapping systems may utilize various types of medical images or a combination of medical images, or overlays of different types of medical images. They may also make a computer model of the geometry based on electrical or magnetic sensors. Cardiac mapping also utilizes the patients electrical signals derived both from surface EKG and various electrode pairs of the intracardiac catheters. Frequently in cardiac mapping a patients electrical activity is superimposed on medical images (or combination of medical images) or a derived computer model of the geometry of the heart.

3D volumetric tags in this disclosure are defined as tags which have a predefined shape and volume. The tags can be resized. The tags may be such shapes as a ring with volume, sphere shaped, shaped like a pear, or any other shape with volume.

Anatomical segment(s) in this disclosure are one or more region(s) or an organ or part thereof on a patient's CT/MRI image identified as an area of interest, wherein each such area is 3D volume rendered and is stored in a separate digital file.

In this disclosure, turning ON a segment means displaying the segment, and turning OFF a segment means removing the segment from the display.

The methods and system of this disclosure is also used for atrial fibrillation (AF) ablations or pulmonary vain isolation (PVI). The method and system of the current disclosure is particularly useful for any balloon based catheter used in ablation for atrial fibrillation. This disclosure can be employed for any balloon based catheter, including cryoballoon catheter, laser balloon catheter, hot balloon catheter, radio frequency (RF) catheters or circular diagnostic catheters, as well as other balloon catheters that are currently being developed and will be in the market soon for atrial fibrillation ablation techniques/methodologies.

As will be obvious to one skilled in the art, that the CT or MRI overlay in anatomic segments over fluoroscopy for navigation and guidance applies to any of type balloon based catheter. The navigation method and system is agnostic to the type of balloon catheter.

Mapping systems are used for navigation and guidance, and sometimes are used interchangeably.

Figure 1F:
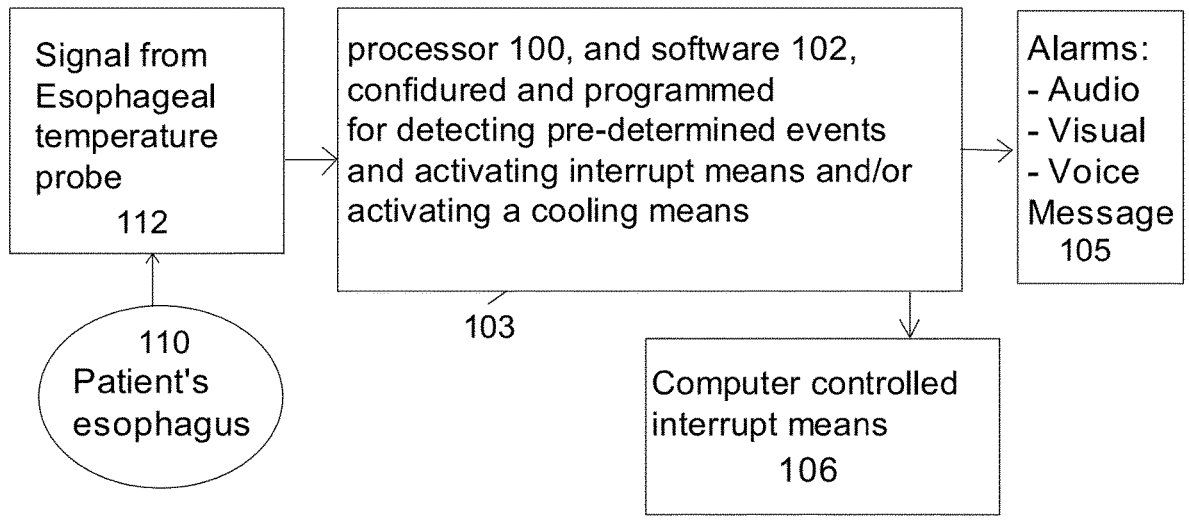

In one aspect this disclosure is targeted to preventing or minimizing thermal injury to the esophagus or the vagus nerve(s) during ablation in the atrium, for treatment of atrial fibrillation. Accordingly, as shown in conjunction with FIG. 1F signals are typically and routinely recorded from an esophageal temperature probe 112 which is in a patient's esophagus 110.

The temperature probe may comprise a single or multiple thermisters. The multiple thermister probe may comprise any number of thermisters. In one preferred embodiment, the temperature probe may have ten thermisters. In other embodiments the probe the probe may have any number of thermisters. The goal is to cover the whole esophageal region, which could correspond to the left atrium. Another goal is that the coverage is large enough so the physician shouldn't have to move the esophageal probe during the procedure.

The temperature information is typically processed by a computer 103 comprising a processor 100 with algorithms 102 for pre-determined events, and displayed on a patient monitor which may be a stand-alone patient monitor or part of an anesthesia monitoring setup, or a cardiac recoding/monitoring system. During an atrial fibrillation ablation procedure this monitoring is typically done by an anesthesiologist, a nurse or an electrophysiologist performing this procedure. In the method and system of this disclosure, various levels of alarms and controls are incorporated within the monitoring system, such that at a programmable level there is an alarm indication that the temperature on the esophageal probe 112 has increased by a pre-determined level selected by the physician. This is shown in blocks 103 and 105 in FIG. 1F. A second level(s) of alarms may also be established, indicating a further level of increase at the esophageal temperature probe. Finally, upon reaching a higher predetermined level of temperature increase, the computer may activate an interrupt means which may be a relay switch 106 or any other types of circuit breakers without limitation, which interrupts the energy delivery to the ablation circuit. At that point the physician either re-positions the catheter to another position in the atrium which is further away from the esophagus or waits for the temperature in the esophageal probe to come back down before resuming the ablation at that point.

Figure 2A:
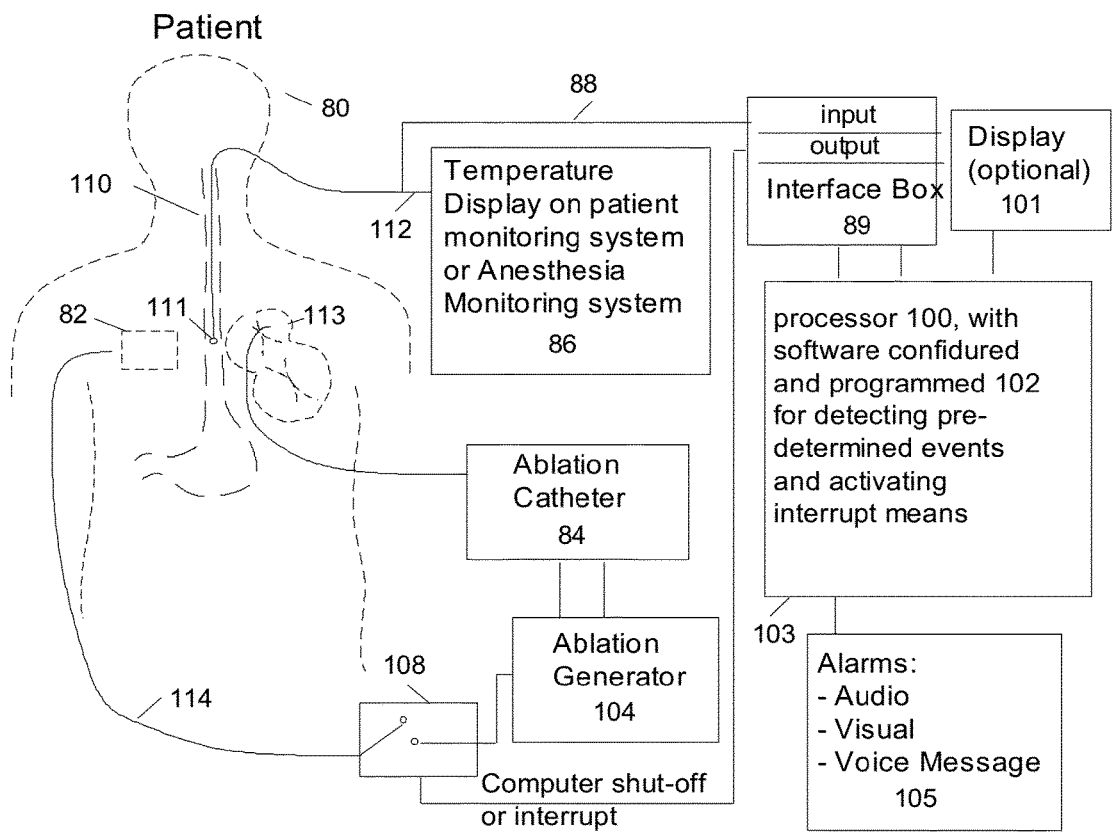
FIG. 2A depicts a general setup of the concept where the esophageal signals from the patient are split and slaved into another computer for monitoring, analyzing and interrupting atrial fibrillation ablation procedure.

This concept and various embodiments are described below in conjunction with FIGS. 2A-7. Shown in FIG. 2A is a schematic block diagram of one preferred embodiment of the disclosure. As shown in the figure an esophageal probe 112 is placed in the patient 80, such that the temperature probe 111 (usually a thermistor or a thermocouple) is in the esophagus 110 at the level of the left atrium 113, preferably at the level of the tip of the ablation catheter, and generally close to the ablation catheter which is in the left atrium 113.

In one embodiment the signal from the esophageal probe 112 is spilt or the signal is slaved 88 into an interface box 89 such that the information can be analyzed by a computer of the patient monitoring system 86, which is typically observed and monitored visually by the anesthesiologist or a nurse, and an additional computer 103 comprising processor 100 and algorithms 102 (software which is configured and programmed as described in the disclosure). In this disclosure, software and algorithms may be used interchangeably.

In one preferred embodiment, the signals from the probe are brought into a computer based system. The computer based system may be a cardiac mapping system, a cardiac monitoring/recording system, or a stand-alone system.

Figure 8A:
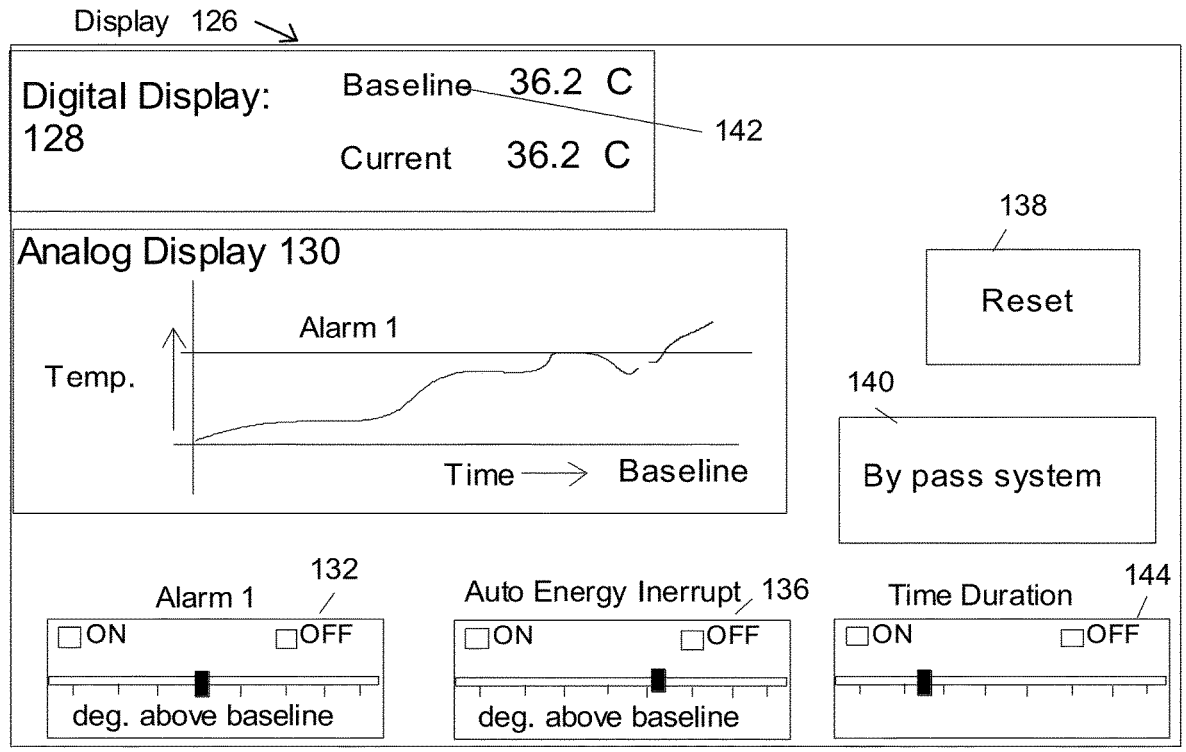
FIG. 8A shows an example of graphical display and graphical interface of the concept.

The slaved signals 88 which are brought into the separate computer 103 (via the interface box 89) are analyzed and displayed 101. The display is both in the form of graphs and digital readout of temperature, and is described later in conjunction with FIGS. 8A, 8B, 9D. The computer 103 comprises software which is configured and programmed to monitor temperature levels, and trigger one or more level(s) of alarm(s) and/or activate ablation interrupt, when predetermined threshold limits are reached. In one aspect, at the start of the ablation procedure the baseline temperature of the patient is set into the computer by the operator. This value acts as the baseline for any increase in temperature as the ablation procedure progresses, and various lesions are delivered. Typically numerous lesions are delivered during the course of the ablation procedure. Without limitation in one embodiment, there are two levels of alarms, after which an automatic interrupt takes over computer controlled by a relay switch or other interrupt means. In another embodiment, there are more than two levels of alarms.

The following description is meant to be illustrative and not limiting. In one embodiment the first alarm is set to a first value, which is a threshold value that can be easily entered or adjusted on the graphical interface of the computer (shown later in conjunction with FIG. 8A, 8B, 9D). When the first level of alarm is reached there is both sound warning and an optional light warning coming from the interface box (or the computer). When the second level of alarm is reached, both the audio and visual levels get stronger (or more intense). Finally, when the temperature reaches the next level, which is pre-determined or pre-defined by the healthcare operator, there is a computer controlled temporary interrupt or shut-off of the energy delivery from the ablation generator 104. As shown in conjunction with FIG.

2A, upon detection of the limit by the software the computer 103 gives a command signal via the interface box 89, such that the relay switch 108 (as one example of interrupt means) which is placed in the ablation circuit is opened and the energy delivery is interrupted. At this point, the physician either repositions the catheter to a site further away from the esophagus 110, or waits for the temperature to come back down. The ablation energy delivery can be re-started at any time by simply re-setting the switch using either a software or a hardware switch.

In the example of the above embodiment, say the physician has the first alarm set to a level of 0.25° C., the second alarm set to a level of 0.50° C., and the third alarm set to a level of 1.0° C. When the temperature increases to above 0.25° C. of the baseline, a beep or buzzer sound is activated along with the flashing light. At this point the physician may steer the catheter to a site which is further away from the esophagus 110 or may hold off on the energy delivery, or may finish the current burn being aware that this is the first alarm. If the temperature continues going up, and reaches the pre-determined threshold for the second level of alarm, the physician may more readily interrupt the ablation burn, unless at a critical point or seconds away from finishing the current burn. If at any time, the temperature reaches the threshold for automatic interrupt or shut-off, a command signal from the computer 103 via the output side of the interface box 89, opens the relay switch 108 interrupting the ablation circuit, and stopping the energy delivery to the tissues. At this point the physician or the operator resets the circuit. Again the physician may keep ablating after moving the catheter to a site which is further away from the esophagus 110 or wait until the temperature drops back down to a normal level before ablating again.

An example of first alarm may be a buzzer, a tone, or intermittent beeps. In such a case the second alarm may be a higher level of buzzer, tone, or more frequent beeps indicating a higher level of concern than the first alarm. In the case of a flashing light or LED, the second level of alarm may be more rapid and more intense flashing or higher frequency of LED flashing. There may also be an additional voice message also reciting the values of the temperature measurement. The above are examples only, and are not meant to be limiting. In the case of an automatic computer based interrupt or shut-off, the software may be configured and programmed such that as the temperature drops back to a pre-determined normal level, the system switch will reset itself.

Since sustained elevated temperatures may be related to thermal injury, in one embodiment the automated shut-off may be a combination of higher than baseline temperature and time duration. For example the elevated temperatures stay at a higher level for an adjustable and programmable period of time. Therefore in this embodiment the auto shut-off is based on increases in temperature and time duration of elevated temperature.

Figure 2B:
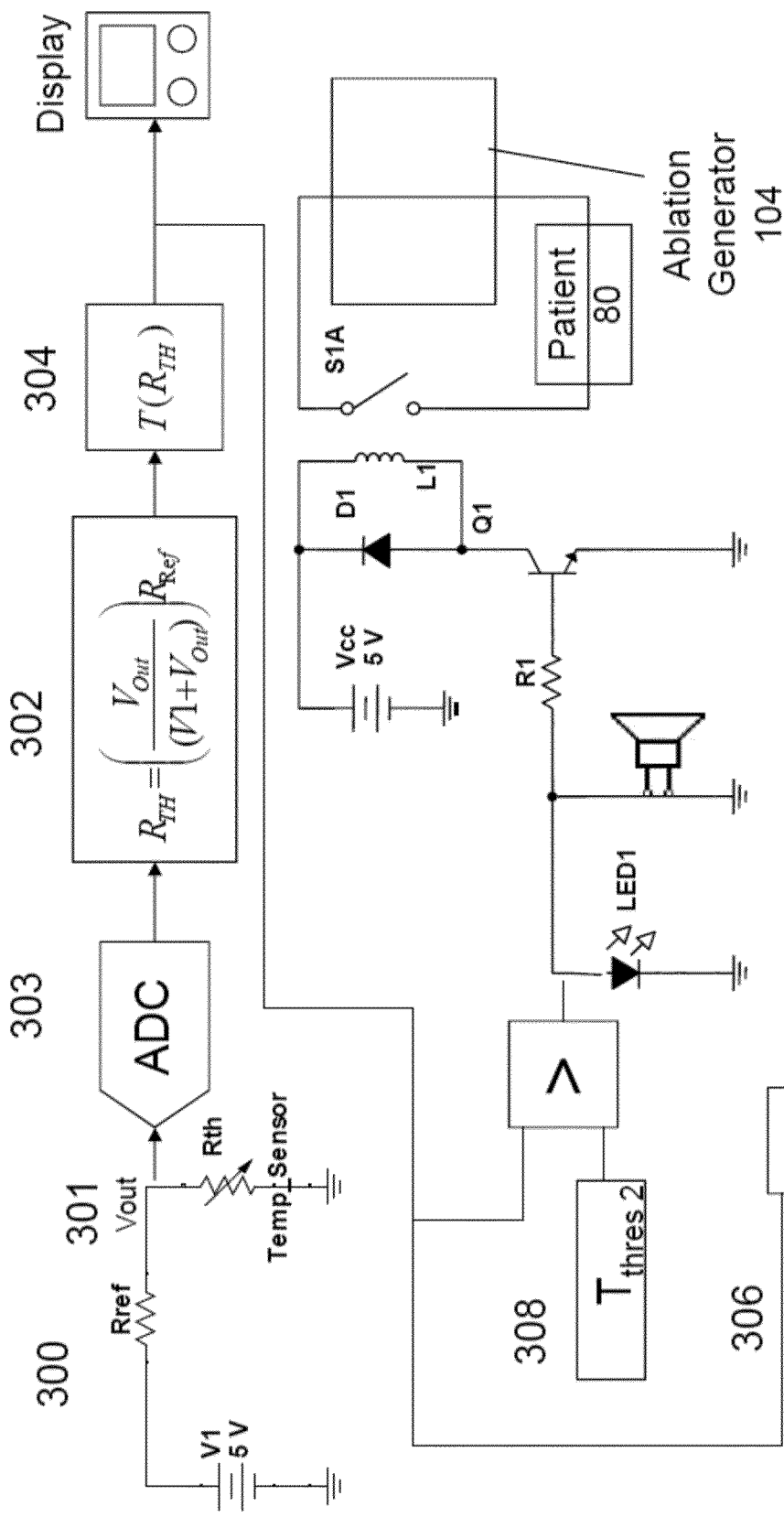
FIG. 2B depicts one implementation of the system and method.

Shown in FIG. 2B is a block and circuit diagram for one implementation of this disclosure. Other functionally equivalent circuitry can also be used. The temperature sensor setup in block 300 outputs a voltage that varies with temperature 301, in a thermister based system. The analog voltage signal is converted to digital signal by the ADC 303 and transformed to an impedance change 302 where $R_{Ref}$ is a reference resistor chosen close to operating impedance of the temperature sensor. Shown in block 304, the impedance is converted to a temperature change using sensor specifications.

The temperature is compared to the first threshold 306 and if it's greater, an LED 307 and sound alarm 309 are activated. As shown in 308, if the temperature exceeds the second threshold, a relay is also activated that switches off the ablation generator 104 or interrupts the energy delivery. Using similar methodology, more than one level of alarm may be used (not shown in the figure).

It will be clear to one of ordinary skill in the art, that the above concept can be practiced in various ways. For example, as shown in conjunction with FIG. 3, instead of splitting or slaving the temperature signal into both the patient monitor and another computer 103, the second set of signals to computer 103 may be gotten directly from the patient monitoring system 86 into the interface box. This simplifies the connections, providing that there is an output available from the patient monitoring system 86.

In one embodiment, the concept may be practiced independent of the patient monitoring system or anesthesia monitoring system. In this embodiment, as shown in conjunction with FIG. 4, the esophageal temperature probe 112 is connected directly to the interface box 89, which sends signals to the computer 103 which has the processor 100 with software configured and programmed with algorithms 102 capable of detecting pre-determined events. In this embodiment the anesthesiologist is relieved of the burden of monitoring esophageal temperature.

In one embodiment, the algorithms for detection of esophageal temperature alarm 102, limits and logic for automatic computer shut-off or interrupt 106 may be incorporated into the computer of a patient monitoring system 86. This embodiment is shown schematically in conjunction with FIG. 5. The esophageal probe 112 is connected to the monitoring system or anesthesia monitoring system 86 in the usual manner. In this embodiment, the software with algorithms 102 of the system 116 is configured and programmed to incorporate the algorithms for detection of out of range limits. Further, under conditions where an automatic interrupt or shut-off is warranted, an interface unit 117 connects to the relay switch 108 (or other interrupt means) for the shut-off or interrupt. In this embodiment, the patient monitoring system 116 is also configured with audio alarms, visual alarms, and voice messages 105. The advantage of this embodiment is that a second parallel computer is not required.

Figure 6:
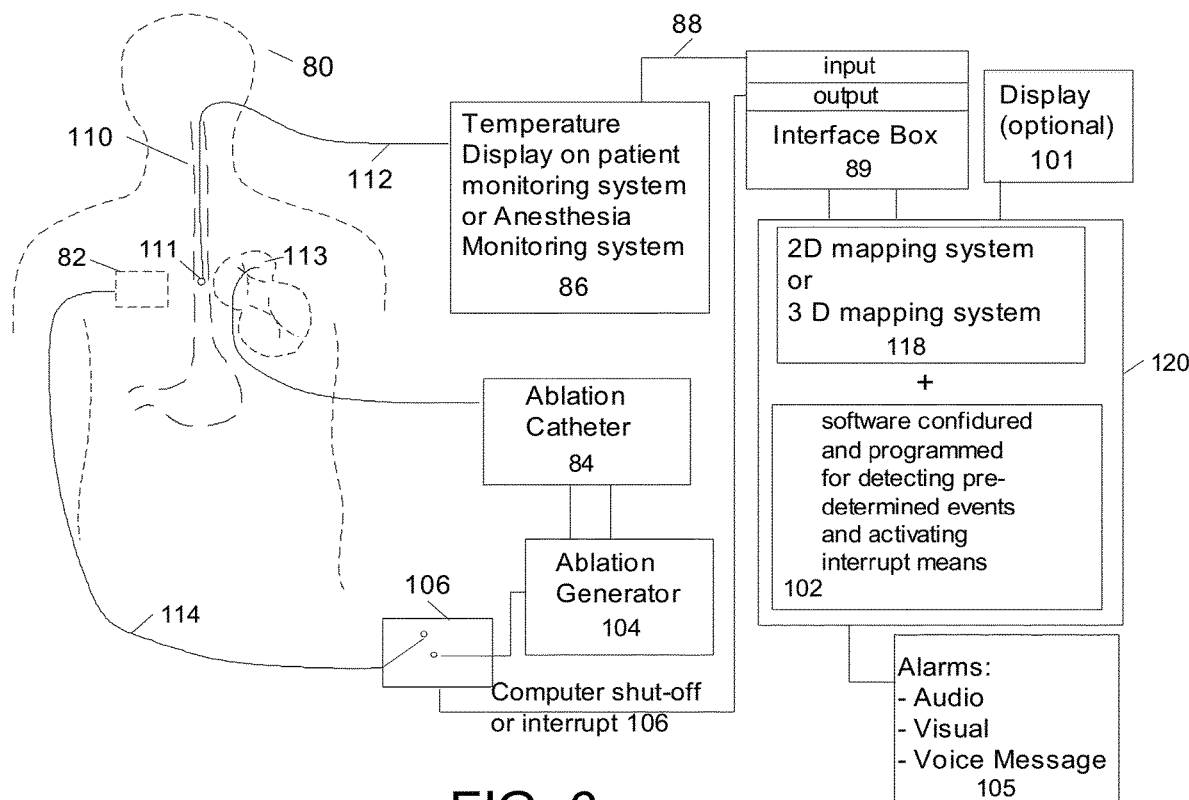
FIG. 6 depicts a general setup of the concept where the esophageal signals from the patient are split and slaved into a 2-D or 3-D mapping system, and where the logic for alarms and automatic interrupt is incorporated within the 2-D or 3-D mapping system.

In another embodiment, the software algorithms for esophageal temperature monitoring and out-of-range limit alarms may be incorporated into a 2-D cardiac electrophysiology recording or monitoring system, or a 3-D cardiac mapping system. This is shown in conjunction with FIG. 6. Examples of 2-D cardiac electrophysiology systems include, the CardioLab™ system of GE Healthcare, CR Bard's recording system, and electrophysiology recording system marketed by St. Jude Medical. Examples of 3-D mapping systems include Biosense Webster's Carto™ mapping system, St Jude's Navix™ mapping system, and a mapping system by Boston Scientific's Rhythmia Medical's mapping system. In this embodiment, as shown in conjunction with FIG. 6, the esophageal probe 112 signal is either slaved 88 into the electrophysiology monitoring or recording system 118 via an interface box 89 or directly connected to cardiac recording or mapping system (not shown). In this embodiment, the software of the monitoring system or mapping system 120 is configured and programmed such that the algorithms for detection of out of range limits for esophageal temperature are incorporated. As shown in FIG. 6, the system 120 also controls the automatic shut-off or interrupt and the audio, visual and voice messages 105.

Figure 7:
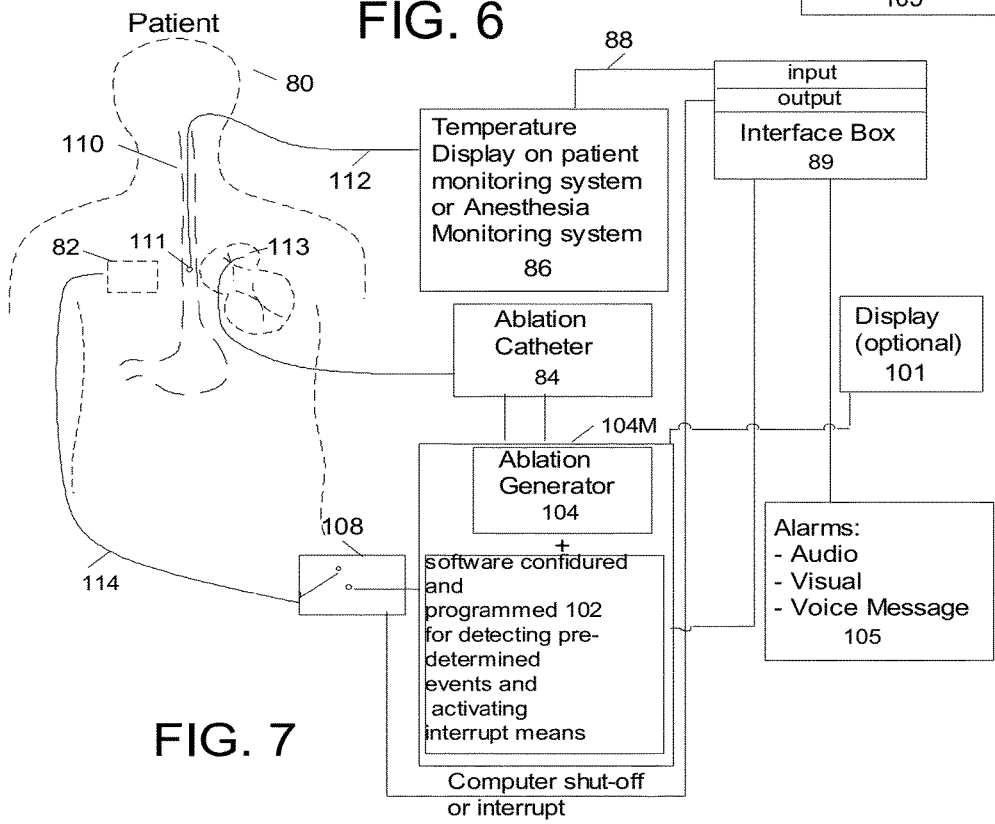
FIG. 7 depicts a general setup of the concept where the esophageal signals from the patient are split and slaved into the ablation generator, and the logic for alarms and automatic interrupt is incorporated into the ablation generator system.

In another embodiment, the algorithms for temperature monitoring and out of range limit alarms may be incorporated in the ablation generator system 104M. This is shown in conjunction with FIG. 7. In this embodiment, the standard ablation generator 104 is modified such that the controller in the modified ablation generator 104M comprises software which is configured and programmed to handle the algorithms for temperature monitoring from the esophagus 110, and implement out of range limit alarms 105 and computer shut-off or interrupt 106. As shown in FIG. 7, in this embodiment, the temperature probe signals are slaved and are connected to the modified ablation generator 104M via an interface box 89. The logic functions of alarms 105 and interrupt 106 are now configured and programmed 102 within the ablation generator 104M.

Figure 3:
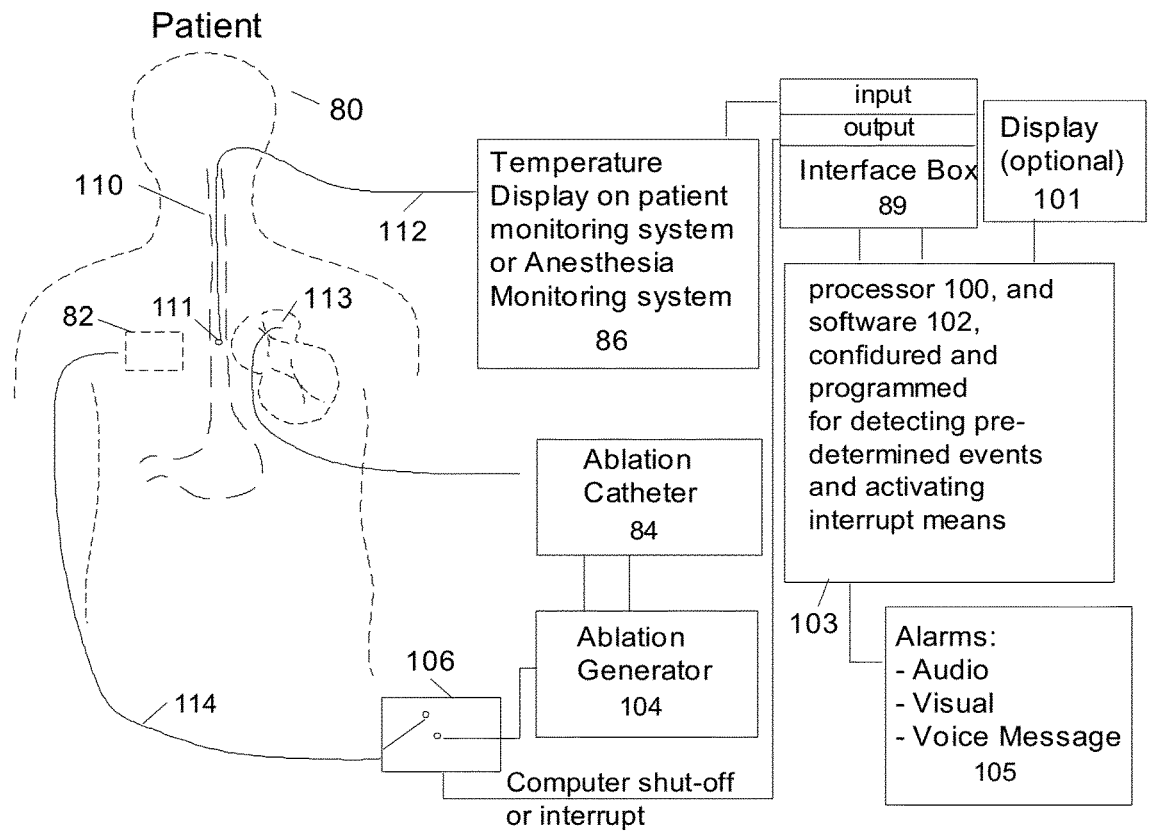
FIG. 3 depicts a general setup of the concept where the esophageal signals from the patient are brought into another computer from the patient monitoring system.
Figure 4:
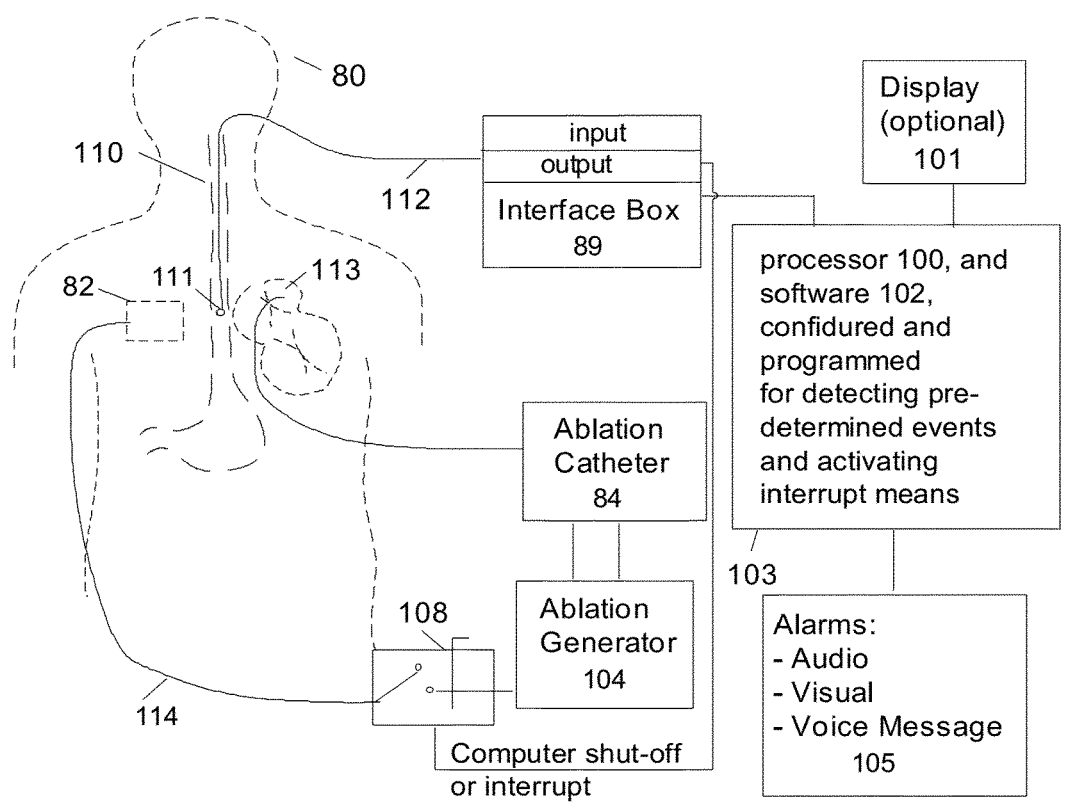
FIG. 4 depicts a general setup of the concept where the esophageal signals are brought into a computer for monitoring without using the patient monitoring system.
Figure 5:
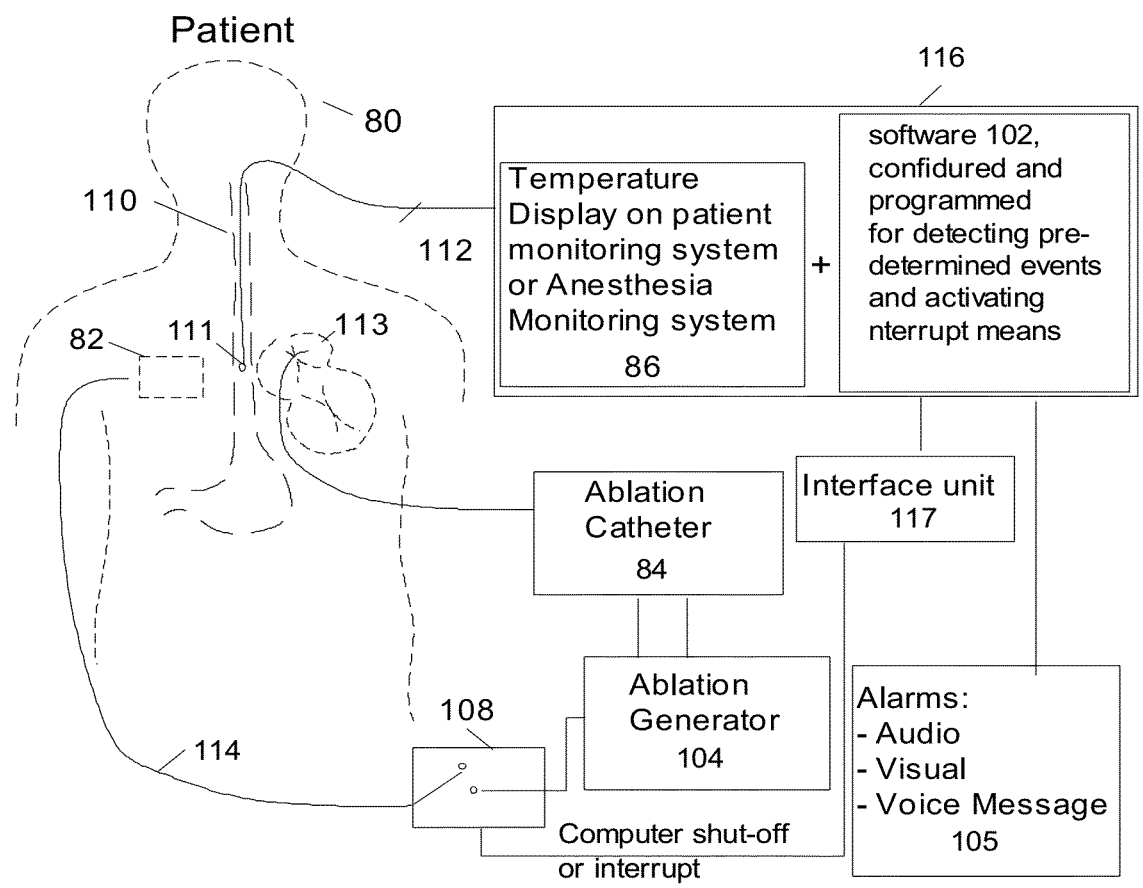
FIG. 5 depicts a general setup of the concept where the esophageal signals are monitored by the patient monitoring system and the logic for alarms and automatic interrupt is incorporated into the patient monitoring system.

As was shown in FIG. 3, the computer 103 has a display 101. This is shown in conjunction with FIGS. 8A & 8B as display 126. There is both a digital display 128, and an analog display 130. At the beginning of the atrial fibrillation ablation procedure the baseline temperature 142 is updated. Following that, the computer program tracks the temperature relative to the baseline 142. First alarm (Alarm 1) 132 can be turned ON or OFF. In one example, there is a simple sliding scale to program the threshold level for the first alarm provided it is turned ON. Similarly, a second alarm (Alarm 2) 134 (shown in FIG. 8B) can be turned ON or OFF. If Alarm 2 is turned ON, the threshold level for Alarm 2 is greater than Alarm 1, and can be adjusted simply by the sliding scale in this example.

In addition to the first and second alarms, there is an Auto shut-off feature 136 also. The Auto shut-off 136 feature may be used in conjunction with Alarm 1 and Alarm 2, or the two alarms may be turned OFF and Auto shut-off 136 may used alone by itself. The threshold criteria for the Auto shut-off 136 can be entered in a similar manner by adjusting the sliding scale. There is a Reset button 138 for bringing all the values to default values, and adjusting the parameters again. As shown in the figure, there is a Bypass button 140, to take the computer and system out of the loop from the ablation procedure, if an operator so desires for any reason.

Figure 8B:
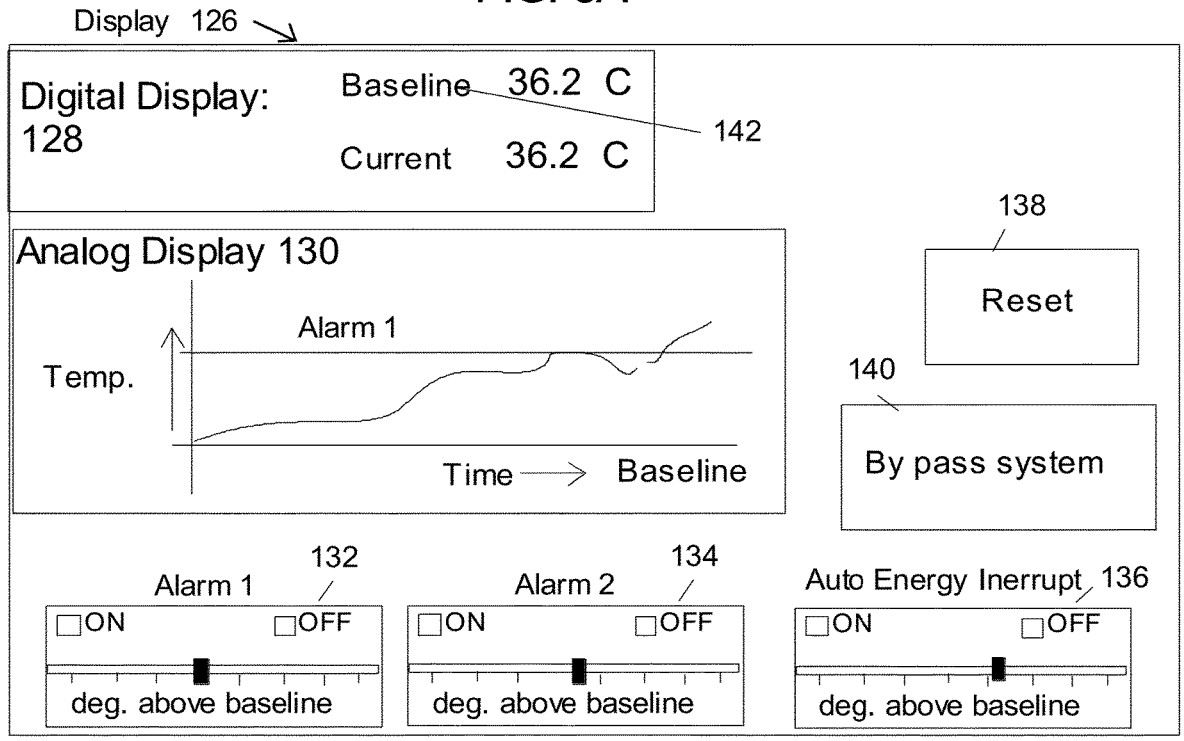
FIG. 8B shows an example of graphical display and graphical interface of the concept with adjustable time delay.

FIG. 8B shows an example of graphical display and graphical interface of the concept with two levels of alarms, alarm 1 and alarm 2.

It will be clear to one skilled in the art that various different software's may be used in implementing this concept and methodology. Program code can be written using one of several commercially available software packages. The software that can be used for this purpose is LAB WINDOWS/CVI, LABVIEW (National Instruments Corp.), C+, Microsoft Visual C++, Dot Net framework, MATLAB, and Microsoft Visual Basic, among others. Use of these or other comparable languages for this purpose that are available now or developed in the future, is considered within the scope of the disclosure. Testing of applicant's prototype has been performed using Microsoft visual C++, LabView and MATLAB.

Figure 9A:
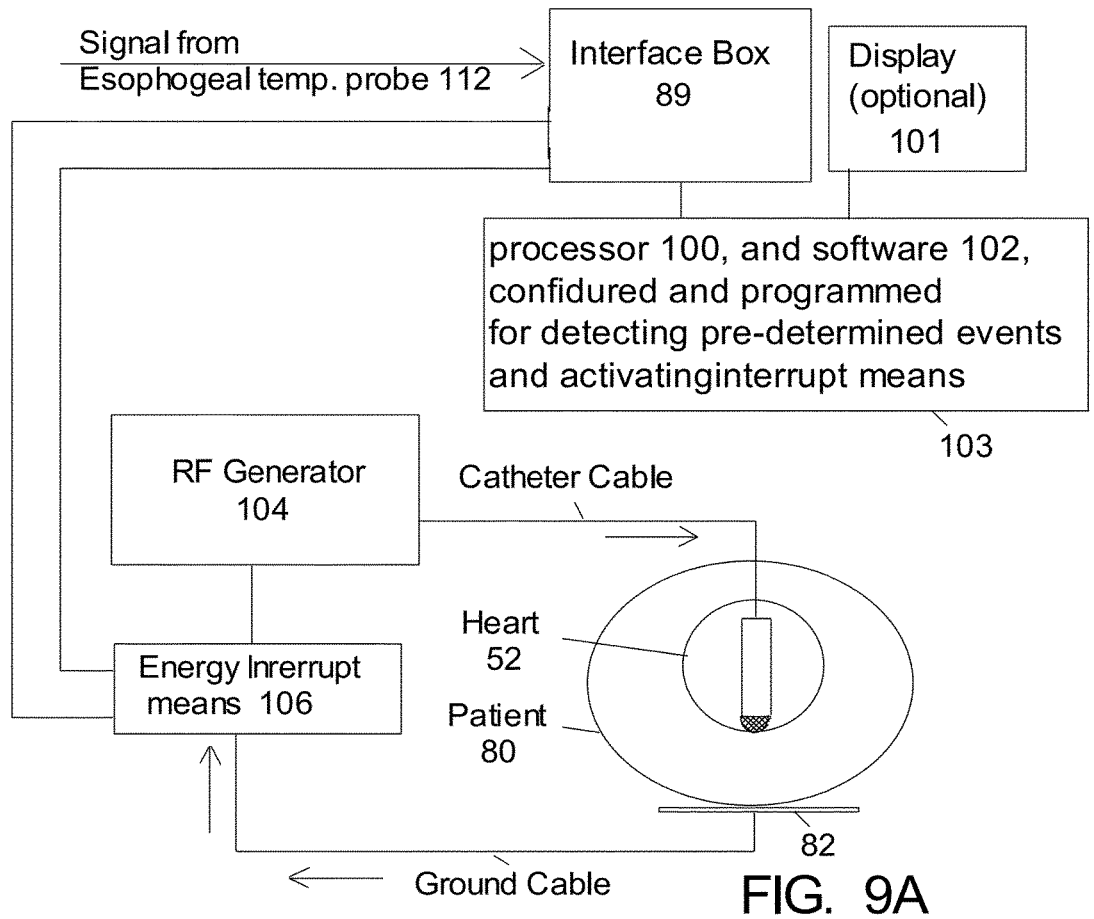
FIG. 9A depicts schematically the overall concept of the system, with the circuit interrupt in the ground loop portion of the circuit.

FIG. 9A summarizes schematically the ablation circuit and its relation to esophageal temperature monitoring circuit and automatic interrupt of ablation energy delivery. Signal from the esophageal probe 112 is brought into the computer 103 via the interface box 89. Computer 103 comprises software configured and programmed with algorithms 102 capable of detecting pre-determined events and computer based interrupt of energy delivery. When a pre-determined threshold criteria is met, the control switch will interrupt the ablation energy delivery to the circuit. As shown in the figure, energy interrupt means 106 is placed in the return path of the ablation circuit. Alternatively, the energy interrupt means 106 can also be placed on the catheter side of the circuit.

In one aspect of the disclosure, instead of just indicating alarms and interrupting energy delivery, active attempt is made to cool the esophagus. In one aspect active cooling of the esophagus is performed by itself. In another aspect of the disclosure active cooling of the esophagus is performed in conjunction with various alarm(s) and automatic interrupt.

Figure 9B:
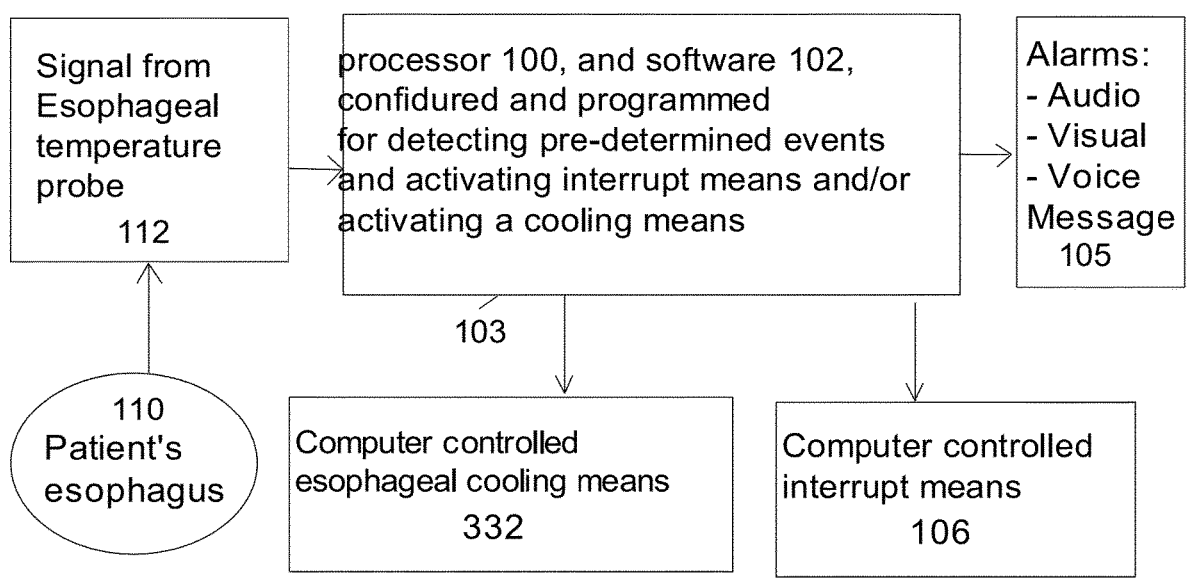
FIG. 9B depicts in block diagram the concept with computer controlled esophageal cooling means.

Shown in conjunction with FIG. 9B, as before a temperature probe 112 is inserted into the esophagus 110. Additionally, apparatus for cooling the esophagus is also inserted. In one aspect it is a saline balloon which is flushed with cool saline from an external saline bag. For the practice of this disclosure any other means of cooling the esophagus 100 may be used. As shown in FIG. 9B the esophageal cooling apparatus is controlled by a controller based on pre-programmed algorithms.

Saline or salt water typically freezes at 39° F. Therefore, without limitation in one embodiment temperatures in the range of approximately 40° F. and 55° F. may be used. Other temperatures may also be used. The decision of the temperatures will generally be determined by the lab.

Figure 9C:
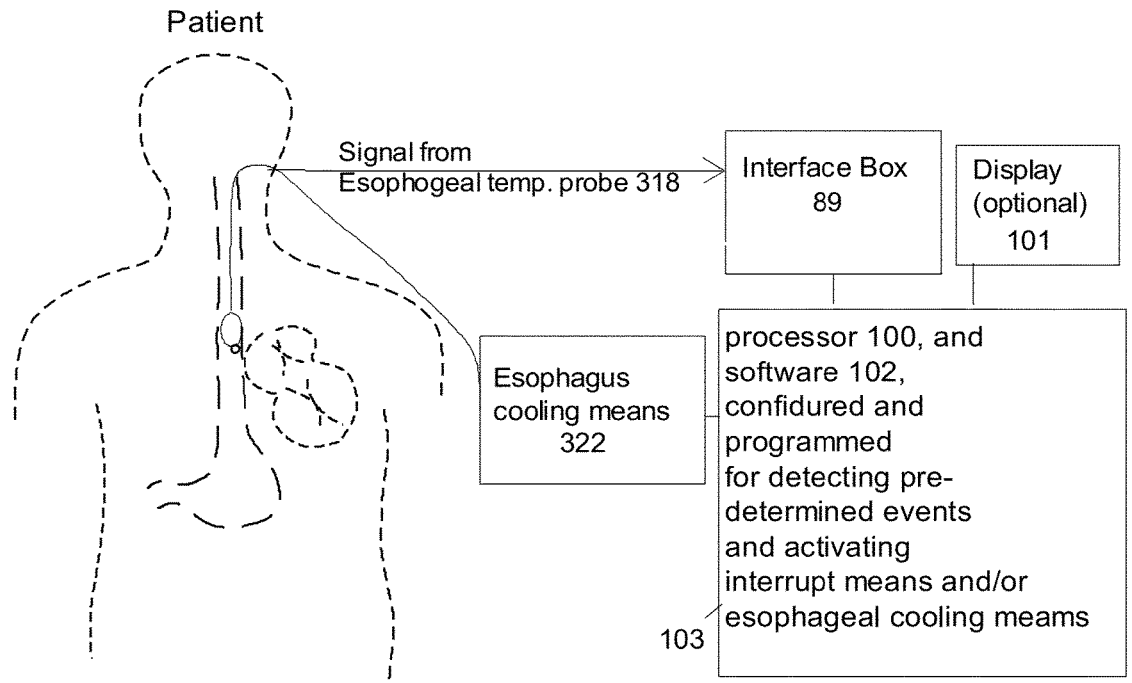
FIG. 9C depicts the embodiment where the cooling means comprises a saline bag filled with cold saline that can be used for cooling the esophagus.
Figure 9D:
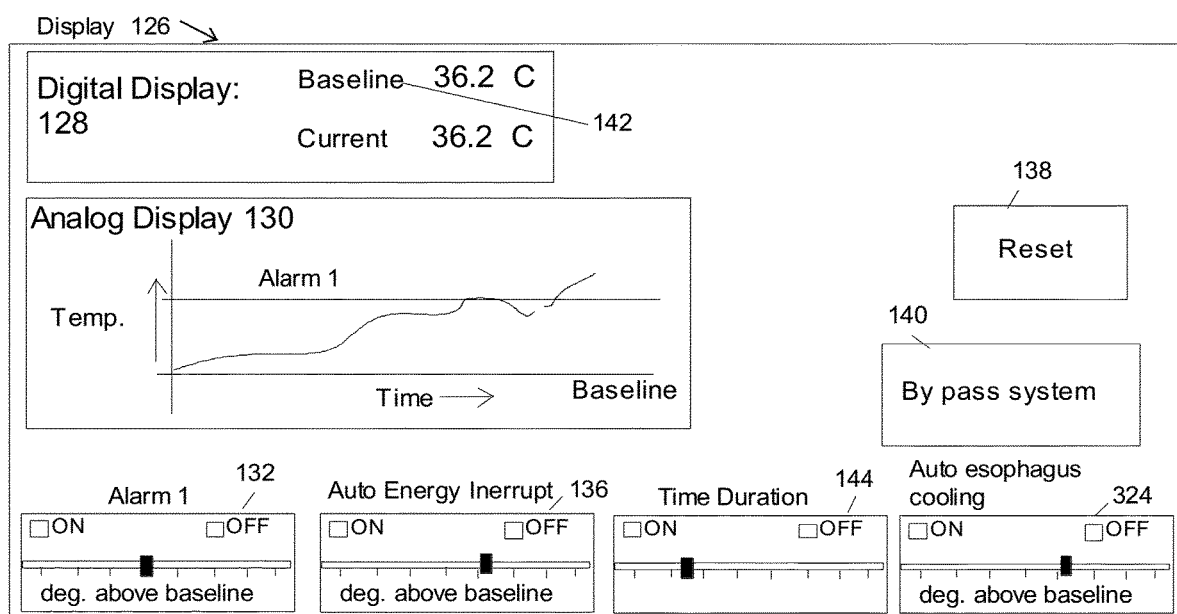
FIG. 9D shows an example of graphical display and graphical interface of the concept with Auto esophagus cooling.

Shown in FIG. 9C is one embodiment of this invention. As shown in the figure, in this embodiment a modified esophageal temperature probe 318 includes a balloon 310 which can be filled with cold saline to cool the temperature of the esophagus 110. The cold saline is supplied from a saline bag 314 which may be placed on a stand similar to a saline drip, which is common in procedure rooms. As also shown in the figure, the flow of cold saline is controlled by controller 103, which receives its input from the temperature probe based on the programmed values. It may also be controlled by a separate controller. Therefore in one embodiment as the esophageal temperature reaches a pre-determined level, an alarm may be activated. Additionally, as the esophageal temperature reaches the next pre-determined level, cool saline may be deposited in a balloon or pouch 310 which is located adjacent to the temperature probe 111 inside the esophagus. Further, if the temperature increases further to a next pre-determined level, the ablation energy may be interrupted. All of the above events will be activated according to the program setting as entered by the operator.

It will be clear to one skilled in the art that pre-determined event(s) can trigger alarm(s), an energy interrupt, or esophageal cooling means or any combination of these.

FIG. 10 depicts a flowchart of a typical procedure. The flowchart 350 begins at block 352 where the equipment is set up and connected to the patient. The procedure begins as shown in block 354. The temperature probe is positioned in the esophagus, block 356 and the program is started block 360. The operator enters pre-determined levels for one or more alarms 360 as determined by the physician. The operator also enters per-determined level of temperature increase for ablation interrupt 362, also as determined by the physician. The ablation catheter is then positioned and ablation energy is started as shown in step 364.

In one aspect, a temperature probe comprising multiple thermisters is utilized. Any number of thermistors on an esophageal probe may be utilized. An advantage of multiple thermistors is that it covers a relatively larger area of the esophagus, as opposed to a small segment with just one thermistor. Advantageously, the temperature probe with multiple thermistors does not have to be moved, or re-positioned less often once it is initially placed in the esophagus. Further, it will even protect patients with large left atrial sizes. The overall concept utilizing esophageal probe with multiple thermistor (or thermocouples) is shown in conjunction with FIG. 11. In this disclosure, even though examples are shown with 10 and 12 thermistor probes (sensors) on the esophageal probe, it will be clear to one skilled in the art, that with slight modification of the hardware and software, any number of thermistors (or thermocouples) may be utilized.

Figure 11:
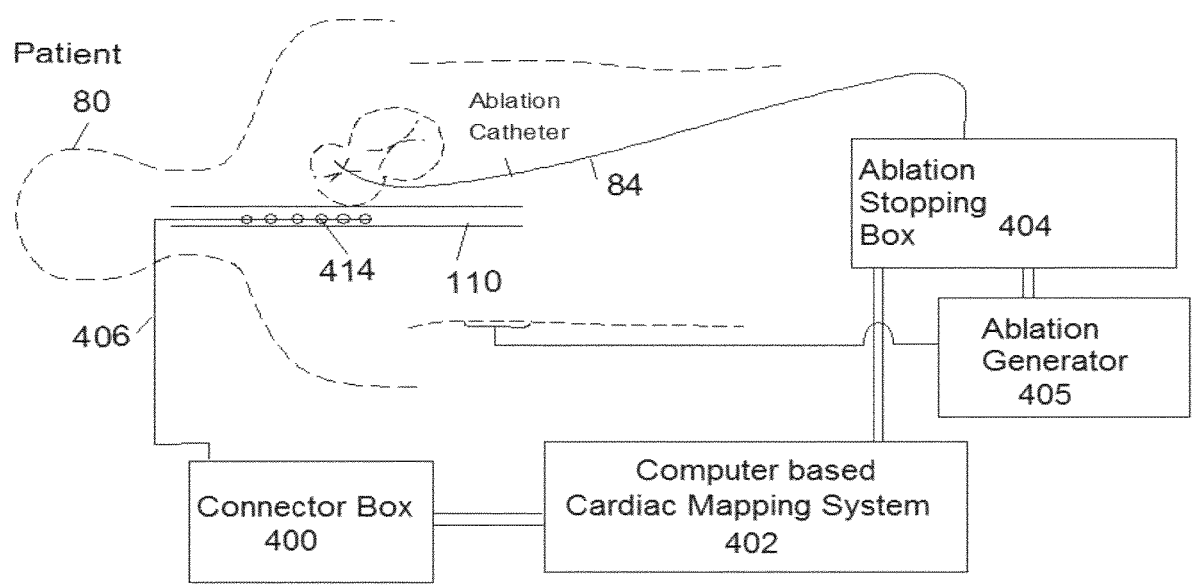
FIG. 11 is a block diagram of overall concept showing monitoring of temperature from an esophageal probe and processing temperature information in a cardiac mapping system.
Figure 12:
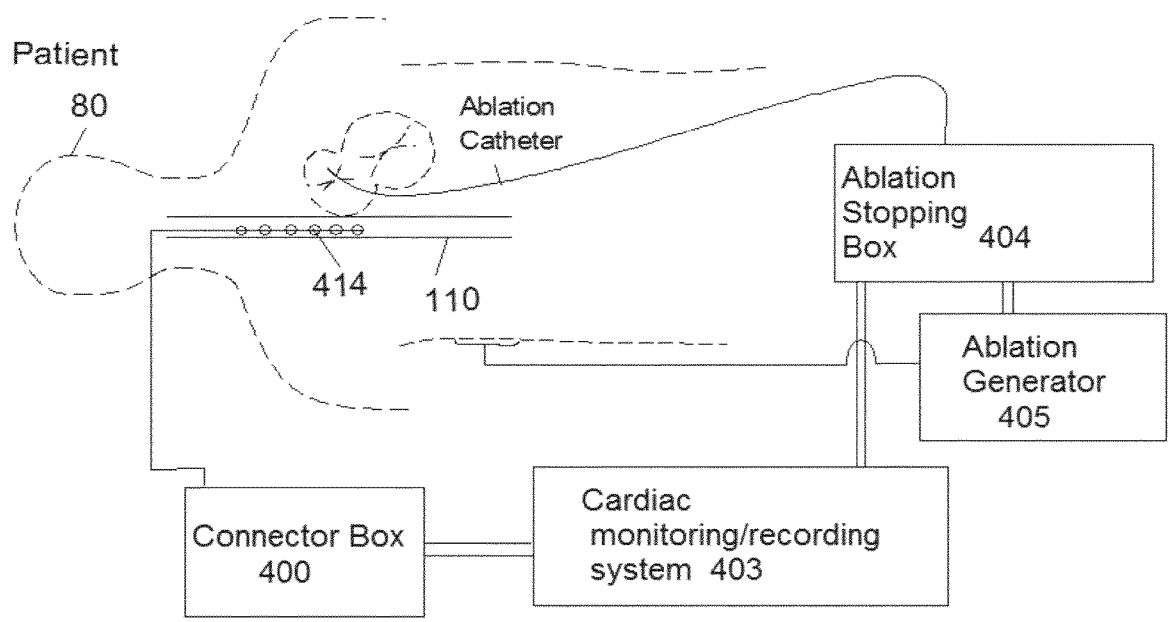
FIG. 12 is a block diagram of overall concept showing monitoring of temperature from an esophageal probe and processing temperature information in a cardiac monitor/recording system.

As shown in FIG. 11, patient 80 is inserted with a multiple thermistor esophageal probe 414. The temperature information from the esophageal probe 414 is brought into a cardiac mapping system 402 (or cardiac monitoring/recording system 403, shown in FIG. 12) via an interface connector box 400.

The cardiac mapping system 402, may also be connected to an ablation stopping box 404 (or energy interrupt box 404). The ablation interrupt box 404 is connected in-between the ablation catheter 84 and the ablation generator 405. Based on a command signal from the cardiac mapping system 402, the ablation stopping box 404, which is between the ablation catheter 84 and the ablation generator 405, interrupts the energy delivery of the ablation catheter 84 during the procedure, based on reaching the criteria of pre-determined conditions set by the operator or the physician, before the ablation starts.

Figure 13:
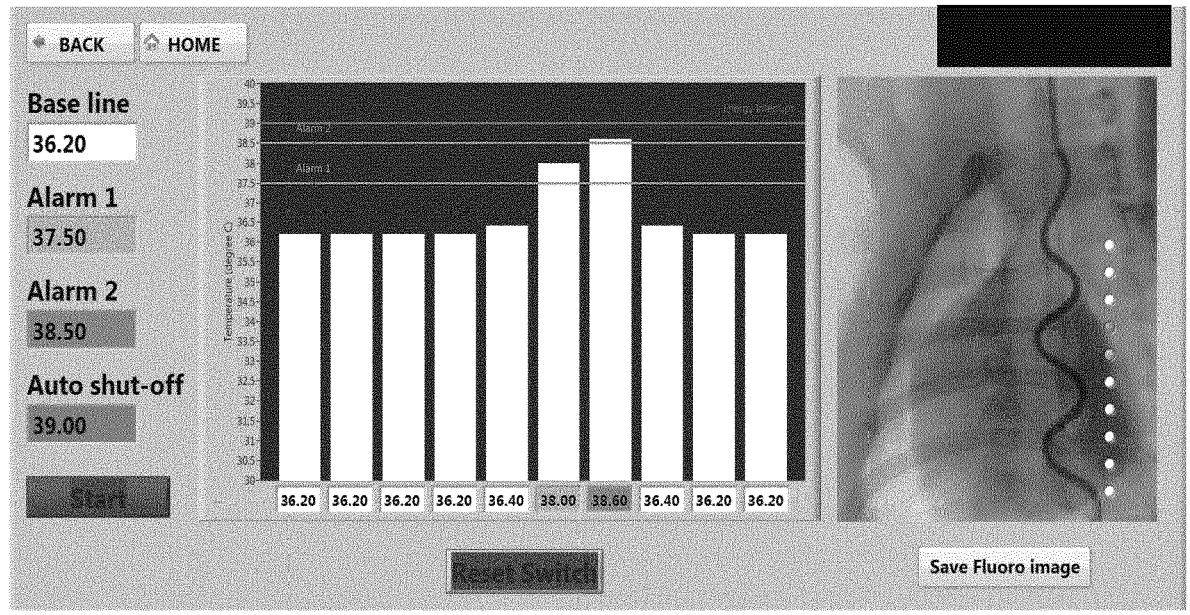
FIG. 13 is a picture of graphical unit interface (GUI) of the cardiac mapping system showing temperature readings from multiple sensors, as well as placement of multiple of the multiple sensors.

The graphical unit interphase (GUI) of applicant's cardiac mapping system of one embodiment is shown in FIG. 13. This esophageal temperature monitoring functionality and GUI is incorporated and integrated with other functions of the cardiac mapping system (or monitoring/recording system) such as "electro-anatomical mapping".

The details of esophageal probe 414, connector box 400, cardiac mapping system 402, and ablation stopping box 404 are described below.

Figure 14:
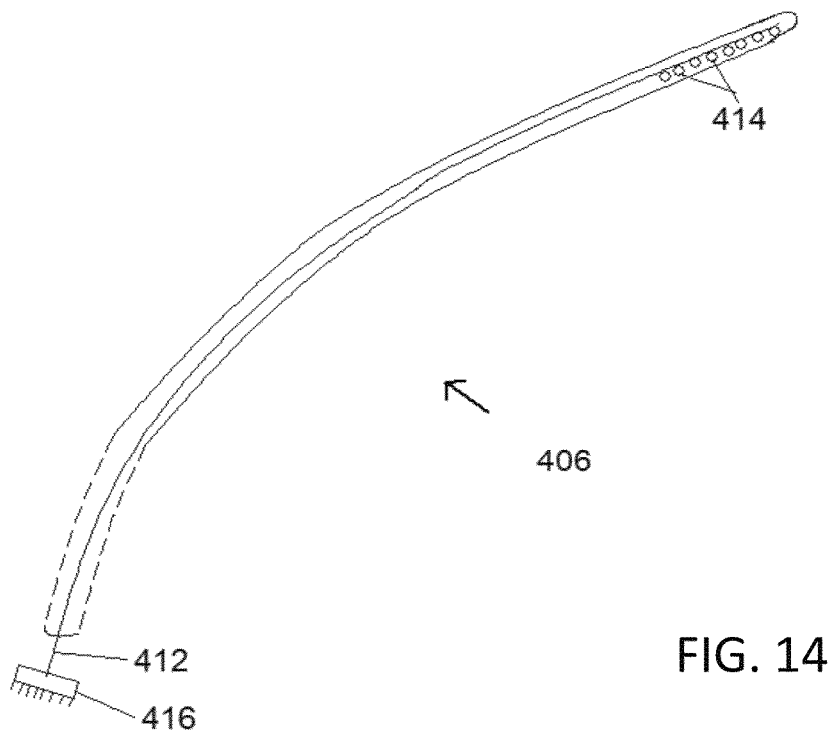
FIG. 14 is one embodiment of an esophageal probe with multiple sensors (thermistors), which is straight in shape.

In one aspect of the disclosure, any esophageal temperature probe may be used. In one embodiment, the esophageal probe may have one thermistor or thermocouple (sensor). In another embodiment, the esophageal probe may have more than one thermistors (or thermocouples). These may comprise any number of thermistors (or thermocouples). Shown in FIG. 14 is an exemplary esophageal probe 406 that may be used. This esophageal probe has a number of thermistors 414. Various thermistors have conductor wires which travel through the body of the lumen 412, and are connected to terminal connector(s) 416. The terminal connector 416 (on the proximal end) of the esophageal probe 406 connects to a connector box 400 (FIGS. 11 and 12) to get sensor information into a cardiac mapping system 402 (or cardiac monitoring/recording system 403).

Cardiac Mapping Systems

Cardiac mapping systems are well known in the art and are generally used during cardiac ablation procedure in atrial fibrillation procedures where temperature monitoring is needed.

The role of these mapping systems has been to keep a log of and make manageable and interpretable the vast amount of information obtained during an electrophysiology study. These systems have made possible the extensive intracardiac mapping that can now be performed and applied during electrophysiologic procedures. This enhanced mapping capability has been especially useful in the treatment of complex arrhythmias that require extensive ablation in the cardiac chambers, e.g., atrial fibrillation and ventricular arrhythmias.

The two of the commonly used mapping systems are CARTO (Biosense Webster) and NavX EnSite (St. Jude Medical, Inc.). CARTO uses a low-level magnetic field measured by a catheter location sensor, whereas NavX registers electrode impedance sensor in relation to skin patches that apply a low-level electrical current.

Electromagnetic Based Mapping System

Systems such as CARTO (Biosense Webster, Diamond Bar, Calif.) use the electromagnetic position of the catheter tip relative to an electromagnetic locator pad which is placed below the patient, and a reference catheter at a fixed external (usually posterior) location. The CARTO system provides electroanatomic mapping based upon the premise that an electrical current is generated when a metallic coil is placed in a magnetic field. The magnitude of the current depends on the strength of the magnetic field and the orientation of the coil in the field. The CARTO system consists of,

- a magnetic field emitter mounted under the patient; the external magnetic field emitter has 3 coils that generate ultra-low-intensity magnetic fields (between $5 \times 10^{-6}$ and $5 \times 10^{-5}$ T) that code the surrounding space with spatial information sensed by the field sensor at the tip of the mapping catheter
- a location sensor inside the mapping and ablation catheter tips, and
- a data processing unit and graphical display unit to generate and display the 3D model of the cardiac chamber of interest.

Data on the amplitude, frequency, and phase of the magnetic field are gathered and analyzed by the processing unit and displayed on the display unit. The CARTO mapping system uses a triangulation algorithm in which a sensor in the catheter tip allows the determination of its distance from each coil. In addition to the x, y, and z coordinates of the catheter tip, the CARTO mapping system can determine three orientation determinants—roll, pitch, and yaw. The position and orientation of the catheter tip can be seen on the screen and monitored in real-time as it moves within the electroanatomic model of the chamber being mapped.

Since the CARTO mapping system is not an imaging technique, fluoroscopy is initially used to establish orientation by using generally known anatomic locations in the heart as references for the later creation of the model of the mapped chamber. An electromagnetic anatomical reference patch is placed on the back of the patient and is used to track the mapping and ablation catheter. For activation mapping, an electrical reference such as an ECG signal or an intracardiac recording is used. For intracardiac recordings, coronary sinus recordings are often selected because they are usually stable. For activation, points taken by the catheter are color-coded red, orange, yellow, green, blue and purple for progressively-delayed activation areas. Similarly, the voltage map is also color-coded and superimposed on the anatomic model. Using these techniques, both the mechanism of the arrhythmia and the 3D anatomy can be created. However, creation of an electroanatomic map may be a lengthy process involving the tagging of many points, depending upon the spatial details needed to analyze a given arrhythmia. Lack of accurate ECG and respiration gating and non-real-time data are other limitations of this technique. Furthermore, the catheters used are very expensive and fluoroscopy is always used as a backup to identify the location of catheters.

Electrical Impedance Electroanatomic Mapping

The concept underlying the use of electrical impedance to calculate a spatial locations is based on the following: A very low-voltage alternating current of a particular localization frequency is applied across a patient's body using two skin electrodes confers a relatively linear voltage gradient across the tissues in the axis of the electrodes. The voltage can be detected by a sensing electrode and can then be converted to the axial location of the sensor. Three such orthogonal electric currents applied separately and detected by a sensor can thus be used to triangulate the 3-dimensional (3D) location of the sensor.

Mapping using this concept requires fulfillment of the following 4 conditions: 1) 3 orthogonal currents with the heart at the center need to be used to allow triangulation in 3-dimensional space; 2) the externally applied electric current should be easily detectable but benign to the patient and not interfere with the recorded electrograms; 3) the voltage gradient need to be calibrated to interpret recorded voltages for localization; and 4) spatial variations associated with the cardiac and respiratory cycles need to be accounted for. Thus stabilization of the whole localization apparatus throughout the mapping and ablation procedure is important to limit inaccuracies.

The EnSite NavX (St. Jude Medical, Inc. St. Paul, Minn.) was first described for electroanatomic mapping and navigation in atrial flutter ablation in 2004. A low electric current at 5.68 kHz is multiplexed with each of these pairs of electrodes to create the navigational electric field across the heart. A fixed intracardiac catheter (e.g., in the coronary sinus) or a surface electrode serves as the reference. The electrode position is averaged over 1 to 2 cardiac cycles to reduce cyclic cardiac variation. However, because of the long excursion of the respiratory cycle, eliminating respiratory variations by averaging becomes impossible without compromising the real-time localization and display.

Fluoroscopy Based Mapping System

In the method and system of fluoroscopy based mapping system, a cardiac mapping system has been disclosed where existing cardiac image or multiple images are utilized, and electrical parameter(s) information is/are superimposed on them to provide an "electro-anatomical" map. The existing cardiac image(s) may be a fluoroscope image or combined images such as a 3D computed tomography (CT) image overlaid or registered on a fluoroscope image, or other images as described later. This may also be referred to as a "sensor-less" cardiac mapping system, as the prior art systems comprise sensors that are impedance based or electromagnetic based, and the current disclosure describes a method and system that can perform electro-anatomical cardiac mapping without the impedance or electromagnetic based sensors.

Figure 22:
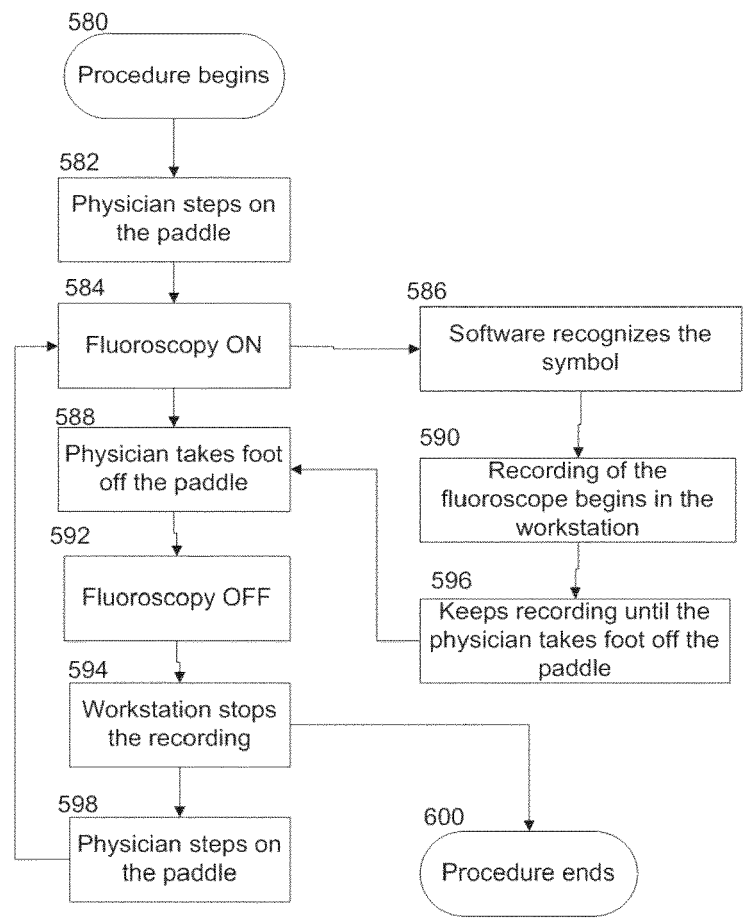

In the concept of this disclosure, a computer 68 is configured to receive multiple channels of electrical signals including 12-lead EKG and various intracardiac signals, shown in a simplified form in conjunction with FIG. 22. A computer, is generally a desktop workstation 68 (or a laptop 66—not shown) is configured to receive fluoroscopy 72 and/or other images into the computer 68. Additionally, there may be an output from the computer for feedback control of various things, for example interrupting energy delivery in certain situations. The interruption of energy delivery may be based on electrical signals and/or other parameters. One example would be interrupting energy delivery for AVNRT ablation based on timing relationships of the acquired atrial and ventricular signals. Another example would be interrupting ablation energy delivery based on esophageal temperature monitoring.

Ablation Stopping Box

Figure 23:
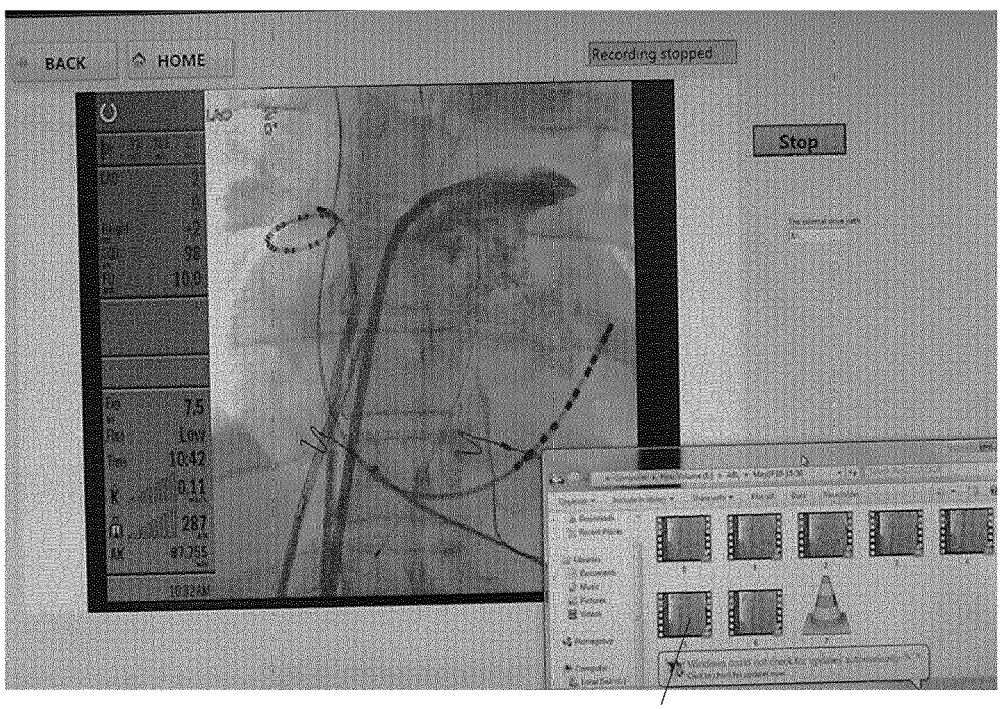
FIG. 23 shows an example of implementation of automatically recording only while the fluoroscopy is on, and saving videos in a folder.

The functioning of the stopping box is shown in conjunction with FIG. 23. The stopping box 404 is connected to the ablation catheter 84 on one end, an to the RF generator 602 on the other end. The stopping box 404 is also connected to the mapping system computer 402 (or cardiac monitoring/recording system 403). Based on meeting pre-determined criteria, selected by the physician or operator, the cardiac mapping system computer 402 sends a command signal to activate switch 606, to interrupt energy delivery to the ablation catheter 84.

In order to interrupt the RF energy delivery automatically during a procedure (based on pre-determined criteria) the system employs a stopping box 404. In one embodiment, the stopping box consists of six normally-closed DC voltage relay switches (SW1 to SW6) with 3 input/output connectors (C1 to C3).

Use with Cryoablations and Other Balloon Based Catheters

It will be clear to one skilled in the art, that the esophageal temperature monitoring system may be used for all types of atrial fibrillation ablations including radiofrequency (RF) ablations and cryoablations. In RF ablations the concern is injury due to heating. In cryoablation, the concern is injury due to cooling. In Cryoablations with cryoballoons, the temperatures are typically brought to −40° C. Potentially, the injury due to freezing could be carried over to the esophagus. In this embodiment, the alarm(s) and/or interrupt are due to reaching the limit of the decrease in temperature as opposed to increase in temperature in RF ablation. In either case, the intent is to avoid or minimize the injury to the esophagus.

Cryotherapy or use of cold temperatures to elicit a specific tissue response, has a history of effective medical use and cryoablation systems utilizing cryoballoons are also used routinely for atrial fibrillation ablations. The ultimate purpose of cryoablation is to freeze tissue in a discrete and focused fashion to destroy cells in a precisely targeted area. The application of cryothermal energy results in the formation of an ice ball. Cooling first occurs at the distal catheter tip in contact with endocardial tissue. Freezing then extends radially into the tissue, establishing a temperature gradient. The lowest temperature and fastest freezing rate are generated at the point of contact, with slower tissue cooling rates at the peripheral regions. The mechanism of tissue damage are complex and still debated, but involve freezing and thawing, hemorrhage and inflammation, replacement fibrosis, and apoptosis.

Generally in cryoablations tissue hypothermia causes cardiomyocytes to become less fluidic as metabolism slows, the ion pumps to lose transport capabilities, and the intracellular pH to become more acidic. These effects may be transient, depending on the interplay between temperature and duration. The shorter the exposure to a hypothermic insult and/or the warmer the temperature, the faster the cells recover. As a clinical correlate, this characteristic feature of cryoenergy permits functional assessment of putative ablation sites (i.e., cryomapping) without cellular destruction.

By contrast, the hallmark of permanent tissue injury induced by hypothermia is formation of ice crystal. As cells are rapidly cooled to freezing temperatures, ice crystals are first formed within the extracellular matrix, and then formed intracellularly. The size of ice crystals and their density are dependent on the combination of the following proximity to the cryoenergy source, the local tissue temperature achieved, and the rate of freezing, initially, ice crystals are formed exclusively in the extracellular space as the tissue temperature drops below −150 C. Progressive cooling to below −400 C results in the formation of intracellular ice crystals in the extracellular space results in it becoming relative hypertonic. In an attempt to reestablish osmotic equilibrium, there is a compensatory egress of water from the intracellular to the extracellular space, with subsequent cellular shrinkage, resulting in intracellular desiccation Further, the newly established osmotic gradient precipitates a diffusion gradient between extracellular and intracellular spaces, resulting in the net movement of H+ ions out of the cell, and the migration of solute ions into the cell. Concomitant increase in the intracellular saline concentration with a reduction in intracellular pH results in cellular protein damage, enzyme system impairment, and adverse effects on lipoprotein components of the plasma membrane. Of all the cytoplasmic components, the mitochondria are particularly sensitive and are the first structures to suffer irreversible damage.

Upon completion of the freezing phase, the tissue passively returns to body temperature resulting in a thawing effect. This second phase induces cellular damage through a combination of two mechanisms. First, recrystallization and coalescence of intracellular and extracellular ice crystals increase the osmotic damage and generate shear forces, which further disrupt tissue architecture. Second, restoration of microcirculatory function is associated with a hyperemic vascular response characterized by hemorrhage and inflammation (coagulation necrosis). Specifically, blood vessel walls become porous leading to increased capillary permeability and subsequent interstitial edema. This vascular congestion, combined with endothelial injury induces platelet aggregation and microthrombi formation, and culminates in vascular obliteration and ischemic cellular necrosis. As such, while the central region subjected to the coldest freezing temperature undergoes direct cellular damage, the surrounding microvascular injury results in the extension of tissue destruction.

The final phase of cryoinjury begins concurrent to thawing and is characterized by reactive inflammation, followed by tissue repair and replacement fibrosis. Over the subsequent weeks, these processes culminate in the generation of a mature lesion, which has a distinct, well-circumscribed central region of dense fibrosis surrounded by a narrow border zone of viable cellular death (due to microvacular injury and apoptosis).

Generally, a cryocatheter consists of a hollow shaft with a closed distal end containing a cooling electrode tip, integrated thermocouple deice and three proximal ring electrodes for recording and pacing. A console that contains the cryorefrigerant fluid. The cooling liquid travels through the inner delivery lumen to the catheter tip, where the cryorefrigerant is pressurized and released. This accelerated liquid-to-gas phase change results in rapid cooling of the distal tip. The gas is then conducted away from the catheter tip through a second coaxial return lumen maintained under vacuum and evacuated in the hospital medical gas disposal system.

The console allows the operator two different modes of operation. The first is the cryomapping mode in which the tip is cooled to a temperature not lower than −300 C for a maximum of 80 seconds so as to prevent irreversible tissue damage. The second mode is cryoablation, which results in cooling of the catheter tip to at least −75° C. for a programable period (nominally 4 minutes), producing the permanent lesion. The cryomapping mode can be used for an indefinite number of times before cryoablation. Cryoablation may be initiated at any time during a cryomapping application or, from the onset, if the operator wishes to forego the cryomapping function.

One of the most exciting and truly remarkable characteristics of cryothermal energy is the ability to dynamically and prospectively asses the ability to safety and efficacy of a potential ablation lesion site, because a period of reversible electrophysiologic tissue inhibition obligatorily precedes permanent tissue destruction (a process that that can be dynamically manipulated by varying the temperature and/or time of application). While extreme freezing (i.e., tissue temperature colder than −50° C.) results in near instantaneous permanent tissue injury, a functional effect may be obtained at some lethal temperatures (i.e., −10° C. to −25° C.), but complete recovery of all electrophysiologic properties and no histologically identifiable damage. Prior mapping is not theoretically possible, but the broad temperature/time window between reversible and irreversible effects renders this feature readily clinically applicable. This by identifying the desired substrate before definitive ablation, the appropriate catheter placement site may be confirm to be efficacious (i.e., efficacy cryo mapping) and/or safe i.e., safety cyro mapping). Reversible cyro mapping may be of particular importance when ablating with myogenic substrates located near critical sites such as the AV node, where images target lesion may have major consequences. Reversibility observed with cryotherapy oh energy contrasts starkly with RF energy. With RF ablations, hydrothermal tissue energy leading to reversible loss of excitability occurs at a median tissue temperature of 48° C., as reversible tissue destruction occurs at tissue temperatures greater than 50° C. The reversibility window is, therefore, too narrow for safe clinical applications.

Even though the disclosure is described primarily with cryoballoon catheter for atrial fibrillation, such as the Arctic Front® available from Medtronic. It will be clear to one skilled in the art, that other balloon catheters are also available or will soon be available. The method and system also applies to any balloon catheter for pulmonary vein isolation and/or ablation for atrial fibrillation.

One such catheter is a balloon catheter where laser energy is applied from inside the balloon, for sioating the pulmonary vein in a point-by-point type of ablation.

Another catheter being tested in clinical trials, also applies energy though the balloon for "single shot" pulmonary vein isolation, but heats up the tissue instead of freezing the tissue as with cryoballoon catheter.

The method and system described in this disclosure can also be used for any balloon based catheter utilized for atrial fibrillation ablations, and is considered within the scope of this invention.

Medical Images (Including 3-D Images) Based Mapping System for Balloon Based Catheter Ablations In the mapping system of this disclosure, various medical images and various cardiac signals are brought into the mapping system.

Figure 15:
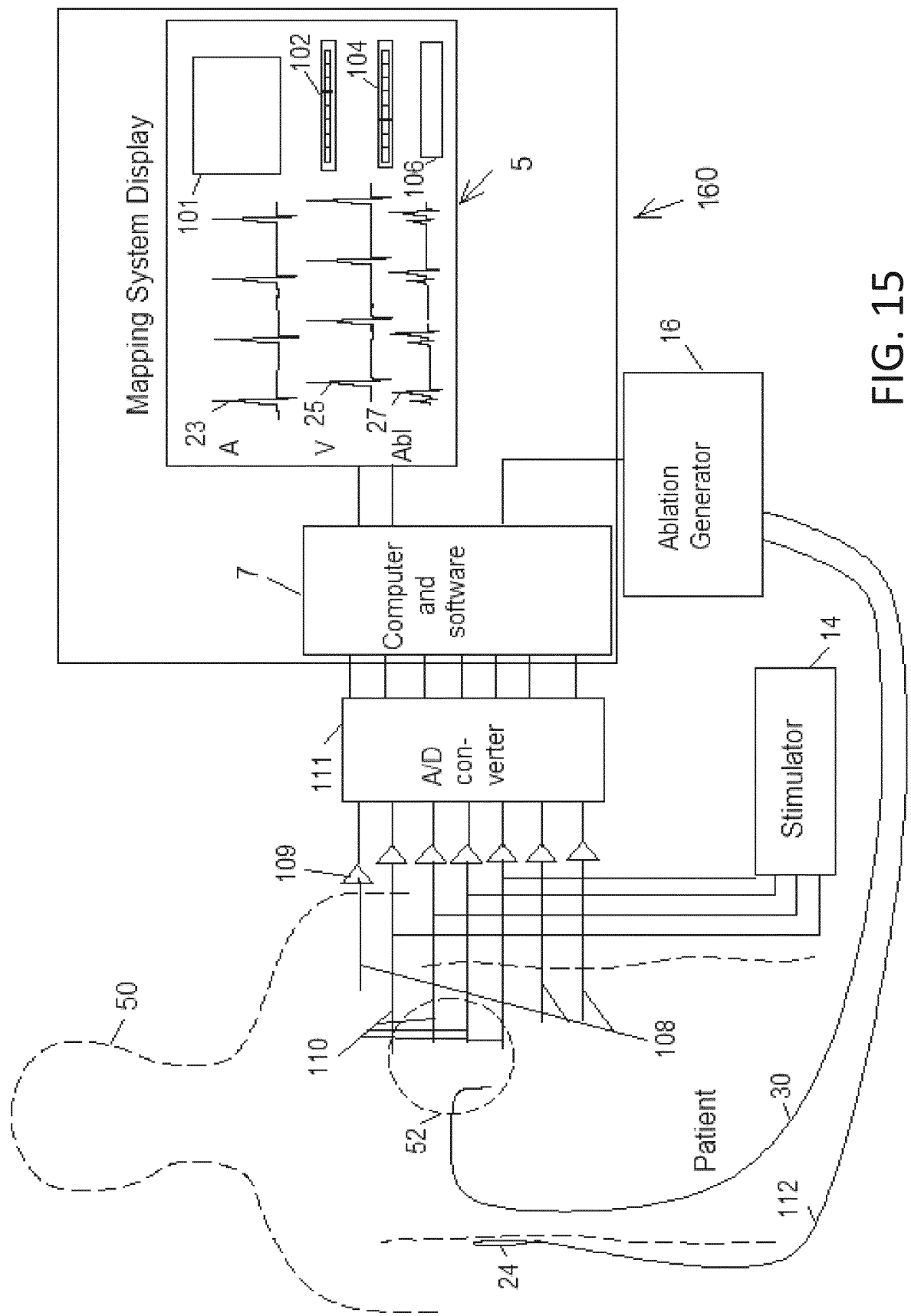
FIG. 15 is a schematic diagram showing acquiring intra-cardiac signals from a patient.
Figure 16:
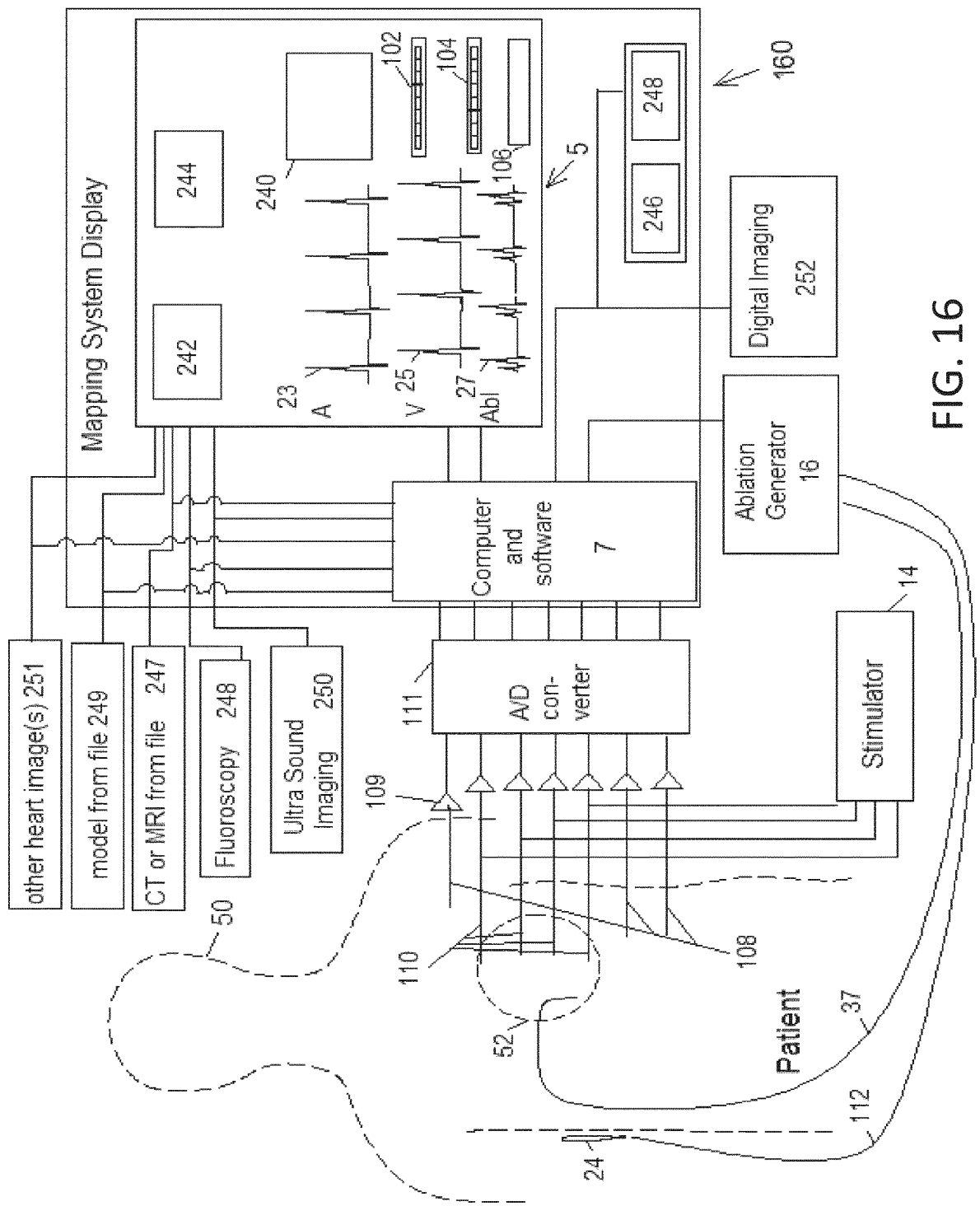
FIG. 16 is a schematic diagram showing acquiring intra-cardiac signals and medical images from a patient.

The signals acquisition and system setup is summarized and shown in conjunction with FIG. 15 and FIG. 16. The acquisition of signals from a patient 50 into the medical images based mapping system 160 of this disclosure are shown in conjunction with FIG. 15.

As shown in FIG. 15, cables 108 from body surface electrodes, and cables 110 carrying intracardiac signals from the heart 52 are amplified, filtered 109 via A/D converter 111, and brought into the computer 7 of the mapping system 160. The computer 7 of the mapping system 160 also comprises algorithm(s)/program(s) which are configured for data analysis and processing which is used for guiding the ablation procedure with the mapping system 160. The signals from the computer 7 of the mapping system are displayed on a monitor shown in FIG. 15 as mapping system display 5. The mapping system computer 7 also interfaces with the ablation generator 16, and stimulator 14 for pacing.

It will be clear to one skilled in the art that the computer 7 can be a desktop computer, a server, a laptop computer, or a tablet such as an I-Pad. It could also be a mobile device that has sufficient computing power.

In one aspect of the disclosure, one or more imaging display(s) may be added to the display of the mapping system display. As shown in FIG. 16, examples of these displays without limitation includes ultrasound imaging of the heart 250, 2D ICE 250 (4D ICE not shown), fluoroscopic image 248 of the heart, detailed digital image of the heart such as CT 247 or MRI. Having one or more image modalities of the heart in addition to the electrical signals is advantageous, since detailed anatomical position in addition to electrical activation or timing information is useful for making decision about the ablation site. It will be clear to one skilled in the art that detailed anatomical imaging information such as available from GE Corporation, Siemens, Philips, Toshiba or Hitachi can be brought in the mapping system display, as an aid for selecting the site for ablation. The acquiring of images into mapping system 160 involves different types of input devices. The images brought in include real-time images and stored images. Real-time images like fluoroscopy can be brought into the mapping system utilizing boards configured for bring in medical images. These boards are available from several vendors and are well known to one skilled in the art. Real-time ICE images may also be brought into the mapping system via the output ports of the original ICE equipment. Stored images, for example CT image is generally on compact disk (CD) or DVD. Therefore the CT image is brought into the mapping system 160 via a digital file. Other images such as fluoroscopy may be brought into the mapping system 160, as an analog signal or brought in digitally.

It will be clear to one skilled in the art that various different software programs may be used to code these algorithm(s)/program(s), of this disclosure. Program code can be written using one of several commercially available software packages. The software that can be used for this purpose includes, but is not limited to Lab Windows/CVI, LabView (National Instruments Corp.), C, Microsoft Visual C++, Dot Net framework, MATLAB, and Microsoft Visual Basic, Phython among others. Use of these or other functional languages for this purpose that are available now or developed in the future, is considered within the scope of the disclosure. Testing of applicant's prototype and various aspects have been performed utilizing Microsoft visual C++, LabView and MATLAB.

In coding and configuring the software, the electrical signal reference timing can be taken (T=0) from the point of signal detection in the CS and ABL catheter. Signal detection can be from simple threshold detection to more sophisticated peak detection algorithms, as long as it consistent to both CS (or HRA) and ABL signals. The formulas for line coding in C++ or VI's in Labview are well known to one of ordinary skill in the art.

In the method and system of this disclosure, medical images instead of computer models are utilized for "electro anatomical mapping" and guide for ablation. Among the images utilized, without limitation, include, Two dimensional (2D) intracardiac echo (ICE) images
Three dimensional (3D) intracardiac echo (ICE) images
Four dimensional (4D) intracardiac echo (ICE) images
Fluoroscopy images
Fluoroscopy images that are overlaid
CT (computed tomography) image(s)
Fluoroscopy and CT based images, which may be overlaid or be side-by-side,
ICE and fluoroscopy based images
MRI (magnetic resonance imaging)

In one aspect of this disclosure, Intacardiac Echo images are utilized for mapping and ablation. In the methodology, ICE images are brought into the mapping system computer workstation, along with the intracardiac electrical signals and surface EKG electrical signals. The software is configured and programmed such that the mapping and ablation tags are placed on the ICE (intracardiac echo) images. The ICE images may be brought into the mapping system computer (workstation) via specialized boards installed in the workstation. One such board is available from Bitflow corporation. Alternatively, the ICE images may also be configured and brought into the workstation via the output ports of the ICE machine. In this case, the input into the workstation may be via USB ports.

It will be clear to one skilled in the art that the electrical signal sources 94 may be body surface signals such as 12-lead EKG, and/or intracardiac signals and/or other sensor signals, for example temperature. For the purposes of this disclosure, the image(s) source may be one or any combination of image sources shown in conjunction with FIG. 17.

Figure 17:
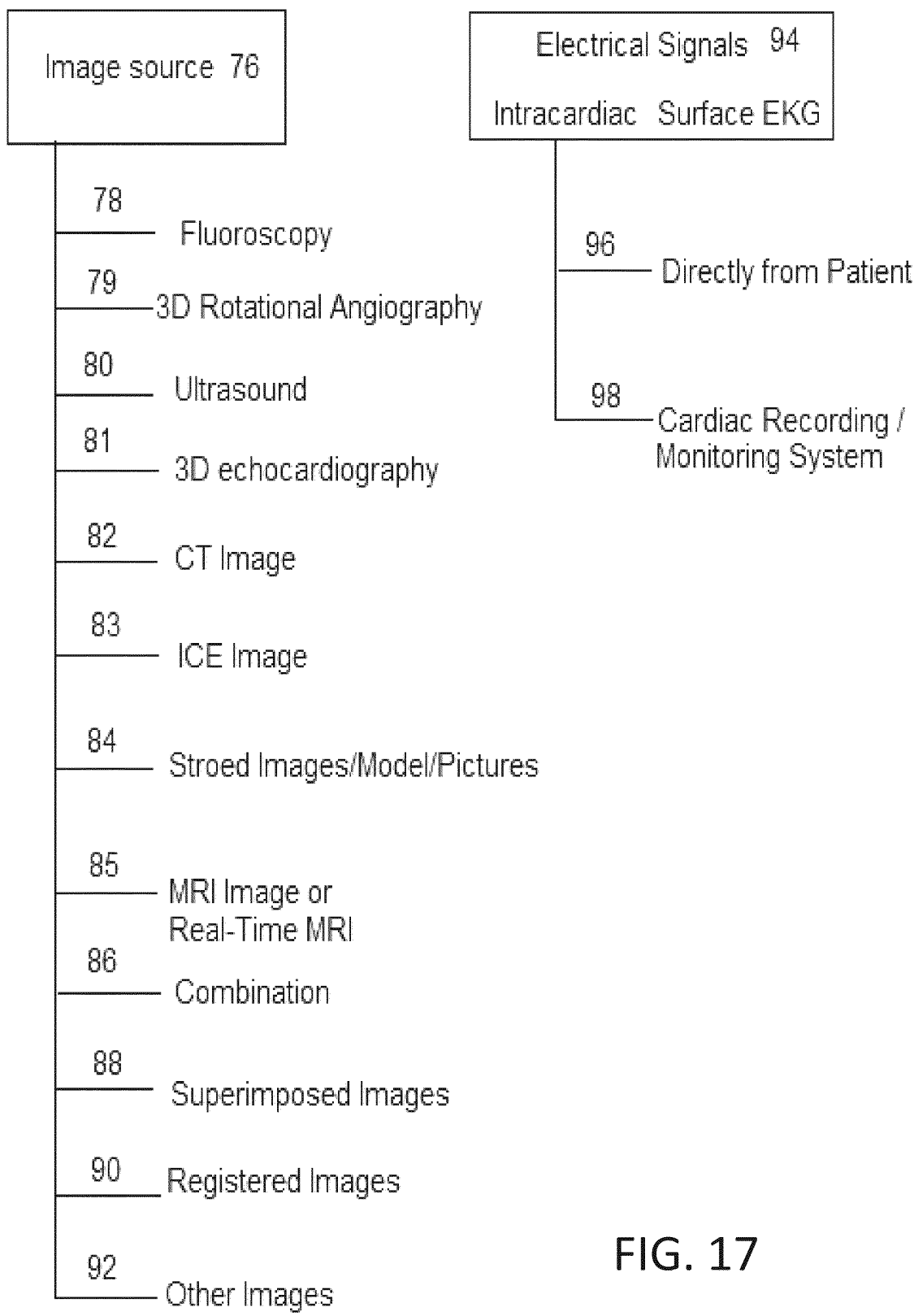
FIG. 17 is a diagram showing different type of images that are acquired for mapping, as well as, electrical signals acquired from a patient.

As shown in FIG. 17, medical imaging signals can be obtained from a variety of sources and imaging modalities, and can be combined with an overlap or side-by-side. Also shown in conjunction with FIG. 17, in one preferred aspect of the disclosure, the image source(s) 76 may be fluoroscopy 78. Conventional fluoroscopy is the main imaging technology used for intracardiac device manipulation in a variety of interventional cardiovascular procedures, including electrophysiological (EP) studies. X-ray fluoroscopy is a continuous or dynamic imaging technique, where moving images of the patient can be seen in real time. An X-Ray beam is passed through the body, and the image is transmitted to a monitor so the movement of a body part can be seen in detail. The acquisition of digital fluoroscopic images can be combined with injection of contrast material to give an enhanced image. Fluoroscopy has major clinical advantages, such as its wide-scope in cardiology applications (catheter manipulation, cardiac motion, and an in-plane resolution similar to ultrasound). However, as in X-Ray modalities, Fluoroscopy is invasive due to its X-ray radiation, and injecting contrast materials could increase radiation. Therefore, reducing the procedural time is highly desired.

X-Ray modalities such as fluoroscopy and computed tomography (CT) rely on X-rays to penetrate objects. Objects with higher densities attenuate X-rays in different manners, and these cast an X-ray shadow of the radiopaque tissues (such as bone) on a fluorescent screen. In its original development, fluoroscopic images were seen with film. Now, electronic sensors convert X-Ray energy into electrical signals, which are then stored digitally. Within the computer receiver, multiple sequential fluoroscopic images produce real-time fluoroscope videos.

X-ray fluoroscopy can be combined with 3D mapping systems to aid in catheter manipulation. Electromagnetic fields are typically used to place the catheter in 3D space. The 3D position and orientation of the catheter tip is transferred to the fluoroscopy system and visualized in a virtual view projected on cine loops recorded at the beginning of the procedure. The cine loops play continuously and are ECG-gated to ensure that the movement of the virtual catheter tip and the previously recorded cine loop remain synchronized.

For the purposes of this disclosure, the fluoroscopy may be single plane or biplane fluoroscopy. Biplane fluoroscopy has the additional advantage to present another additional orthogonal view. Biplane fluoroscopy is similar to X-ray tomography in that it provides more views, and the multiple views showing rea-time cardiac movements aid in catheter placement and localizing structures in the heart.

In one aspect, the image source may be 3D rotational angiography 79. Rotational angiography is one of the latest angiographic modalities to map various cardiac chambers and the coronary venous tree anatomy. Without compromising the clinical utility of images, it requires both less contrast agent and less radiation dose. Rotational angiography produces CT-like 3D volumes during catheter intervention using a fixed C-Arm. The C-Arm rotates around the patient and acquires a series of X-ray images that are then reconstructed through software algorithms into a 3D image. Rotation takes between 5-20 seconds, acquiring hundreds of 2D images, and 3D reconstruction then follows. Contrast agents are sometimes administered to enhance certain structures or to reflect pulmonary transition time. Image integration is optionally done between 3D reconstructions and fluoroscopic videos during ablation. The benefit of rotational angiography to produce the 3D image overlays is that these are performed intraprocedural, removing the need for image registration which could lead to millimetric mis-registrations. Additionally, rotational angiography can be integrated with electroanatomical mappings to improve outcome relative to MRI 3D reconstruction integration to such maps.

In one aspect, the image source may be ultrasound 80. Ultrasound imaging uses sound waves and frequency-encoding to produce high-resolution and non-invasive images. The central principle of ultrasound imaging is that sound waves that are not absorbed by the body are reflected back. The ultrasound transducer that emits ultrasound waves also detects returning waves. The time between emission and detection encode distance. Generally, higher frequencies (shorter wavelengths) allow improved resolution of small structures, whereas lower frequencies allow for improved detection of deeper structures. In the field of cardiology, echocardiograms are able to produce 2D, 3D, and Doppler ultrasound images. Other echocardiographic modalities may include real-time 3-D echocardiography (3D echo), four dimensional (4D) echocardiography, strain and strain rate imaging, as well as speckle tracking. The use of ultrasound in cardiology has greatly expanded the understanding of patient specific anatomy, physiology and assessment of therapeutic interventions such as ablative procedures and cardiac resynchronization therapy (CRT).

The most common echo imaging in cardiology is real-time 2D imaging. The most common cross-sectional views—parasternal long axis, parasternal short axis, and the apical view—along with real-time imaging, allow for detecting abnormal anatomy or abnormal movement of structures. Generally, echocardiography provides improved accuracy and reproducibility over 2-D map thirds for left ventricular (LV) volume and function and detail cardiac structures. Tagging and/or tracking the LV surface in real-time may provide new approaches to quantifying myocardial mechanics, such as regional shape and strain. Color-flow mapping (CFM) uses Doppler technology and allows for the measurements of blood flow velocity and direction which is then color-coded and superimposed on a section of a 2D image. In this technique, blood flow changes the frequency of the emitted ultrasound wave. This information, along with the timing, can encode for distance and direction of flow, which is color-coded on the flow map.

In one aspect, the image source may be 3D echocardiography 81 which allows imaging and analysis of cardiovascular structures as they move in time and space, thus creating possibility for creation of four-dimensional (4D) data sets (i.e., 3D and real time). Advances in computer and transducer technologies, especially the fully-sampled matrix array transducer, have permitted real-time 3D image acquisition and display. Generally, real-time 3-D TEE-rendered visualization of the left atrium (LA) and pulmonary veins (TVs) provides unparalleled anatomic and functional information that will find additional application in clinical and surgical decision-making. The application of real-time 3-D echo in CRT, stress echocardiography, myocardial perfusion imaging and write hard evaluation are all evolving rapidly and are potential for tall grounds for translational research. The novel technology of 3-D speckle tracking, which makes possible the extension of robust strain-derived information to 3-D, has application in a variety of conditions. Real-time 3-D echo also opens exciting avenues by allowing custom-made 4D applications, which added dimension of time to existing 3-D data sets. 3D echo has great potential and will compliment and likely compare favorably with the quantitative ability of cardiac MRI (discussed later). The superior temporal resolution of echocardiography offers unique advantages for this purpose. Combining the greater temporal resolution of 3-D echo with the excellent spatial resolution of MRI (or CT) may yield imaging data set with unsurpassed anatomic and physiological information, an approach called "fusion imaging".

In one aspect of this disclosure, intracardiac echocardiography (ICE) images are utilized for mapping and ablation. The physics of ICE are similar than those used for ultrasound applications: sound wave reflect and refract differently according to the properties of tissue boundaries, and their timing and frequency information can be encoded into B and M-mode, and Doppler images. In this modality, a catheter is the source of the ultrasound waves, and the cardiologist is able to control the positioning and orientation, rather than a sonographer in transesophageal echo. This approach can also be maneuvered within the heart, allowing for visualization of cardiac structures and blood flow, and close-up views. The accurate imaging of the particular pathology, its anatomic features, and relative spatial relation to the surrounding structures aids in catheter and wire positioning, and the application can be done without anesthesia or radiation. Main interventional procedures performed with ICE systems include transseptal puncture, intraarterial defect closure, percutaneous valvular implantation, lead extraction, and ablation of complex arrhythmias.

In ablating complex arrhythmias, ICE has had a major impact on identifying and targeting arrhythmic substrates, and can be augmented by using other imaging techniques such as electroanatomical mapping. The unique feature of ICE in ablation is that it provides information about the contact between the mapping/ablating catheter and the myocardial tissue. It can also guide the catheters in complex anatomic settings, especially when accessing the LA through transseptally. Real-time information can also be obtained, providing precise visualization of the mapping/ablating catheter position relative to the particular structures.

In the methodology of this disclosure, ICE images are brought into the mapping system computer workstation, along with the intracardiac electrical signals and surface EKG electrical signals. The software is configured and programmed such that the mapping and ablation tags are placed on the ICE (intracardiac echo) images. The ICE images may be brought into the mapping system computer (workstation) via specialized boards installed in the workstation. One such board is available from Bitflow corporation. Alternatively, the ICE images may also be configured and brought into the workstation via the output ports of the ICE machine. In this case, the input into the workstation may be via USB ports.

In one aspect, the image source may be 2D intracardiac echocardiography (ICE) 83. Generally, the new integration software module emerge from the marriage of the phased array intracardiac echo cardiac graffiti catheter (AcuNav diagnostic ultrasound catheter, at least on Siemens, Mountain View Calif., USA) with a special sensor of electromagnetic field that is used in the catheters for electro-anatomical mapping. It enables semi-automatic tracing of the current contours of the chamber of interest in different planes, and subsequent addition of these contour points into the 3-D electro-anatomical map. In this way, a 3-D electro-anatomical map of the LA or the left ventricle (LV) could be constructed from a series of images obtained with intracardiac echocardiography catheter within the right atrium or right ventricle or even within the LA through a transeptal puncture, without increasing complications or procedural duration. This enables fluoroscopy exposure and mapping times to be reduced. This technique has also been used to identify LV scar and border zones during ablations of VT. Generally, the echocardiography images are gated to the atrial electrogram on the reference catheter.

In one aspect of this disclosure, the image source may be 3D intracardiac echocardiography (ICE) 81. 2D ICE only provides a slice through an individual pulmonary vein ostium, which makes it difficult to assess true anatomic extent in 3D space, and obtaining 3D ICE anatomical images could reduce procedure time. 3D ICE has been used in imaging the esophagus as a complementary tool to 2D ICE during ablation procedures. The Sequoia ultrasound system (Siemens Medical Solutions) is equipped with SoundStar® 3D diagnostic ultrasound catheter. Similar to 2D procedures, the catheter is inserted into the femoral vein and advanced into the right atrium. ICE imaging assists transseptal catheterization and positioning of the mapping/ablation catheter at the pulmonary vein ostia. This system also measures ostial blood flow before and after ablating lesions. 3D ICE provides complemental information to 2D ICE in that it can include additional anatomical detail and accurate spatial location of the lumen anterior and posterior wall (LAPW), which can aid in locating structures such as the esophagus. 2D ICE can also provide this information; however it requires 3D reconstruction, adding time to the procedure.

There are three strategies of 3D reconstruction in ICE. As described above, one of them marries the phase-array Ice catheter with a special sensor of electromagnetic field that is used in catheters for electroanatomical mapping. In this way, 3D electroanatomical map reconstruction can be achieved from a series of images obtained with ICE catheter. Reconstructions vary as a function of manual tracings with the ICE catheter, but merging these reconstructions with CT or MR angiography could improve construction. Another strategy mediates the aforementioned problem by using a special pull-back device that uses a stepping motor to move the Ice catheter linearly in the cranio-caudal direction. A third approach uses a motor to obtain a 3D reconstruction during rotational scanning using a conventional based-array ICE catheter. The latter two use cardiac gating and electroanatomical data can be overlaid on these images as well.

In one aspect of this disclosure, the image source may be 4D ICE. This is also known as real-time 3D ICE. Cardiac resynchronization therapy is an application that typically indicates 4D ICE. In this approach, 3D anatomy is imaged in time, allowing for complex imaging showing complex wall motion pattern. 4D ICE can offer the potential to identify dyssynchrony, in addition to the optimum placing site that would result in resynchronization. Real-time 3D ICE is accomplished using transducers with a matrix array that generates a pyramidal burst of ultrasound (some consisting of more than 3,600 transducers). An advantage of this method over 2D ICE is avoiding any assumption of ventricular mass and volume, in addition to rapid acquisition time compared to other imaging modalities. In ablation procedures, 4D ICE can aid in placement, relying on the advantages of 3D ICE in addition to characterizing the pattern of atrial flutter based on real-time motion.

In one aspect of this disclosure, the image source may be 5D ICE. In this implementation, real-time, 3-dimensional images are combined with intracardial electrical signal sources, producing an information-rich display of cardiac. It will be clear to one skilled in the art that the electrical signal sources 94 may be body surface signals such as 12-lead EKG, and/or intracardiac signals and/or other sensor signals, for example temperature. For the purposes of this disclosure, the image(s) source may be one or any combination of image sources shown in conjunction with FIG. 17.

In one aspect, the image source may be cardiac tomography (CT) 82. Because of its high resolution and fast acquisition, CT plays a great role in interventional electrophysiology. Generally, it is commonly used in patients undergoing AF ablations, contrast enhanced CT images provide accurate visual isolation of the LA, pulmonary veins and surrounding structures. This allows for pre procedure assessment of important anatomic variants, such as ectopic or anomalous veins, as well as the relationship of the esophagus to the posterior LA. Post procedure monitoring for complications of AF ablation, namely pulmonary vein stenosis, is mainly done with CT. A major disadvantage of CT is exposure to ionizing radiation. Another limitation in general is that the images are not usually acquired at the same time as the procedure. This limitation is circumvented, however, by using intraoperative/intraprocedural combined CT and rotational angiography.

In one aspect, the image may be cardiac computed tomography (CCT). CCT provides similar diagnostic accuracy to direct angiography. Generally, the role of multi-slice CT in mapping and ablation of cardiac arrhythmias is well-established and it is the most commonly used modality that is integrated with electro-anatomical map (EAM). CCT is quite useful for pre-procedure evaluation of left atrium (LA) and pulmonary vein (PV) anatomy; it provides a 3-D endocardial view of intracardiac structures with accurate measurement of target areas such as LA and PV. The current system provides a navigator view. CCT also provides assessment of myocardial mass, LV volume, coronary and pulmonary arteries and epicardial views. CCT can also be integrated with fluoroscopy. Both EAM and CCT are useful in detecting scar tissue. CT is able to re-create a real cardiac chamber in a short amount of time with great detail, such as LA and PVs. Recent advances in multi-detector technology have led to improvement in spatial and temporal resolution, allowing coronary artery imaging and gated Cine imaging to evaluate ventricular function.

In one aspect, the image source may be Magnetic resonance imaging (MRI) 85. The role of MRI is rapidly expanding in interventional electrophysiology in a similar fashion to CT. Because of its high resolution, the anatomic detail is superior with MRI. One of the advantages is the lack of ionizing radiation or iodinated contrast agent. Its main role is the range integration for AF ablation. Additionally, MRI plays an increasing role in the perioperative assessment of LA ablation lesion contiguity and transmurality, as well as in the ablation of structural heart-disease related VT. Pre-procedure imaging in a small group of patients with non-ischemic cardiomyopathy has shown strong correlation both quantitatively and qualitatively between MRI-identified myocardial scar and electro-anatomical definitions of scar. This pre-procedure data is used to help plan ablation strategies, such as a primary epicardial approach in selected patients with non-ischemic LV cardiomyopathy. The main limitation of MRI is in cardiac patients with pacemakers or defibrillators.

MR images are produced noninvasively using strong magnetic fields that align hydrogen protons to the main magnetic field axis. These protons precess about the main magnetic field at a frequency proportional to the field. Radio-frequency pulses set to that frequency tips the protons to a transverse plane. The rate at which the proton spins return to the main magnetic field direction is a function of the tissue properties and that time is measured using radio-frequency coils. MR images have similar spatial resolution to CT; however, the soft-tissue contrast in MRI is superior to that in CT. A technical drawback to MRI is the length of time required to create 3D images.

In one aspect of the disclosure, real-time MRI systems for the use during electrophysiology studies may be used. A real-time MRI system will allow visual isolation and remote navigation of catheters within the heart and potentially enable imaging of ablation lesions while they are being generated. This method provides excellent soft tissue characterization in a true 3D anatomical and temporal model, allowing for lesion development during ablation procedures. Additionally, real-time MRI can identify gaps in ablation lines, improving procedure outcome. The method could enhance fluoroscopy images, or even eliminate the use, thereby reducing the amount of ionizing radiation to the patient. Similar to fluoroscopy and rotational angiography, real-time MRI can be gated to the cardiac cycle, thus allowing for electroanatomical mappings.

In one aspect, the image may be Positron emission tomography. Ablation strategies for non-idiopathic VT are increasingly based on anatomic information of the scar and its border zone. The current "gold standard" for voltage mapping is limited by its inability to accurately describe complex 3-D scar morphology, it's in perfect spatial resolution and prolonged procedure times. Positron emission tomography (PET) generally plays a pivotal role in overcoming these limitations. Originally developed as an assessment of myocardial viability, hybrid scanning with F-fluorodeoxyglucose PET and CT allows for the display of a single image set with both detailed anatomic and metabolic information. These images can be integrated with the electro-anatomical maps (EAM) during ablation of VT, in a similar manner to traditional CT or MRI. PET-CT is also capable of imaging surviving regions within ventricular scar in patients with structural heart disease and VT. These regions often serve as critical isthmuses for scar related VT. The detection of critical components of the reentrant substrate prior to LV mapping may allow for more efficient substrate-based ablation.

It will be clear to one skilled in the art that the medical image or images utilized for the practice of current disclosure may also be stored images or models or pictures 84, certain image combinations 86, superimposed images 88, registered images 90, or other images 92. Any combination of image sources may be used for the practice of this disclosure. Many forms of above image technology alone or in combination is used.

In one embodiment of this disclosure, a mapping system is disclosed which bypasses the need for an electrical impedance and/or magnetic sensor for creating geometry and wherein electrical parameter information (both measured and calculated) is/are superimposed and displayed on the existing medical images. Superimposition of electrical parameter information may also be displayed on images that are overlain on top of each other or on fused images. One example of such superimposition of electrical information is shown on fluoroscope image information by way of example. It is to be made clear that such superimposition of electrical information may be on a 3D rendering such as rotational angiography or CT scan which can be rotated around any axis. It may also be on a combination of images that are registered and overlaid on top of each other, which is considered within the scope of the invention. In one aspect, such superimposition of information is on structure that can be rotated around any axis.

The mapping system of the current disclosure is designed to facilitate the balloon based catheter ablation procedure by providing an actual patient's cardiac image based mapping system, as opposed to sensor based geometry on a computer model. These medical images may include any combination of images including Fluoroscopy, Ultrasound, Intra-cardiac Echo (ICE), Computed Tomography (CT), Magnetic Resonance Image (MRI) or any other type of medical images. A combination of medical images may also be used for example a combination of fluoroscopy and ICE may be used, or any other combination of medical images may be used. The general concept of the mapping system is shown in conjunction with FIGS. 1A, 1B, 1C and 18.

In one aspect of the system and method, live fluoroscopy 558 images are brought into the computer workstation of the Mapping System 550. Several computer boards are available for this purpose and are well known in the art. Also, as shown in FIG. 15, electrical signals 566 of the patient including both surface and intracardiac are brought into the computer 550 of the mapping system.

Figure 18:
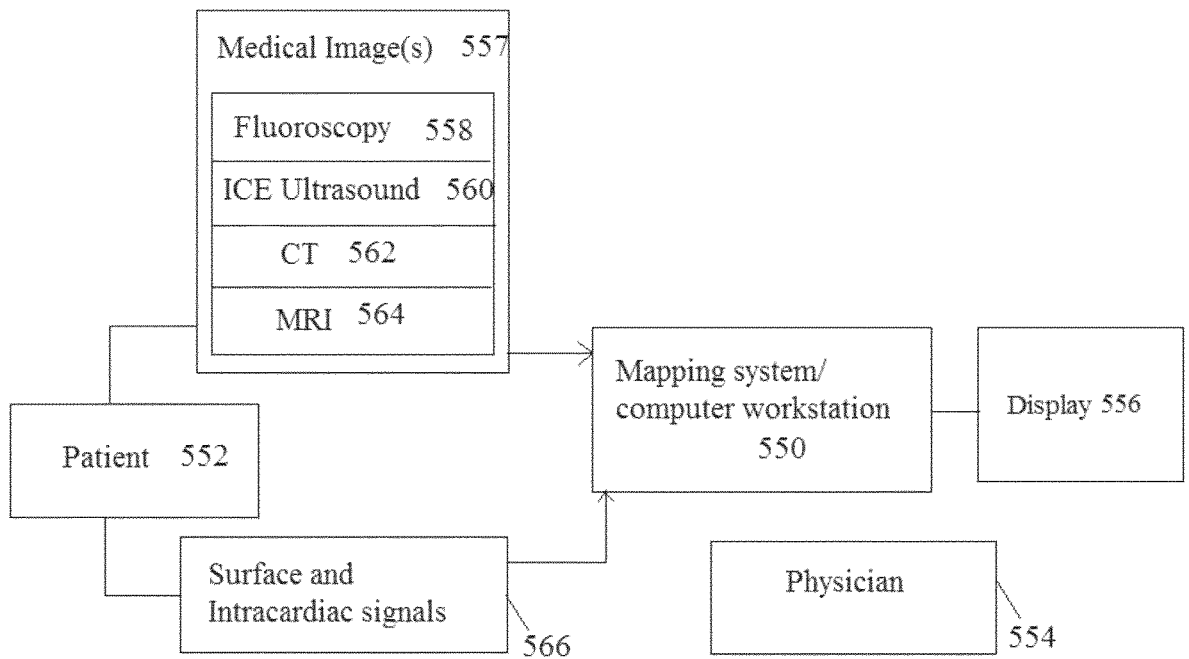
FIG. 18 is a generalized block diagram showing fluoroscopy or medical images based cardiac mapping system for cryoballoon ablations or for radiofrequency (RF) ablations.

As shown in FIG. 18, Intracardiac Echo (ICE) 560, computed tomography (CT) 562, Magnetic Resonance Imaging (MRI) 564 may also be used. Additionally, a combination of images may be used. For example, cryoballoon (or any other balloon catheter for atrial fibrillation procedures) may be localized both on fluoroscopic 558 and ultrasound (ICE) 560 images. Further, the fluoroscope and ICE images may be registered to each other in method and system of the current disclosure.

Figure 19:
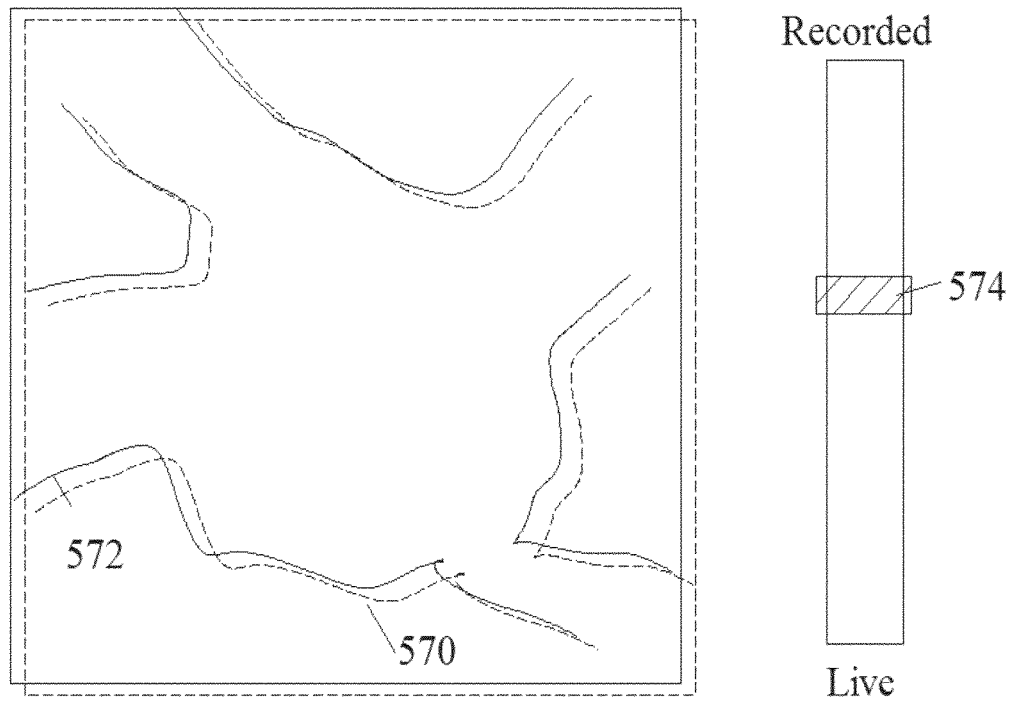
FIG. 19 depicts a live image and recorded image superimposed on each other with a way to adjust the transparency factor between the live and recorded image.
Figure 20:
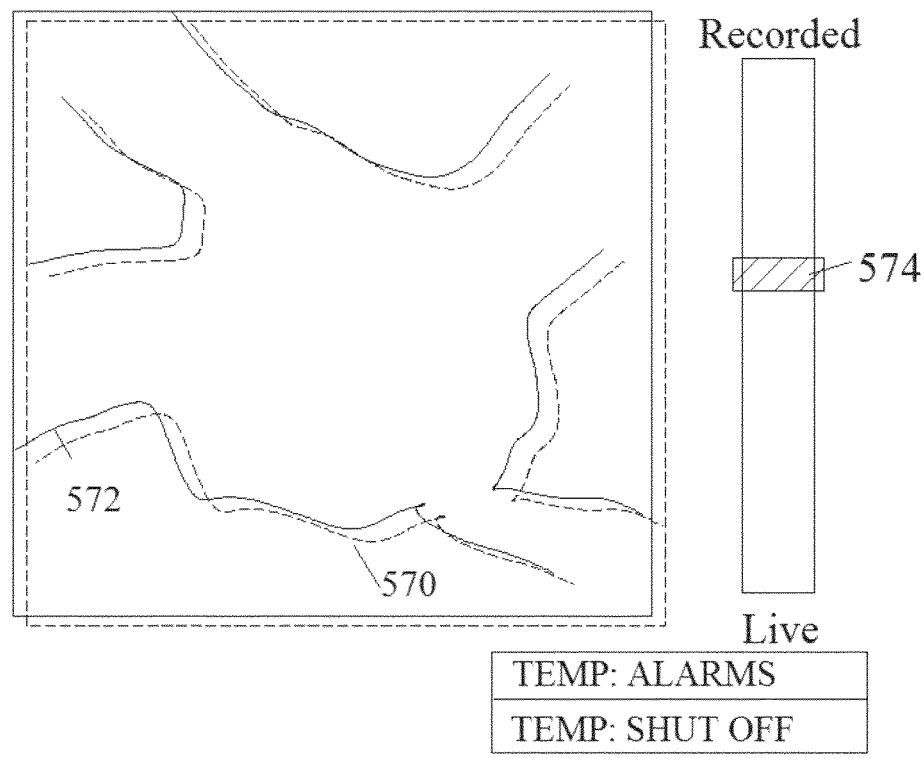
FIG. 20 depicts a live image and recorded image superimposed on each other with a way to adjust the transparency factor between the live and recorded image with temperature module interface.

In one preferred embodiment, shown in conjunction with FIGS. 19 and 20, a high resolution, high clarity image, i.e. with contrast medium or "dye" injection is recorded. These images will generally be recorded with a rotation of the fluoroscope. The advantage of rotation is that it provides 3-dimensional (3D) information. Additional recordings without rotation may also be recorded in one view such as an AP view or any other view.

Generally, in fluoroscopy high image quality is obtained by increasing radiation dose level. In the typical workflow of the method, highest resolution setting (Cine loop—30 frames/sec) is used for the recording. In addition, a contrast medium or "dye" is injected for the recording. The combination of highest exposure and contrast medium injection provides a high quality image which clearly delineates the left atrium (LA) and pulmonary vein(s) anatomy. The high resolution recording will generally be very brief so the patient is exposed to the high radiation level for only less than 10 seconds, more typically 5 seconds or less. For the purposes of injecting contrast medium or "dye" injection, a pump is preferably utilized but is not essential, as the injection may also be done by hand. In another aspect, less than the highest radiation level may also be utilized, based on the discretion of the physician and is within the scope of this disclosure.

Figure 21:
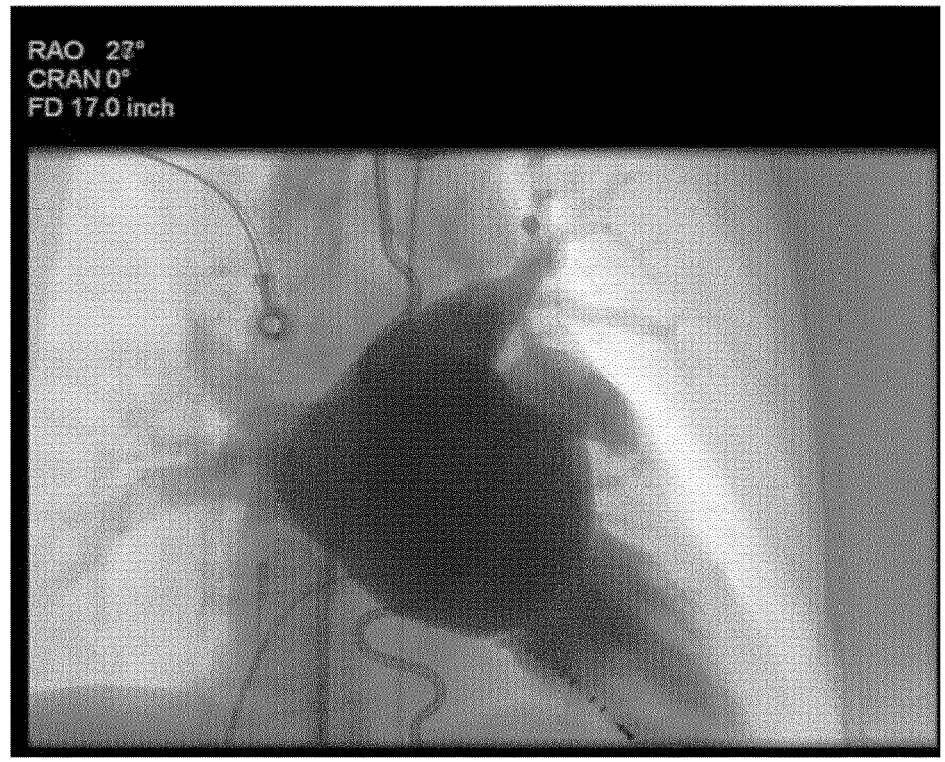
FIG. 21 shows an example of a recorded high resolution image of the left atrium recorded with "dye" injection.

Therefore in the first step, at the maximum 30 frames/sec (cine loop) resolution, a "dye" injection is performed and a rotation is recorded in the mapping system. This rotation will generally show a clear outline of the left atrium and the pulmonary veins at different angles. One example of a high resolution image is shown in FIG. 21.

There is a general need for a method and system to automatically record a procedure which utilizing fluoroscopy and with a computer based system, for the recording to occur only when the physician pushes the pedal and the fluoroscope (or radiation) is ON. Further, automatically stopping the recording when the physician takes the foot off the pedal, and the fluoroscope is turned OFF.

This is true for any situations where it is desirable to record the fluoroscopy from a procedure. This has application for any cases that require fluoroscopy in the fields of cardiac electrophysiology, interventional cardiology, or any fields of medicine that require fluoroscopy for a medical procedure. One application of this is in the current application, but the method and system can be used for any application or procedure requiring fluoroscopy.

In the method and system of this disclosure, for the current application more than one recording is generally made from the fluoroscope in the beginning part of the procedure. In one aspect of this disclosure, the software is configured and programmed such that the recordings from the fluoroscopy may be activated manually, or the ON-OFF switching process for the fluoroscopic recordings may be automated via the software utilizing optical character recognition (OCR).

In the manual portion of the software coding, a software button may be programmed and configured such that an operator starts the recording from the fluoroscope while the physician has activated the fluoroscope (generally by pressing a foot paddle). Similarly the operator stops the recording after the physician has taken the foot off the paddle.

Since this method is very inefficient and for many types of procedures it is not practical, it is highly desirable to program and configure the software such that the recording automatically starts when the physician pushes the paddle, and the fluoroscope is ON. Similarly in this methodology, the computer automatically stops recording when the physician takes the foot off the paddle. Generally, the fluoroscope is ON only when the physician has the foot on the paddle.

In one aspect of this disclosure, the method and system utilizes optical character reader (OCR) technology to trigger as an automatic ON-OFF switch for recording in the mapping system only while the fluoroscopy is ON.

Generally, when the physician pushes on the paddle and fluoroscopy goes ON, a symbol appears on the fluoroscopy screen to show that the fluoroscope (or radiation) in ON. The symbol element is generally shown on the top left corner of the fluoroscopy screen, and the symbol stays there while the fluoroscopy is ON. The exact symbol and placement of the symbol is dependent on the specific company that manufactures the fluoroscopy equipment. Since, the (radiation) symbol appears on the screen, the software for this disclosure is coded and 'trained' to recognize when the symbol appears and disappears utilizing optical character recognition (OCR) training and algorithms. This may be done utilizing one of various vision software languages as is known in the art. Further, in this disclosure the appearance and disappearance of the symbol on fluoroscopy screen is used as a switch to turn the recording ON and OFF. This is summarized with the help of a flow diagram in FIG. 22.

In step 580 the procedure begins. At some point the physician needs fluoroscopy for visualization and in step 582 the physician steps on the paddle. This causes the fluoroscopy to turn ON which is step 584. Once the fluoroscopy is ON, the software recognizes the symbol (step 586), and starts the recording in the computer workstation of the mapping system (step 590). In step 596, the recording stays on until the physician takes the foot OFF the peddle (step 588). Once the physician takes foot off the paddle, the fluoroscopy is turned OFF. This triggers step 594 where the workstation stops the recording. If the physician steps on the paddle again, the fluoroscopy is turned ON again as seen in step 584. This ON and OFF continues, and each time the segment is recorded and is saved in a separate file, until the procedure ends (step 600)

In our implementation, once the recording is started, every time the physician presses on the foot paddle and then releases it, the segment is stored in a separate file at a path specified in the code. The folder keeps on accumulating the files until the operator is ready to use them. This is shown in conjunction with FIG. 23. The panel on the lower right corner 602 shows that, every time the physician goes ON and then OFF, a file is stored of the fluoroscope recording for that particular duration which is variable.

The software is configured and programmed such that when the symbol appears on the fluoroscopy screen, it acts as a switch for the system to start recording, and when the symbol disappears the system is commanded to stop recording. The implementation of this may be done utilizing various different software's, as is known in the art.

In the implementation, the coordinates of the area where the symbol appears is regionalized and stored in the code. The software is then trained to recognize the symbol when it appears and trigger the recording mode. It will be clear to one skilled in the art that this can be done for various manufacturers of fluoroscopy equipment.

Going back to FIGS. 19 and 20, the recorded high resolution image 570 and live fluoroscope image 572 which is generally in lower resolution are displayed and adjusted in a way such that they are layered exactly on top of each other on the screen, shown as 570 and 572 in the figure. Whether the "live" or recorded image(s) appears on the top or bottom can be interchanged in the software. Further, the software is configured and programmed such that a transparency factor between the two said images can be adjusted. This is depicted in our implementation in conjunction with FIG. 20, via a slider bar 574, which can be adjusted for the transparency factor which is variable, other means of adjusting relative transparency may also be used.

The transparency factor is generally a level of transparency between the recorded image and the live image. The relative transparency level can be adjusted with a slider bar 574 in our implementation. At one extreme of transparency, only the recorded image is visible and live image is masked. At the other extreme, only the live image is visible and the recorded image is masked. At any level in-between the relative weight between or clarity between recorded or live image shifts and is adjustable.

By adjusting the transparency level, the physician can utilize the outline of the pulmonary veins highlighted with contrast medium injection, and appropriately place the catheter (for example a balloon based catheter) utilizing the combination of live fluoroscopy and recorded images. As known to one skilled in the art, this can be implemented utilizing a number of different softwares, as is well known in the art.

Based on experimentation, typically, the transparency factor is adjusted somewhere in the middle based on physician preference and choice. Advantageously, the physician gets the benefit of the recorded and stored high resolution image while being exposed to only low level of radiation of the live fluoroscopy setting.

Figure 24:
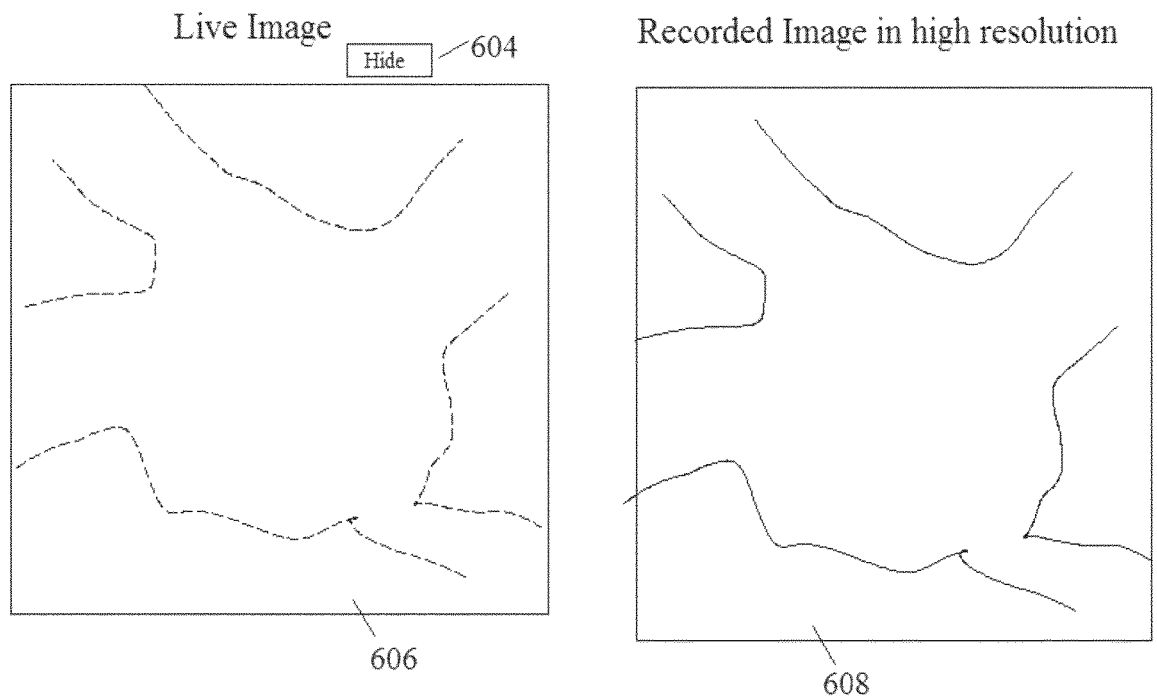
FIG. 24 depicts side by side images where one image is a recorded high resolution image with contrast medium ("dye") injected, and the other image is live fluoroscopy image.

In another embodiment, as depicted in FIG. 24, the recorded high resolution image 608 and live fluoro images 606 are depicted next to each other. Based on the high resolution image 608 with contrast medium, the outline 603 of the four pulmonary veins can appear drawn on the live fluoroscope, as a guide for cryoballoon catheter placement of any other type of balloon based or a circular catheter placement.

Figure 25:
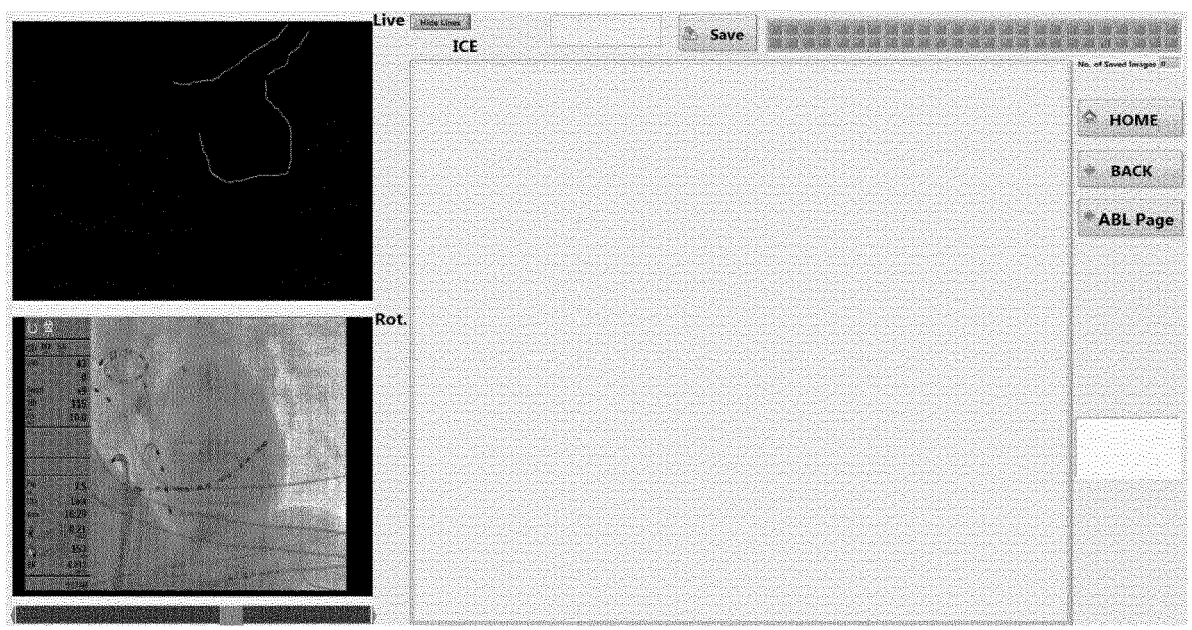
FIG. 25 shows one screen in the implementation of the mapping system where recorded high resolution image, live fluoroscopy image and intra-cardiac echo (ICE) is shown in one screen.
Figure 26:
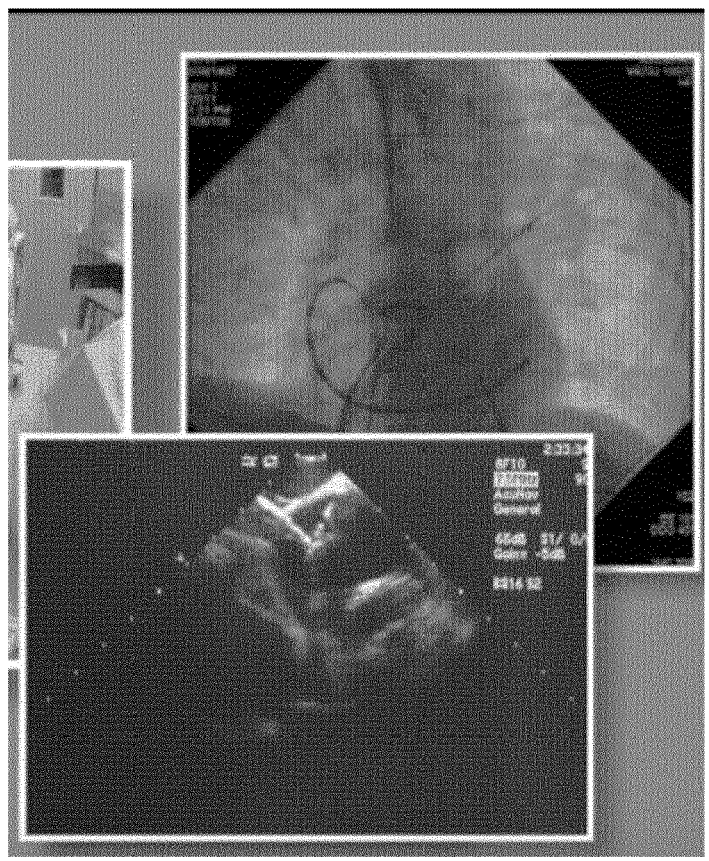
FIG. 26 shows another example of implementation where fluoroscopy and ICE are shown for placement of the cryoballoon for cryo ablations.

In one aspect live fluoroscopy, recorded "enhanced" fluoroscopy and ICE images are displayed, as is shown in conjunction with FIG. 25. In one aspect, fluoroscopy and ICE may be used in conjunction with each other (shown in FIG. 26) for the optimal positioning of the cryoballoon catheter or other catheters.

Cryoablation using cryoballoon catheter is generally performed utilizing a freeze, thaw, freeze technique. As previously stated, the goal is to render the tissue between pulmonary veins and the left atrium (LA) to be rendered electrically inactive by the ablation procedure, for all the pulmonary veins. Generally, one pulmonary vein is done at a time.

Figure 27:
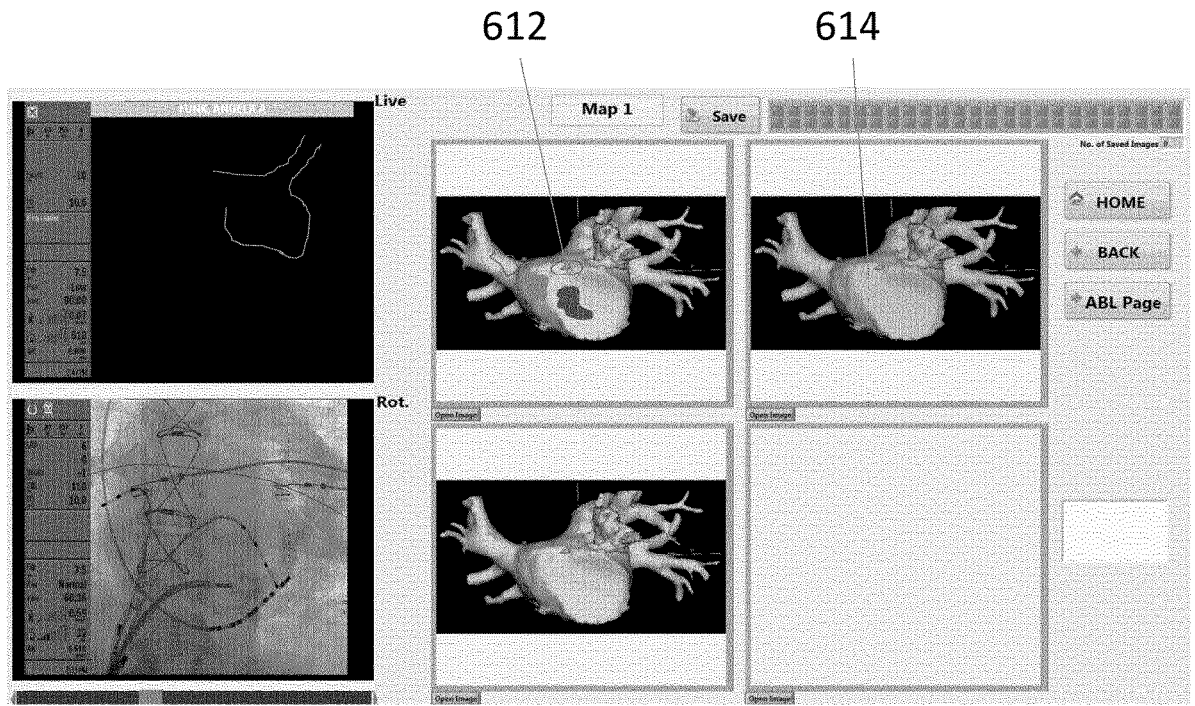
FIG. 27 shows another example of implementation where, recorded high resolution fluoroscopy, live fluoroscopy and CT images are displayed on the same screen.

In one aspect, computed tomography (CT) scans if available are also displayed in addition to enhanced fluoroscopy image and regular fluoroscopy image. One example of an implementation of this is shown in FIG. 27. In this example, CT images 612, 614 are displayed next to fluoroscopy.

Figure 28:
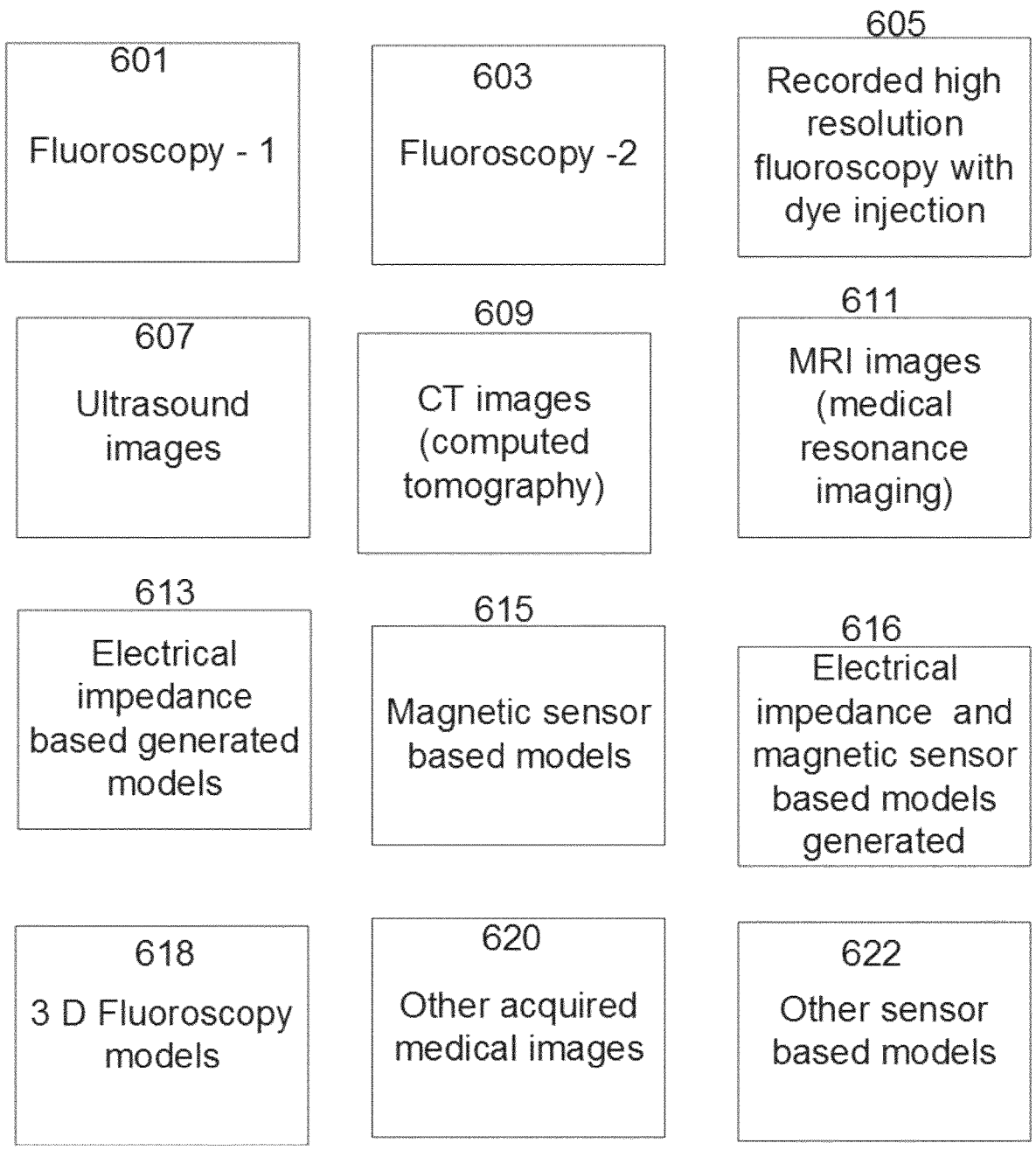
FIG. 28 is a block diagram showing different types of medical images that may be utilized or used in any combination in the mapping system of this disclosure.

Further, in the method and system of this disclosure, various different types of medical image modalities are utilized. These are shown in FIG. 28. These include fluoroscopy image(s) or various layers of fluoroscopy images 601, 603, 605. The fluoroscopy image(s) include monoplane or bi-plane fluoroscopy, fluoroscopy rotations, fluoroscopy rotations with dye injections or fluoroscopy based 3D models. Live fluoroscopy image(s) may be superimposed or overlaid on top of (or bottom) a recorded fluoroscopic video or image which has been recorded in 'high' resolution with contrast medium (or "dye") injections.

Other images include intracardiac ultrasound (ICE) images 607, CT (computed tomography) images 609, MRI (magnetic resonance imaging) images 611, electrical impedance based generated models 613, magnetic sensor based models 615, electrical impedance and magnetic sensor based models 616, 3D fluoroscopy models 618, other acquired medical images 620, and other sensor based models 622.

In the method and system of this disclosure, any combination of image modalities shown in FIG. 28 may be used by the mapping system for Cryoballoon ablation mapping system, or any other balloon based catheter based mapping for atrial fibrillation ablations. It may also be utilized in radiofrequency (rf) ablations and placement of a circular catheter around pulmonary veins.

Some of these combinations, without limitation are shown in FIGS. 29-36.

Figure 29:
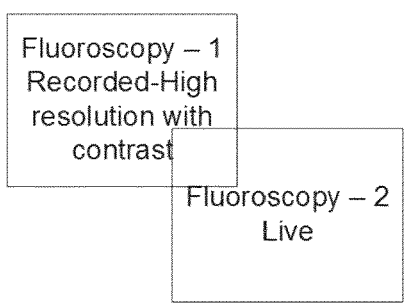
FIG. 29 is a block diagram showing two layers of fluoroscopy images overlaid/stacked on top of each other.
Figure 30:
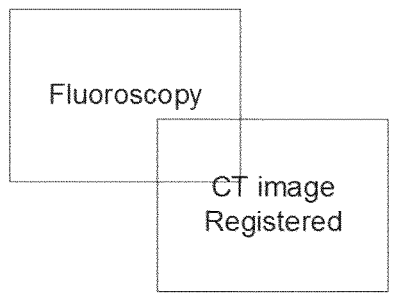
FIG. 30 is a block diagram showing CT images registered with fluoroscopy images.

In one aspect as shown with FIG. 29, live fluoroscopy may be aligned and superimposed or overlaid on top (or bottom) of a recorded high resolution fluoroscopy, which is recorded with contrast medium injection. The software is configured and programmed in a way, that a transparency factor adjusts the relative transparency between the recorded and live images. The recorded image is generally recorded in "high" resolution, with contrast medium (dye) injection. Provided the fluoroscope C-arm view and magnification factors are not changed, this technique offers the advantage that the live fluoroscopy manipulation or placement of leads or Cryoballoon catheter can take advantage of the high resolution and contrast medium (dye) injection.

In applicant's clinical testing, this has shown to be of significant help in placing of the Cryoballoon catheter in each of the four pulmonary veins. The same methodology also applies to any balloon based catheter as an aid for the proper placement of the catheter in the left atrium or around pulmonary veins.

Figure 40:
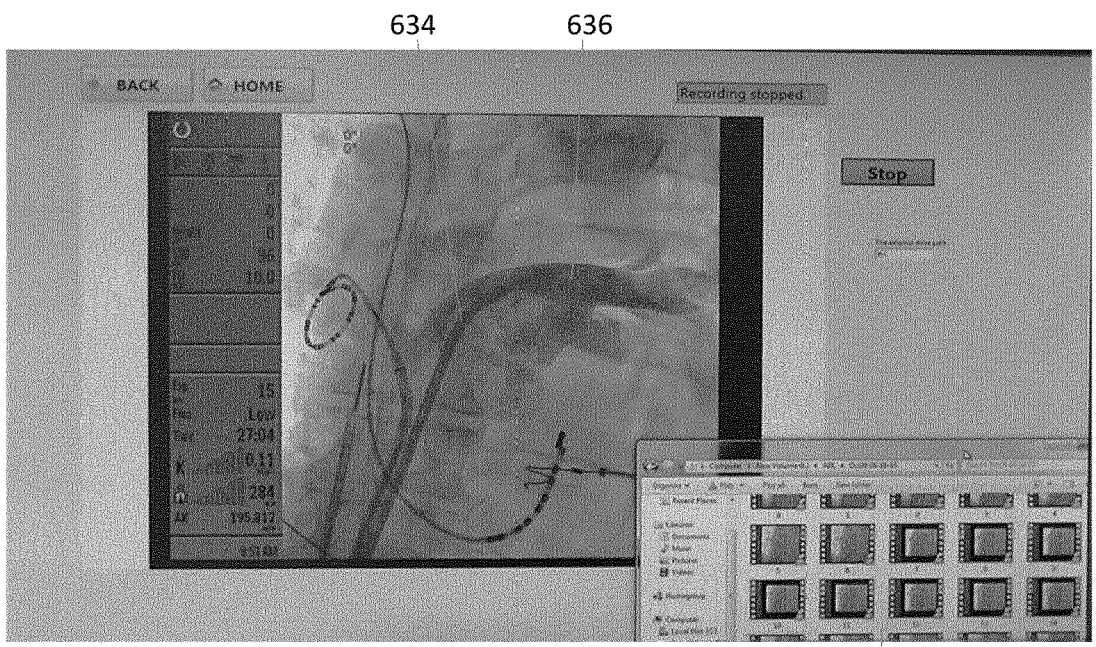
FIG. 40 is a diagram showing a recording of fluoroscopy with contrast medium ("dye") injection close to left superior vein.

One implementation is shown with FIGS. 40-42. In the first part of the implementation shown with FIGS. 40 and 41, a recording is made with contrast medium (dye) injection. FIG. 40 shows contrast medium in the superior pulmonary vein 636. A lumen catheter 634 is inserted in the left atrium close to left superior pulmonary vein 636, and the dye (or contrast medium) is injected. A recording is made of the dye injection. Other balloon based catheters are placed in the same way.

Following that, as is shown in FIG. 41 in our implementation, the recorded image (with dye injection) 640 is placed underneath the live fluoroscopy image 642. A transparency factor bar 644 is adjusted by an operator to have the right ratio of recorded image vs live fluoroscopy image. Utilizing this methodology, the physician is able to place the Cryoballoon catheter in appropriate pulmonary vein for the ablation procedure.

Figure 43:
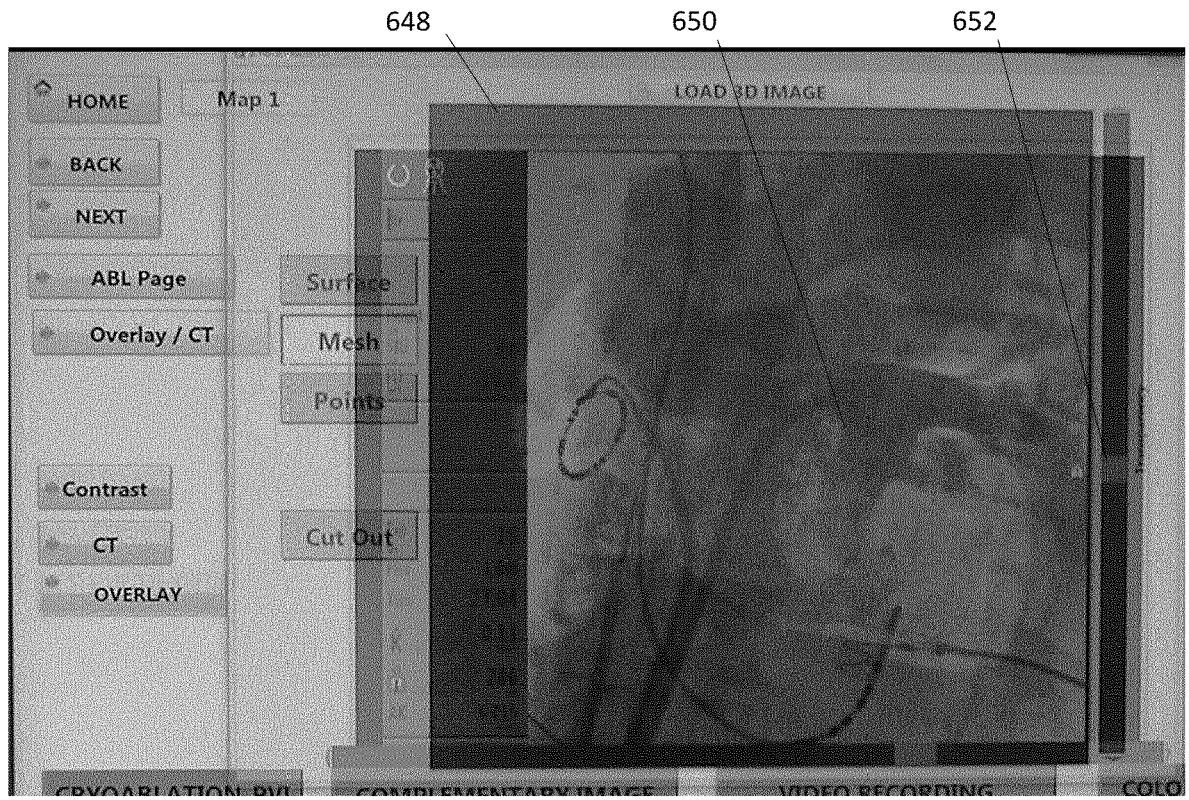
FIG. 43 is a diagram showing one implementation where a CT image is overlaid on a recorded fluoroscopy image with contrast medium ("dye") injection, and the structures are matched.
Figure 53:
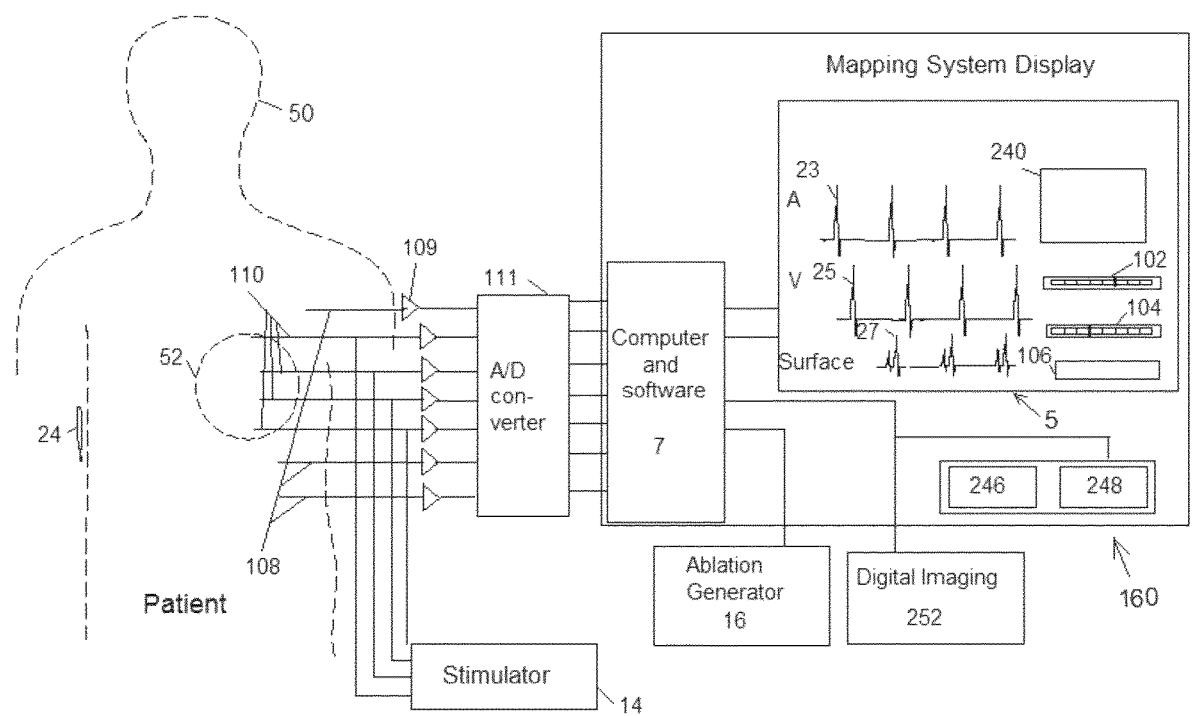
FIG. 53 is a diagram depicting the process of displaying the cardiac signals and relationship to the patient and other equipment.

In another aspect, as shown with FIGS. 42 and 43, computed tomography (CT) images may be combined with fluoroscopy. It will be clear to one of ordinary skill in the art, that the CT image(s) may be registered or just overlaid on the fluoroscopic image(s). Registering the images involves some extra steps such as matching known anatomical points on both of the images. This is shown with FIG. 42. FIG. 53 shows an embodiment, where the CT images are combined or matched and overlaid on fluoroscopy, but are not registered. In Applicant's clinical testing this is still very useful. In this aspect, an operator visually matches the structures of the CT image with the structures on the fluoroscope. This is aided by the contrast medium (dye) injection.

Transparency

When a picture-1 (image or video) is placed on top of another picture-2 (image or video), the picture on the bottom (picture-2) is normally completely hidden. By utilizing software, a transparency factor (which can be gradual and continuous) can be configured and programmed. At one extreme of the transparency factor, the picture-2 at the bottom is completely hidden, and picture-1 is at full view. At the other extreme, picture-1 on top can be completely masked and picture-2 on bottom is in full view. This would be similar or equivalent to the top picture becoming transparent like clear glass. Utilizing software, the relative transparency between the two pictures can be easily adjusted such that the picture on the bottom is visible enough to show and take advantage of, while the picture on top (picture-1) can be used for any purposes.

In one application of this disclosure, the picture-1 can be live fluoroscopy image or video and the other (picture-2) can be a recorded fluoroscopy image of video, which was recorded with contrast medium injection ("dye") preferably in the highest resolution. By placing the live fluoroscopy on the recorded image or video with contrast, and adjusting the relative transparency between the live and recorded images, both can be utilized in a meaningful way. That is, live fluoroscopy can be used for catheter manipulation and placement, utilizing the recorded detailed anatomy and structure boundaries that are available from the contrast medium injection and which is placed underneath. The live and recorded images can also be interchanged, i.e. the recorded image can be placed on top and live fluoroscopy can be on bottom.

Similarly in another application, a CT model can be placed on top of, with structures aligned and matched with a recorded dye injected fluoroscopy, then in turn live fluoroscopy can be placed on top of these two images. By adjusting the transparency factor between the three images, all the images can be utilized. For example, the catheter can be manipulated and placed utilizing live fluoroscopy, while using the anatomic details of recorded "dye" injection, and the detailed anatomy of the CT scan.

The same methodology can be applied to different types of images shown in FIGS. 37 to 44.

Figure 44:
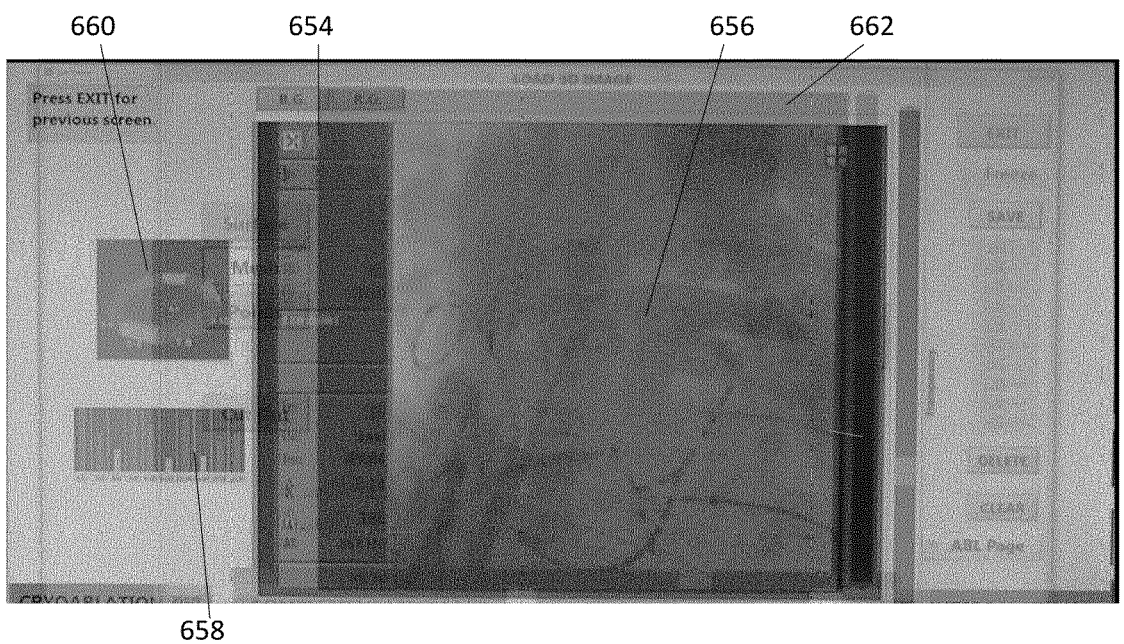
FIG. 44 is an implementation of the concept shown in FIG. 28, i.e where CT image is overlaid on a recorded fluoroscopy image and live fluoroscopy is overlaid on top of that. Further, electrical signals are also displayed on top fluoroscopy layer.

An implementation of this is shown with FIGS. 43 and 44. In the first step shown in FIG. 42, a volume rendering is done of the CT image 646. This volume rendering may be done on the mapping system via an appropriate software, or may be done on separate computer. The volume rendered 3D CT image 646 is then brought into the mapping system workstation. In the next step shown in FIG. 43 the volume rendered 3D CT image is superimposed on the recorded fluoroscopy image. As previously mentioned, this superimposition may be performed by registering the CT image on the fluoroscopy image or via the operator aligning the CT image with the recorded or live fluoroscopy image. Of course, for performing the registration process, points or tags will have to be specified on the both the fluoroscopy image and the CT image.

A transparency factor bar is generally adjusted by the operator, to show the relative weight of the fluoroscopy image vs the CT image.

In another aspect, two layers of fluoroscopy may be combined with the CT image. This is shown in conjunction with FIG. 44. In this aspect, high resolution fluoroscopy with contrast (dye) medium injection is recorded and stored in the computer (of the mapping system). In the next step, the appropriate images are brought on the monitor screen. Following that, the CT image which is 3-D is overlaid or registered on the recorded or high resolution with dye image.

It will be clear to one skilled in the art, that for the CT image to be registered approximately three common points on the each structure will need to be identified and tagged. Then via known algorithms, the images are registered when the algorithms are executed.

As an alternative, the images are matched by an operator. By utilizing the outline of the contrast medium, the CT image is matched to the outline of the fluoroscopy structures by the operator manually. This can be done, as the operator is manually able to pan, zoom and rotate the CT model on the monitor manually using a mouse. Since the placement of the Cryoballoon catheter (or other balloon based catheter) is done only one vein at a time, the operator only needs to match only one vein at a time. The advantage is that this can be done quickly and is relatively simply.

Applicant's implementation and testing of this aspect is shown in conjunction with FIG. 44. In this figure, the first (bottom) image on the screen is a high resolution recorded fluoroscopy segment with dye injection, which has a nice outline of the left atrium and at least one of the pulmonary veins. The CT image 656, is placed and aligned by the operator on the outline of the heart, which is aided by the "dye" or contrast medium injection. On top of these two layers (recorded fluoroscope and CT image) is a live fluoroscopy layer. This gives a physician the advantage of the contrast medium (dye) injection and the detailed anatomy from the CT scan.

This aids the physician in the proper placement of the Cryoballoon catheter and/or the electrode catheter in and/around the pulmonary vein. After placing the Cryoballoon catheter, and appropriate placement of the balloon, the ablation or freezing is performed. In some cases, the physician may inject a small amount of dye from the Cryoballoon catheter to check the seal of balloon with the pulmonary vein ostium (os).

The above procedure will be repeated at least four times to isolate all four pulmonary veins, as is generally done to complete the procedure.

In one implementation, the software is configured and programmed such that visual indicator of voltage levels from each pulmonary vein are shown as bar graphs indicating peak-to-peak voltage levels from different areas of the pulmonary vein. Actual signals are also shown below the bar graph.

In one embodiment, the bar colors are color coded to display the voltage levels. In this embodiment, the color coding guide is shown above the fluoroscopy image.

As is known to one skilled in the art, far-field signals from the left atrium (LA) are frequently recorded from electrodes placed in the pulmonary vein. To separate the far-field signals from the pulmonary vein recordings, physicians may perform pacing from the coronary sinus (CS) level. Alternatively, the signals may be displayed in the frequency domain. As the frequency content of the pulmonary vein potentials is different than the frequency content of left atrial signals.

Figure 33:
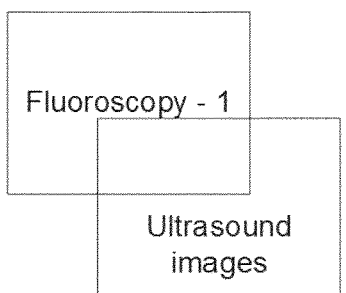
FIG. 33 is a block diagram showing combining ultrasound imaging with fluoroscopy for the purposes of the current mapping system.

In one embodiment, the ultrasound images are combined and superimposed on fluoroscopy. This is depicted in FIG. 33. Generally, ultrasound images have many advantages, and are routinely utilized during atrial fibrillation procedures performed in the United States. The ultrasound technology utilized is generally in the form of Intracardiac echocardiography (ICE). The advantages of ICE includes features where the images actually show the anatomic structures and unlike fluoroscopy or x-ray, ultrasound does not emit ionizing radiation.

Figure 35:
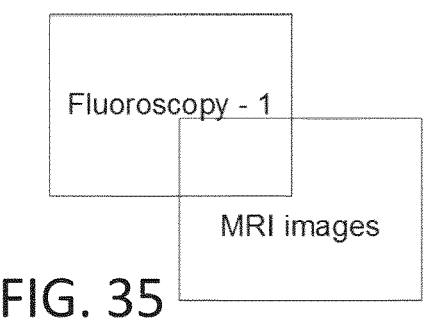
FIG. 35 is a block diagram depicting combining MRI images with fluoroscopy imaging.

In one embodiment, depicted in FIG. 35 fluoroscopy and MRI images are combined together. MRI images may be either registered or overlaid on fluoroscopy images. The MRI images also provide detailed 3D imaging, much like the CT images. As was mentioned previously, if the MRI images are registered then several tags will be placed on both the structures that are being registered. Alternatively, the MRI images may be placed or overlaid on fluoroscopy as a guide to place the Cryoballoon catheter in the proper vein.

Figure 36:
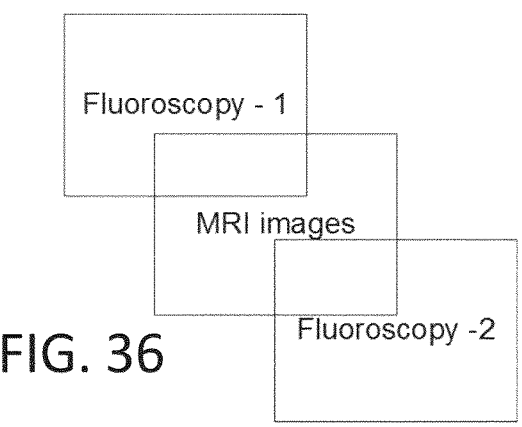

In one embodiment, two layers of fluoroscopy and MRI images may also be displayed on the monitor to guide the physician, this is shown with FIG. 36. In one aspect, high resolution fluoroscopy with contrast medium (dye) injection is recorded and used as an outline for the chamber geometry and for pulmonary vein(s). Based on the outline of the recorded images, the MRI images are positioned to the appropriate location. As with the case of CT, the MRI images may be registered with fluoroscopy based on placing common landmark tags on the recorded high resolution fluoroscopic images and the MRI. Alternatively, the MRI images may be placed by an operator (or overlaid) on the outline of the heart and/or pulmonary veins utilizing tools such as pan, zoom and rotate. Following that, a live fluoroscopy image layer is placed on the first two layers. The physician then positions the Cryoballoon catheter based on the real-time fluoroscopy layer, taking advantage of the recorded fluoroscopy and the high resolution anatomy of the 3D MRI images which are in the background.

Figure 34:
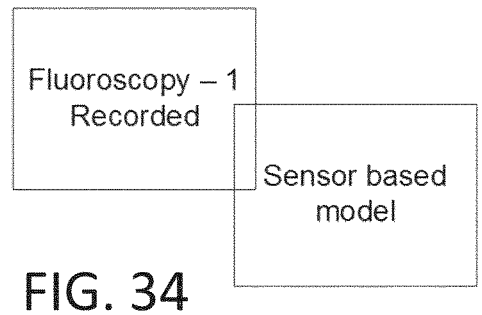
FIG. 34 is a block diagram depicting a sensor based model imaging combined with fluoroscopy imaging for the purposes of the current mapping system.

In one aspect shown with FIG. 34, a sensor based model of the heart geometry is created and registered or overlaid on fluoroscopy. The rationale for doing this is that since the Cryoballoon catheter does not communicate with sensor based mapping systems, fluoroscopy will be utilized for the placement of the Cryoballoon catheter. It will be clear to one skilled in the art that many different types of sensor based catheters are available for creating geometry. The most popular ones are electrical impedance based sensors, magnetic sensors or combination of electrical impedance and magnetic based sensors. The left atrial chamber geometry may also be made utilizing an ultrasound based catheter.

In one aspect, while recording a contrast medium ("dye") injection, a rotation of fluoroscope C-arm may be recorded. If a complete rotation is recorded, the software is programmed and configured such that any angle of fluoroscopy is available and may be used.

Figure 37:
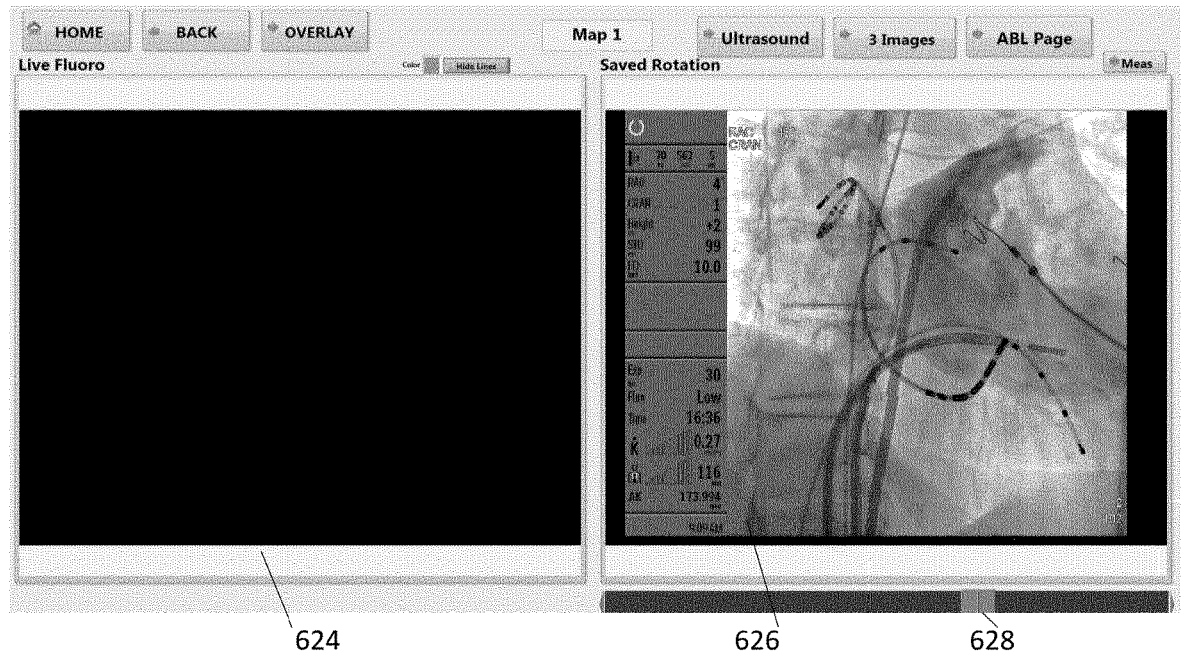
FIG. 37 is a diagram showing one implementation where live fluoroscopy and recorded fluoroscopy are displayed side-by-side.

One example of implementation is shown with FIG. 37. As shown in FIG. 37, a live fluoroscopy and a saved fluoroscopy rotation is displayed side-by-side. The saved rotation 626 is on the right side of the figure and the live fluoroscopy 624 is on the left side. Since the whole rotation is saved with contrast medium (dye) injection, as the live fluoroscopy angle is changed by the physician, the recorded "dye" injection fluoroscope image can be changed to the same angle as the live (or real-time) fluoroscope angle. In this implementation, a slider bar 628 is used to adjust the angle of the fluoroscope to match the angle of the live fluoroscope (shown on the left side of the figure).

Figure 38:
FIG. 38 is a diagram showing one implementation where live fluoroscopy and recorded fluoroscopy are displayed side-by-side and outline of the chamber and pulmonary veins are outlined on live fluoroscopy.

In one aspect, as is shown with FIG. 38 the recorded contrast medium ("dye") injection image may be used to mark the outline of the atrium and pulmonary veins on the live fluoroscopy. This is then used by the physician to guide a catheter, such as a cryoballoon catheter or any other catheter into the pulmonary veins or the os of the pulmonary veins.

Of course, the physician has control over the amount of contrast medium ("dye") to inject and where to inject the contrast medium ("dye"). Generally, one of two methods are used. In one method, the contrast medium ("dye") is injected with a power injector in the right side of the heart. In this case the contrast medium ("dye") will go through the lungs and return to the pulmonary veins and the left atrium. At the point the "dye" starts to show up in the pulmonary veins (in approximately 5-8 seconds), a recording is generally made.

Figure 31:
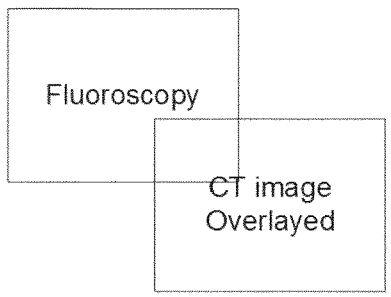
FIG. 31 is a block diagram depicting CT images overlaid/stacked on top of fluoroscopy images.
Figure 32:
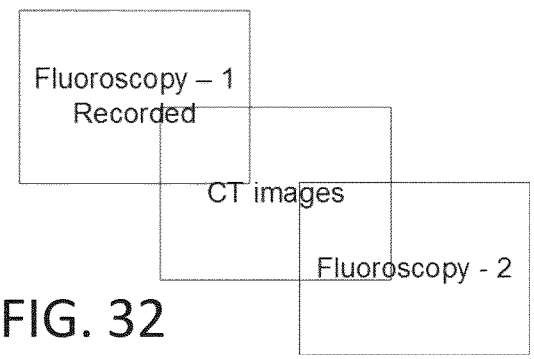

An example of the image obtained with this method is shown in FIG. 31. The second method is to inject the "dye" straight into the left atrium and/or pulmonary veins, with or without a power injector.

Figure 39:
FIG. 39 is a diagram showing a recording of fluoroscopy with contrast medium ("dye") injection.

In our implementation, FIG. 39 shows an example of "dye" injected into the left atrial chamber 632 via a lumen catheter 630. This is also substantiated with the "dye" being above the coronary sinus (CS) catheter 629 shown in the picture. Anatomically, the coronary sinus (CS) runs between the left atrium and left ventricle.

Also, for our implementation FIG. 40 shows an example of "dye" injection, this time in the left superior vein 636 via a lumen catheter 634 close to the os of the pulmonary veins.

FIG. 41 shows our testing of the concept shown in FIG. 29, where two fluoroscopy images are overlaid on top of each other. Once the two layers of fluoroscopy, high resolution images with contrast medium ("dye") and live fluoroscopy are overlaid on top of each other, one of the images may be manually moved to align the structures such that they are overlaid on top of each other and aligned and adjusted appropriately. The software is configured and programmed such that the transparency between the recorded and stored image(s) and live images can be adjusted by the operator. This is implemented with the aid of transparency bar 644, as shown in the figure. At one extreme of the transparency bar, only the recorded image(s) are visible. At the other extreme, only the live fluoroscope is visible. The transparency is adjusted by the operator such that the physician can manipulate the catheter on the live image, but at the same time have the benefit of the clear anatomic details from high resolution images with contrast medium ("dye") injection.

Further, as the catheter is placed in the appropriate pulmonary vein, the electrical signals are also recorded. The software and hardware is configured such that each pair of electrode picks up the peak-to-peak voltage signals, color codes the signals according to the size of the voltage levels and display's them in the form of a real-time bar graph 641 or ring graph 643. The ring graph 643 is configured and programmed such that the ring 643 is a 3D structure which can be rotated or moved in any angle.

In one aspect, a volume rendered 3D image if available can also be utilized in the placement of the catheter for atrial fibrillation ablation. A patient's CT scan is processed and a 3D volume rendering of the region of interest is obtained using software and techniques well known in the art. An example of this is shown in FIG. 42. The 3D volume rendering of the image 646 is done either using the mapping system computer, or is done on a separate computer and brought into the mapping system computer. The CT image 646 (in FIG. 38) can be panned, zoomed, moved or rotated such that it can be properly aligned with other images such as the fluoroscope image for example.

In one aspect, as was mentioned earlier and shown with FIG. 42, the CT image may be used with recorded fluoroscopy image (high resolution with contrast medium or "dye" injection) and live fluoroscopy for aiding the placement of the catheter such as balloon catheter or any other catheter which needs to be placed around the pulmonary veins.

In our implementation, shown in FIG. 43, in the first part the CT image 646 is aligned with recorded fluoroscopy image which may be in high resolution along with contrast medium injection or "dye" injection. The purpose of this is to show the details of the appropriate anatomy and to match the structures of the CT image with the fluoroscopy image.

In one aspect, the CT image may be registered with the fluoroscopy image. For the registration process several points (at least three) need to be defined that are common to both structures.

In one aspect, instead of registering the CT image with fluoroscopy, the CT image is overlaid on the fluoroscopy. The size, orientation and position of the CT image to match fluoroscopy structures are manually performed by the operator. This involves approximation and operator judgment, but for the current application, it works well.

Shown in FIG. 43, is one implementation which we have tested and found to work well. The operator adjusts and overlays the CT image on the fluoroscope after it has been properly resized and properly oriented. Further, the transparency is adjusted such that when live fluoroscopy is overlaid on top of the CT image such that it will be useful.

FIG. 44 shows, the final layer of live fluoroscopy which is placed at the top layer for visualization and placement of a cryoballoon catheter or any other catheter. Once the catheter is placed in the proper position, the signals may also be recorded as is shown in bargraph 658 or in the form of a 3D ring 660 as is shown in the figure.

As the Cryoballoon catheter is placed in the appropriate pulmonary vein, an electrode catheter with multiple electrodes is generally advanced and placed in the pulmonary vein more distal to the balloon.

Referring again to FIG. 44, as the Cryoballoon catheter is placed in each of the pulmonary veins and the multiple electrode catheter is placed in the pulmonary veins, the signals recorded from the electrodes are displayed on the monitor along with the fluoroscope image. In the method and system of this disclosure, the underlying signals from each electrode are recorded and displayed on the monitor screen. This is shown in the form of a bar graph 658, which are the peak-to-peak voltage signals. In one aspect the software is configured and programmed such that the bars are color coded based on the underlying peak-to-peak voltage. Additionally, in one implementation the underlying signal measurements are converted to color based on a color coding scheme and are displayed in the form of a ring 660 which adds a three dimensional element, as the ring can be manipulated in 3D.

In the method and system of this disclosure, after the balloon is inflated and the catheter is appropriately placed in the pulmonary vein, ablation is performed by freezing the tissue. The length or duration of freezing is determined by the physician. In one aspect of the disclosure, the ablation (freezing) areas' are marked or "tagged" for aiding the procedure and also stored for documentation purposes. In the method and system of this disclosure, various ways are disclosed for this and are shown with FIGS. 45-47.

The software is configured and programmed in a way such that every time there is an ablation, the area representative of the ablation contact area of freezing is marked ("tagged"). Generally, in RF ablation the ablation area is relatively small because the ablation is point by point ablation. With Cryoballoon ablation, the whole pulmonary vein is typically freeze ablated in a single shot. Therefore, the ablation tagging ideally needs to be such that it captures that.

Figure 45:
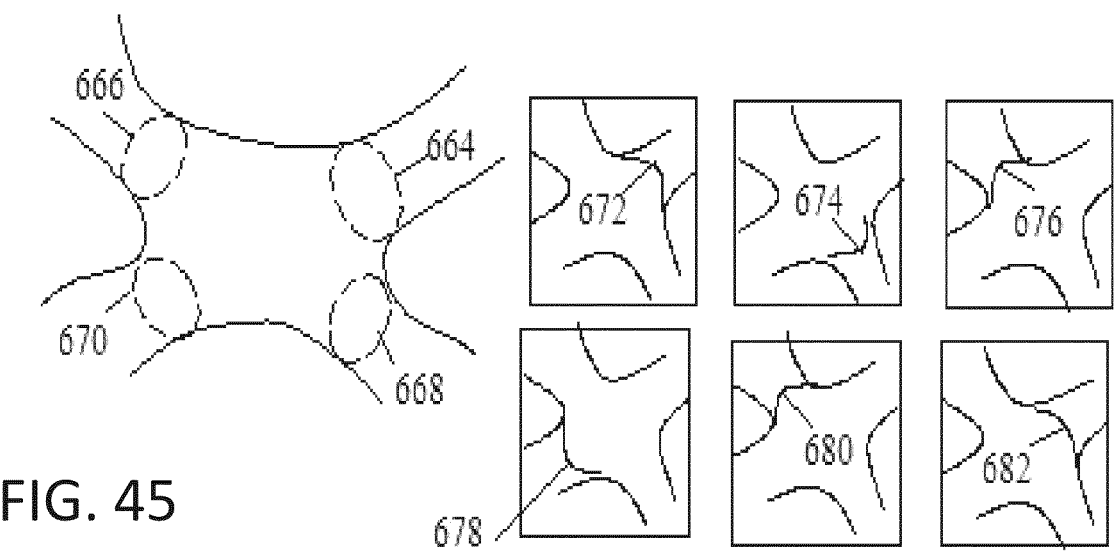
FIG. 45 is a diagrammatical representation showing marked sites of individual cryoballoon catheter freezes or cryo-ablations.

In one aspect, shown in conjunction with FIG. 45 the software is configured and programmed such that the ablation contact area is marked with the aid of a computer mouse by drawing a series of lines or circles or other markings. In one embodiment, each freeze is saved as separate picture or frame. Therefore, if there are six freezes (ablations) for example, then six pictures are saved. In the review screen, all of the screens are shown next to each other, for the physician to visualize where ablations have occurred.

As shown in FIG. 45, in the planning of the Cryoballoon ablation procedure at the level of left superior pulmonary vein os 664, left inferior pulmonary vein os 668, right superior pulmonary vein os 666, right inferior pulmonary vein os 670 are shown in the top portion of the figure. The bottom portion of the figure shows ablation markings or ablation "tags" 672, 674, 676, 678, 680, and 682 at various ablation sites. When the operator retrieves the review tag screen, the physician is able to visualize where the ablations have been performed.

Figure 46:
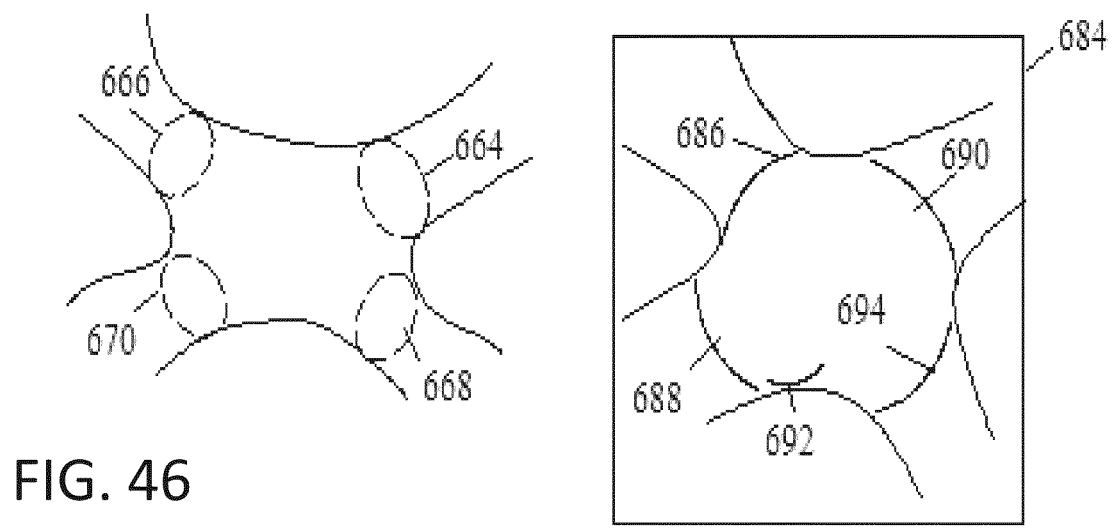
FIG. 46 is a diagram showing various cryo-ablations in one picture.

In another aspect, the various images comprising the ablation tags are merged together utilizing software coding and manipulation and are displayed in one figure. This is depicted in FIG. 46, where ablation tags 686, 688, 690, 694 and 692 are merged into one figure. As is well known to one skilled in the art, various software packages are available for this purpose. One such software for example is Photoshop, available from Adobe. MATLAB is another package which has built-in function libraries specifically for this. Many other software packages are also available and may be used. This may also utilize the process of registration in 2D.

Figure 47A:
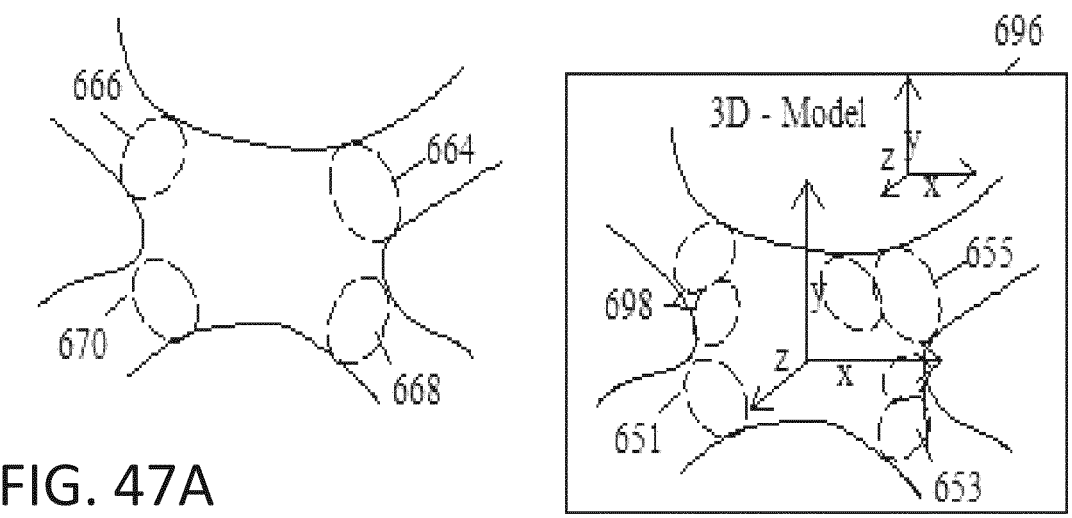
FIG. 47A is a diagram depicting various cryo-ablation lesions on a three dimensional (3-D) image, such as a CT image which can be rotated in 3-D (3 dimensions).

In another aspect, various ablation tags are placed on a 3D model, such as a 3D CT model or a 3D MRI model which is registered or overlaid on the fluoroscopy image, as described earlier in this disclosure. This embodiment is depicted in FIG. 47A, where tags 651, 653, 655, 696 and 698 are marked on a 3D model which can be rotated in 3D.

It will be clear to one skilled in the art that the 3D model may be one that is created using a sensor such as impedance, magnetic or any other type of sensor.

In one aspect, the ablation markings or "tags" may also be correlated with the length of the ablation freeze. For example, the ablation "tags" or markings may be color coded depending on the length of the freeze. In another example the "tag" markings may be larger or more dense depending on the length of the freezing time.

In this disclosure, in one aspect, both endoscopy based images, and CT (or MR) images or CT (or MR) images which are overlaid on fluoroscopy are displayed for navigation and guidance for atrial fibrillation ablation procedure. It is advantageous for navigation and guidance, to correlate the image view from inside the pulmonary veins (as via an endoscopy through the balloon catheter), and the outside or inside image view for placement via a CT or MR image(s). The CT or MR image(s) may be overlaid or superimposed on a fluoroscopy image(s). If the CT or MR image(s) is overlaid on the fluoroscopy image(s), a transparency factor between the fluoroscopy and CT images may be adjusted such that both the fluoroscopy and CT/MR images are visible for navigation and guidance. This is further explained in conjunction with block diagrams 47B and 47C.

Figure 47B:
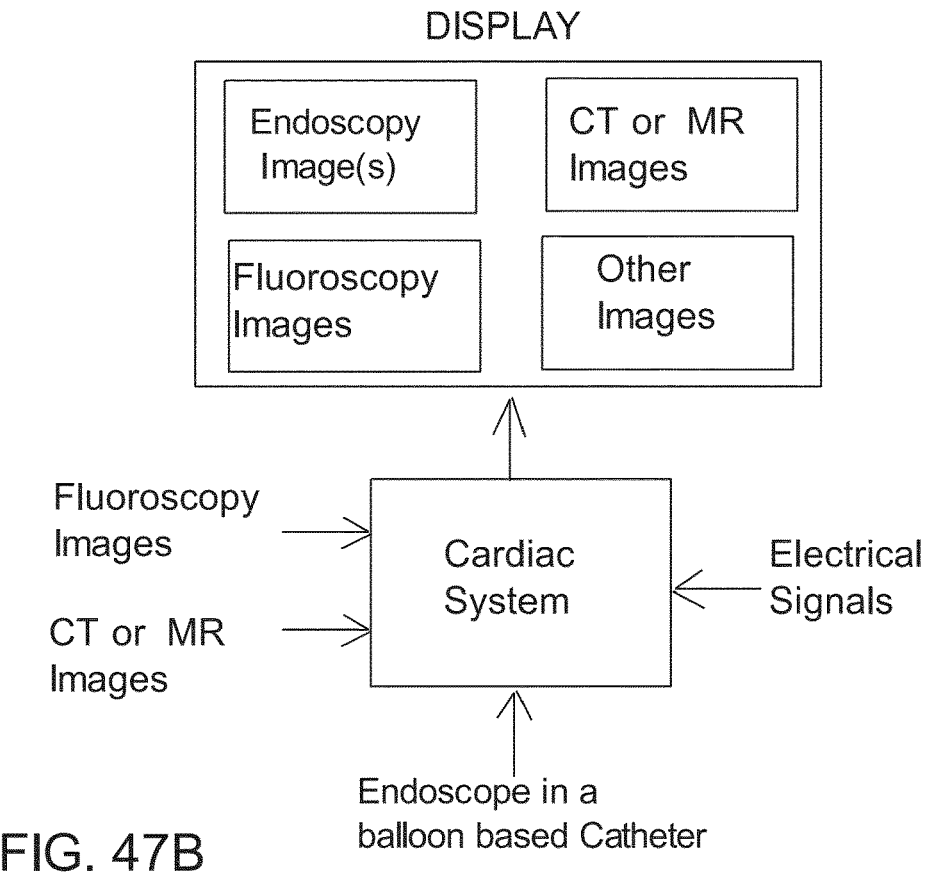
FIG. 47B is a block diagram depicting displaying images from endoscopy and CT (or MR) images, physicians to correlate inside and outside view of pulmonary vein region.

As shown in conjunction with FIG. 47B, the Cardiac System is connected to one or more display device(s). The Cardiac System of this disclosure has interface electronics for acquiring patient's electrical signals. The patient's electrical signals are any combination of surface EKG (generally 12-Lead) and/or intracardiac signals. The Cardiac System also comprises interface electronics for acquiring patient's fluoroscopy images. This may be in the form of a specialized board. Additionally, the Cardiac System also comprises means for acquiring patient's CT or MR images. The patient's CT or MRI may be 3D volume rendered on the Cardiac System via volume rendering software installed in the Cardiac System. Alternatively, the volume rendering may be performed on a separate computer or workstation, and the digital files stored in an appropriate format on an external storage medium, and this external storage device is then connected to the Cardiac System for transferring the digital files.

Typically, the endoscope is coupled to the balloon based ablation catheter. Depending on the manufacturer, the endoscopy catheter or fiber is threaded into the balloon catheter, or may go thru the balloon catheter. With some manufacturer's, when the endoscope is placed in the pulmonary vein for visualization, only blood is visible. But, once the balloon is inflated, the blood flow to that particular pulmonary vein is occluded, and visualization inside the pulmonary vein is generally very good. It generally gives a clear visualization of the pulmonary vein from inside. As the endoscopy is pulled back towards the left atrium, the os of the pulmonary vein is generally visualized, as well as, the branches. The branches (or the same region) is/are also visualized from the outside on the CT or MR images, or CT/MR images overlaid on fluoroscopy.

In the method of this disclosure, for the purpose of navigation and guidance for atrial fibrillation ablation, the physician is able to correlate the internal view via endoscopy and the external view via CT/MRI for the purpose of placing the balloon or for the purpose of directing the ablation energy, whether it's RF or laser energy, or any other form of energy.

The software and hardware of the Cardiac System is configured and programmed for displaying the endoscopic images, and CT (or MRI), or CT (or MRI) overlaid on fluoroscopy (images) on a display monitor. It will be clear to one in the art, that the display is on the same monitor, or the display may be on separate monitors where the physician can observe both monitors during the procedure.

The implementation for this is well known to one of ordinary skill in the art.

Figure 47C:
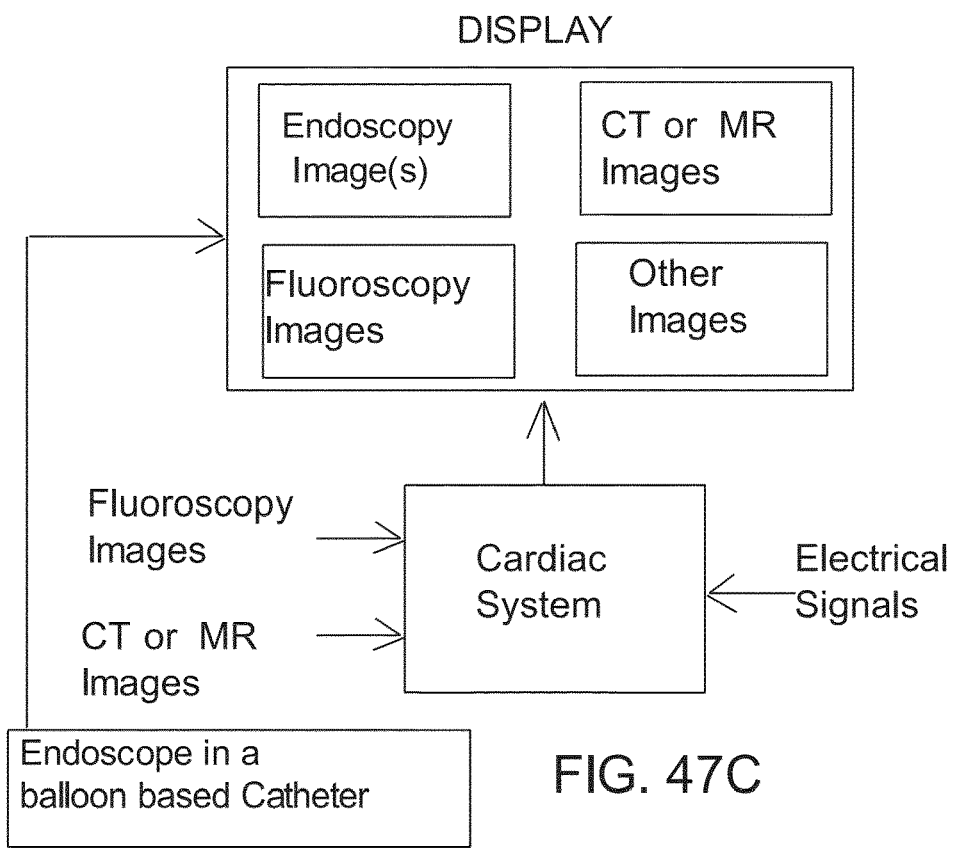
FIG. 47C is an alternative block diagram depicting displaying images from endoscopy and CT (or MR) images, physicians to correlate inside and outside view of pulmonary vein region.

As shown in conjunction with FIG. 47C, in an alternative embodiment the endoscopic images are not brought into the Cardiac System, but are displayed directly from the balloon catheter or endoscopic manufacturer's equipment directly on to a display monitor. And, CT or MR images are displayed from the Cardiac System on to the same display monitor or a separate display monitor close to each other, where the physician can observe both monitors.

Saving and Utilizing 3D Anatomical Structures in Separate Digital Files

In this disclosure, various anatomical segments are overlaid on images of live fluoroscopy. Anatomical segment(s) in this disclosure are one or more region(s) or an organ or part thereof on a patient's CT/MRI image identified as an area of interest, wherein each such area is 3D volume rendered and is stored in a separate digital file.

Figure 48:
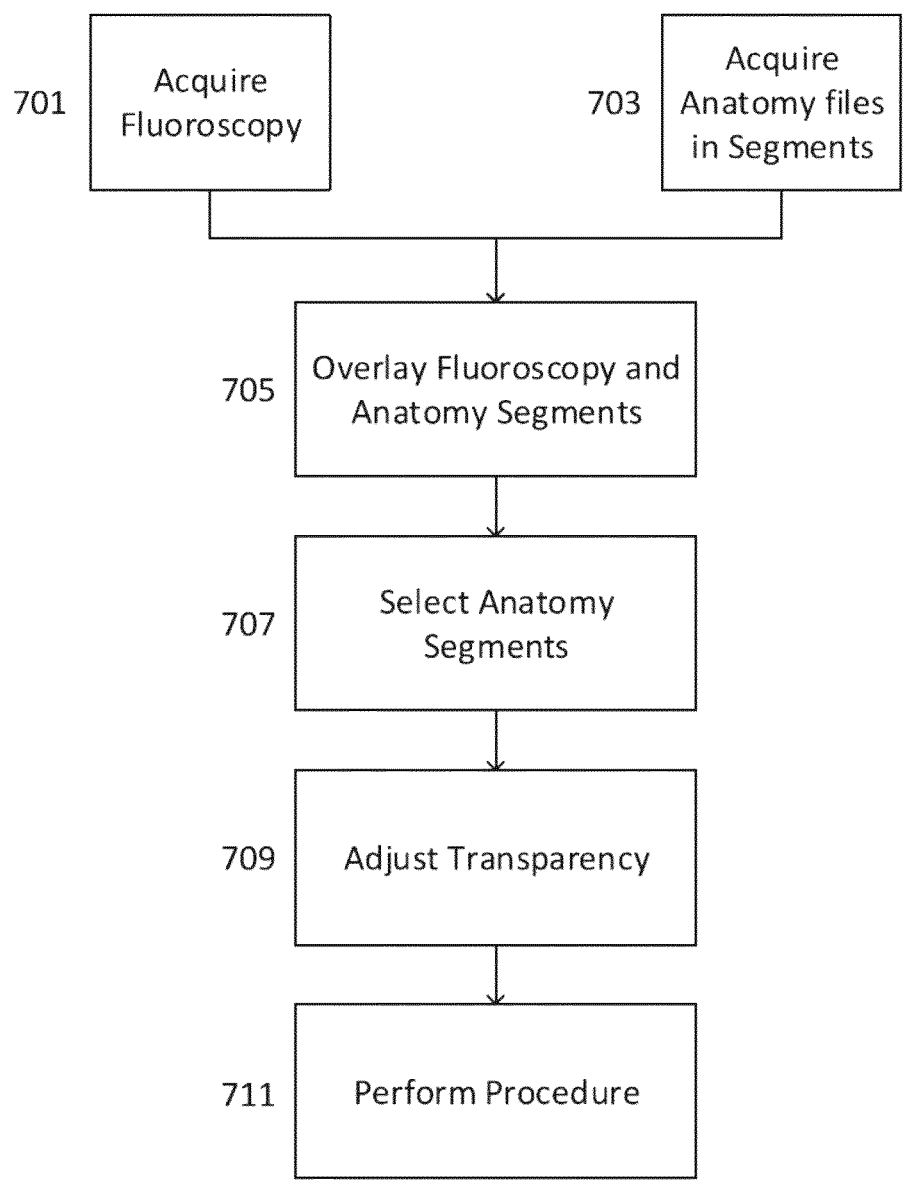
FIG. 48 is a simplified block diagram showing overlaying CT or MR image in segments on fluoroscopy.

FIG. 48, depicts the general concept of an overlay of anatomy in various CT (computed tomography) or MRI image segments and fluoroscopy, of one preferred embodiment utilizing a simplified block diagram. As depicted in the block diagram, live fluoroscopy images 701 are acquired into the system, utilizing an "image acquisition" board(s) which have been installed in the workstation. Additionally, CT (computed tomography) or MRI (magnetic resonance imaging) segmented files of various anatomical structures which have been volume rendered and segmented in 3D (3-dimensions) and saved as separate digital files, are also acquired into the workstation (block 703). In this disclosure, patient's CT (computed tomography) is analyzed, and various parts of the anatomy (described later) are 3D volume rendered and saved as separate digital files. Also, generally, an .stl file format is used, but other file formats may also be used. Any suitable file format for 3D structures may be used. For example, 3D PDF file format may also be used. It will be clear to one in the art, that MRI images are done essentially the same way. Thus, for the purposes of this disclosure any mention of images or CT segments also include MR images or MR image segments.

In one aspect, the 3D volume rendering is performed on the Mapping system workstation. In another aspect, the 3D volume rendering is performed on a different computer medium (including laptops or other computer devices), and the digital files may be saved on an external drive or some other storage media for transfer to the cardiac mapping system workstation.

In the disclosure of this invention, the various anatomy segments are combined together on the display, as they are synchronized spatially, and are overlaid or superimposed on live fluoroscopy images (block 705) (in this disclosure fluoroscopy implies fluoroscopy images). Advantageously, for aiding in the procedure, selected relevant anatomy segments are displayed. Importantly, the anatomy segments displayed are dependent on which part of the procedure is being performed, and this will generally change as the procedure progresses. Once the relevant segments are selected, (block 707), a transparency factor is adjusted, such that both the 3D volume rendered CT structures (in segments) and underlying live fluoroscopy images are conveniently visible, (block 709). The procedure is commenced with proper placement of the catheter (or balloon) block 711.

A more detailed workflow is explained further below with the aid of flow diagrams. As explained before, in the method and system of this disclosure, 3D (3-dimensional) volume rendered anatomical segments are prepared using a 3D volume rendering software. It will be clear to one in the art, that the 3D volume rendered digital structures can be from CT (computed tomography) or from MR (magnetic resonance) imaging. Both CT and MRI are highly detailed imaging modalities. For the purposes of this disclosure, either can be used, and anything explained with CT will apply equally to MRI imaging also, as the methodology is pretty much the same.

Utilizing a volume rendering software the CT or MRI segment files are stored. The storing media can be within the cardiac mapping system workstation or an external medium. It is noted that the data is stored in a way, such that different anatomical structures are stored in different corresponding digital files. The anatomical structures can be any anatomical structures of the body, which may be small or large. Some examples of anatomical structures without limitation are, left atrium (LA), pulmonary veins (PV), appendage, coronary sinus, right atrium, esophagus, and spine. One advantage of storing different anatomical structures in separate digital files is that they can be selectively turned ON and turned OFF. This is advantageous because during different parts of procedure, different structures are required or preferred. Further, any group of structures (or files) can be selectively turned OFF and any given structure (or files) can be selectively turned ON. This can be done in any combination.

Guide to Placement of Left Ventricular (LV) Lead for Cardiac Re-Synchronization Therapy The cardiac system of the current disclosure is also used for guiding a left ventricular (LV) lead placement for Cardiac Re-synchronization therapy.

One of the major hurdle in cardiac re-synchronization therapy (CRT) is the optimal placement of the Left Ventricular (LV) lead, and to pick the proper electrode for unipolar pacing or to pick the proper electrode pair for bipolar pacing out of the several pairs of electrodes (or single electrode) for optimal programming, to deliver cardiac resynchronization therapy (CRT). A key aspect of picking the optimal electrode pair is based on that the lead is positioned in the proper branch of the coronary sinus (CS) in the first place.

Figure 49:
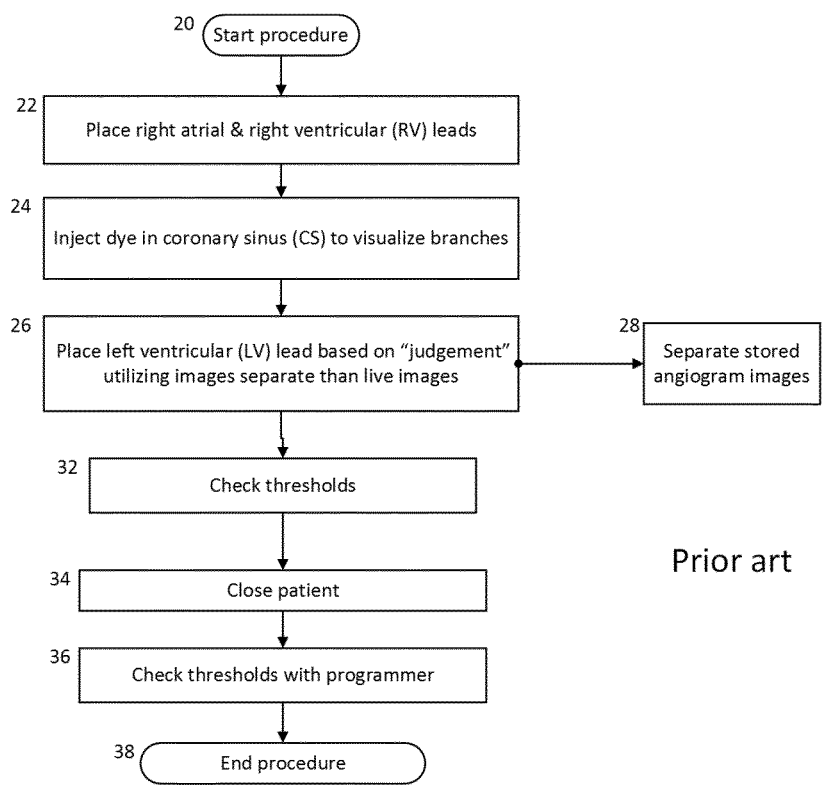
FIG. 49 is flow diagram showing "prior art" procedure for LV lead placement and for cardiac resynchronization therapy.
Figure 50:
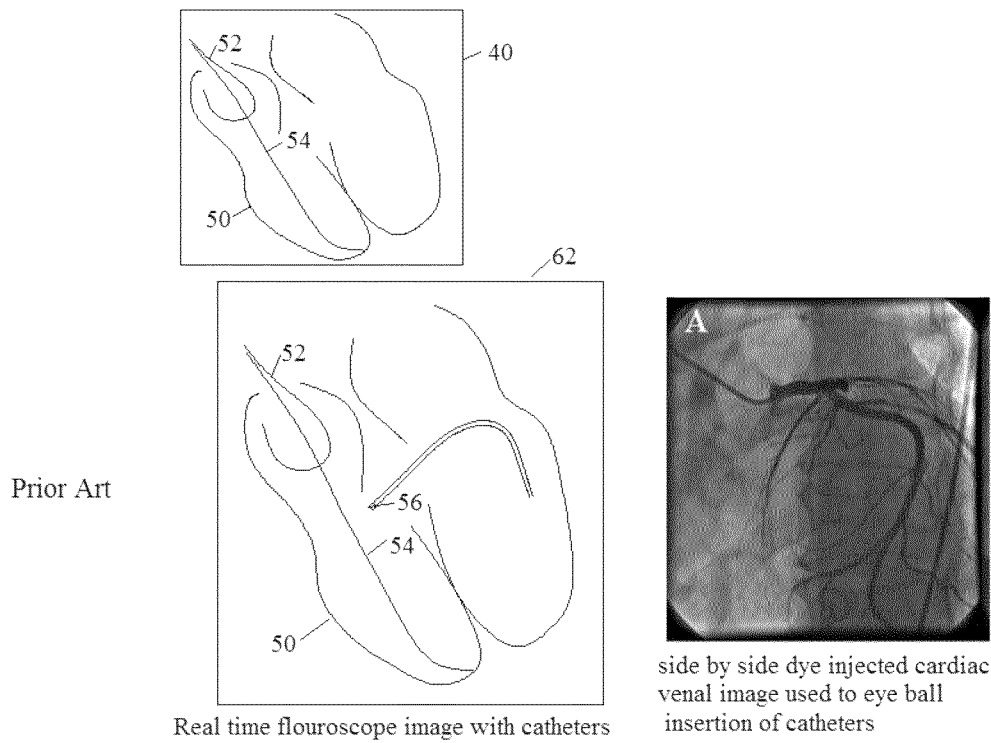
FIG. 50 depicts "prior art" road map technology for showing contrast medium injection in coronary sinus.

Prior art methods are described with FIGS. 49 and 50. Generally, as shown with the flow diagram in FIG. 49, right atrial and right ventricular leads are implanted first. Typically, to visualize the venous anatomy of the coronary sinus (CS) and its branches, contrast medium or dye is injected into the coronary sinus (CS). A video recording of the dye injection into the coronary sinus or angiogram is usually made utilizing fluoroscopy. Generally, with "road map" technology available from most fluoroscopy system manufacturers, a picture of the "lighted up" coronary sinus branches is displayed on the fluoroscopy system on a secondary fluoroscopy monitor which is next to the live fluoroscopy monitor. Shown as step 28 in the flow diagram. The physician then generally "guesses" on the branch which looks like the optimal place for implanting the left ventricular lead.

Figure 51:
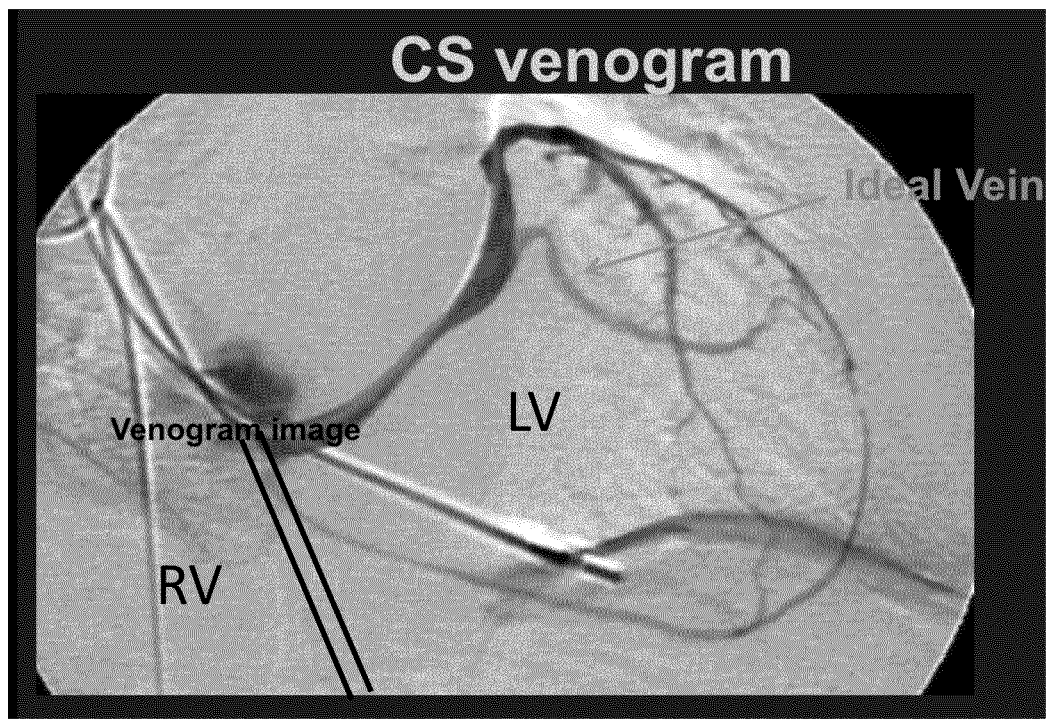
FIG. 51 is a picture showing contrast medium injected into the coronary sinus and branches.

FIG. 50 depicts an example of this, where live fluoroscopy is shown in the bottom left and recorded angiogram is shown on the bottom right of the figure. By visualizing the angiogram on a separate monitor and manipulating the lead with a different monitor, the physician can only guess on the optimal placement. FIG. 51 shows an example of a venogram (also called angiogram).

Since optimal placement of the left ventricular (LV) lead is very important for optimizing the CRT therapy and is currently challenging to find the optimal placement of the lead, there is a high level of interest in implanting the LV lead based on a more objective criteria. Some physicians have utilized cardiac mapping systems for this application, for optimizing the location of the LV leads. The current mapping systems have their own drawbacks for this application, since most mapping systems are non-fluoroscopic based systems typically based on electrical impedance and/or magnetic sensors. Further, these systems are complicated to set-up and add a lot of additional cost (of mapping) to the procedure.

It would be highly desirable to have a fluoroscopy based mapping system which is also structured to utilize and configured to help map the optimal placement of the left ventricular (LV) lead, thereby optimizing the CRT therapy. Further, such a system would not add cost to the CRT implantation procedure, as well as, be user friendly so that the hospital staff is not dependent on a mapping system company representative, as is frequently the case with mapping for cardiac ablation procedures.

Figure 52:
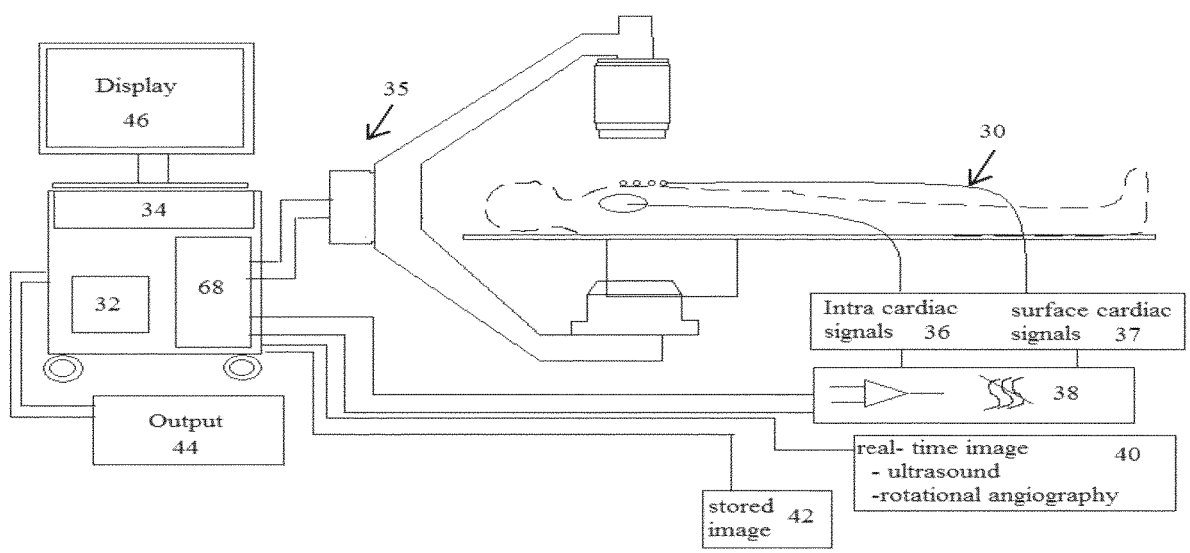
FIG. 52 depicts the cardiac system of the current disclosure and its relationship to other equipment in the implant room.

As shown in FIG. 52. A patient's image is generally visualized via fluoroscopy 35. The patient is also connected to surface ECG 30. In addition to the surface ECG signals, intracardiac signals are also obtained from the patient. Both the fluoroscopy image and electrical signals (surface and intracardiac) are brought into a Fluoroscopy based Cardiac Mapping System or computerized system. Other real time images 40 may also be brought into Fluoroscopy Mapping System or computerized system. Examples of other images may be ultrasound, rotational angiography just to name a few. Additionally, stored images such as CT or MRI may also be brought into the Fluoroscopy Mapping System. The mapping system then utilizes the existing medical image or images, and superimposes the electrical cardiac activity on the existing image or images. Generally, the mapping information is collected by placing the temporary wire, or temporary lead at various places in the heart, and various mapped points are stored in a table in the computer of the mapping system. Alternatively, this information can also be obtained from the implantable lead, which can be moved around for collecting the location and timing information. The vast information can then be organized by the computer of the mapping system.

The software in the mapping system computer is configured and programmed such that the vast amount of electrical signals information is superimposed on the existing image in a meaningful way. Generally, the information is also color coded for convenience, but other methodology may also be used for displaying the information in a meaningful way. Advantageously, in the method and system of this disclosure the geometry is already existing and does not have to be created. This also has the advantage that multiple layers of information can be superimposed in the image. This is described more fully later in the disclosure.

The signals acquisition and system setup is summarized in conjunction with FIG. 53. The acquisition of signals from a patient 50 into the mapping system 160 of this disclosure are shown in conjunction with FIG. 53. As shown, cables 108 from body surface electrodes, and cables 110 carrying intracardiac signals from the heart 52 are amplified, filtered 109 via A/D converter 111, and brought into the computer 7 of the mapping system 160. The computer 7 of the mapping system 160 also comprises algorithm(s)/program(s) which are configured for data analysis and processing which is used for guiding the ablation procedure with the mapping system 160. The signals from the computer 7 are displayed on a monitor shown in FIG. 53 as mapping system display 5.

Figure 54:
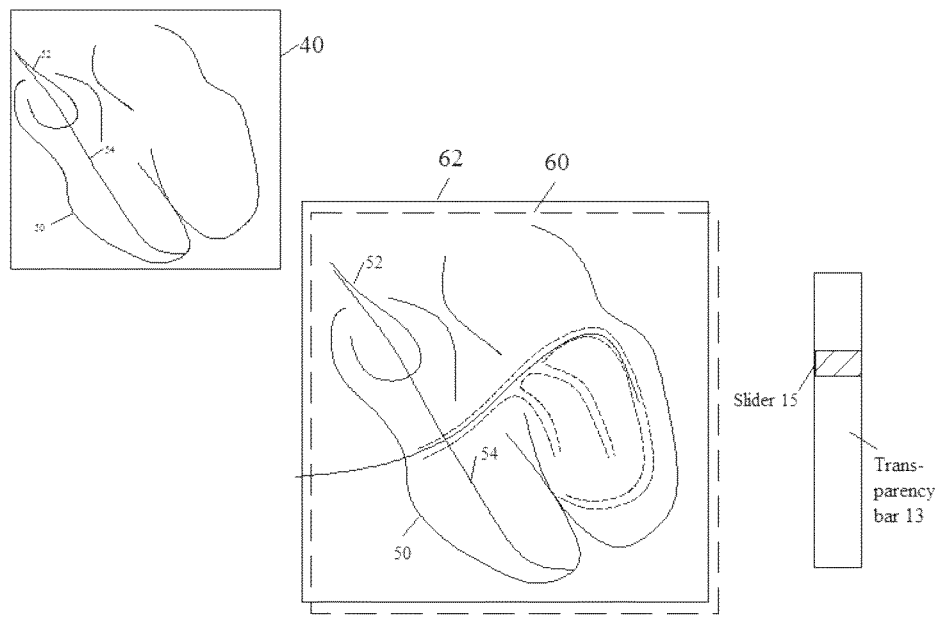
FIG. 54 depicts diagrammatically the overlaying of recorded fluoroscopy images and live fluoroscopy images, with means for adjusting transparency between the two fluoroscopy layers.

In the mapping system of the current disclosure, the software is configured and programmed such that the recorded fluoroscopy images with dye (contrast medium) injection, which are stored, can be overlaid with a live fluoroscopy layer. As shown with FIG. 54, a live fluoroscopy layer 60 is overlaid on top of a recorded angiogram image(s) 62. Once the two layers of fluoroscopy images are overlaid on top of each other, a slider 15 on transparency bar 13 can adjust the relative transparency between the two layers (live and recorded) of fluoroscopy. This has the advantage that a temporary wire or lead can be manipulated to various sites using the anatomy details that are provided by the recorded and stored angiogram.

Figure 55:
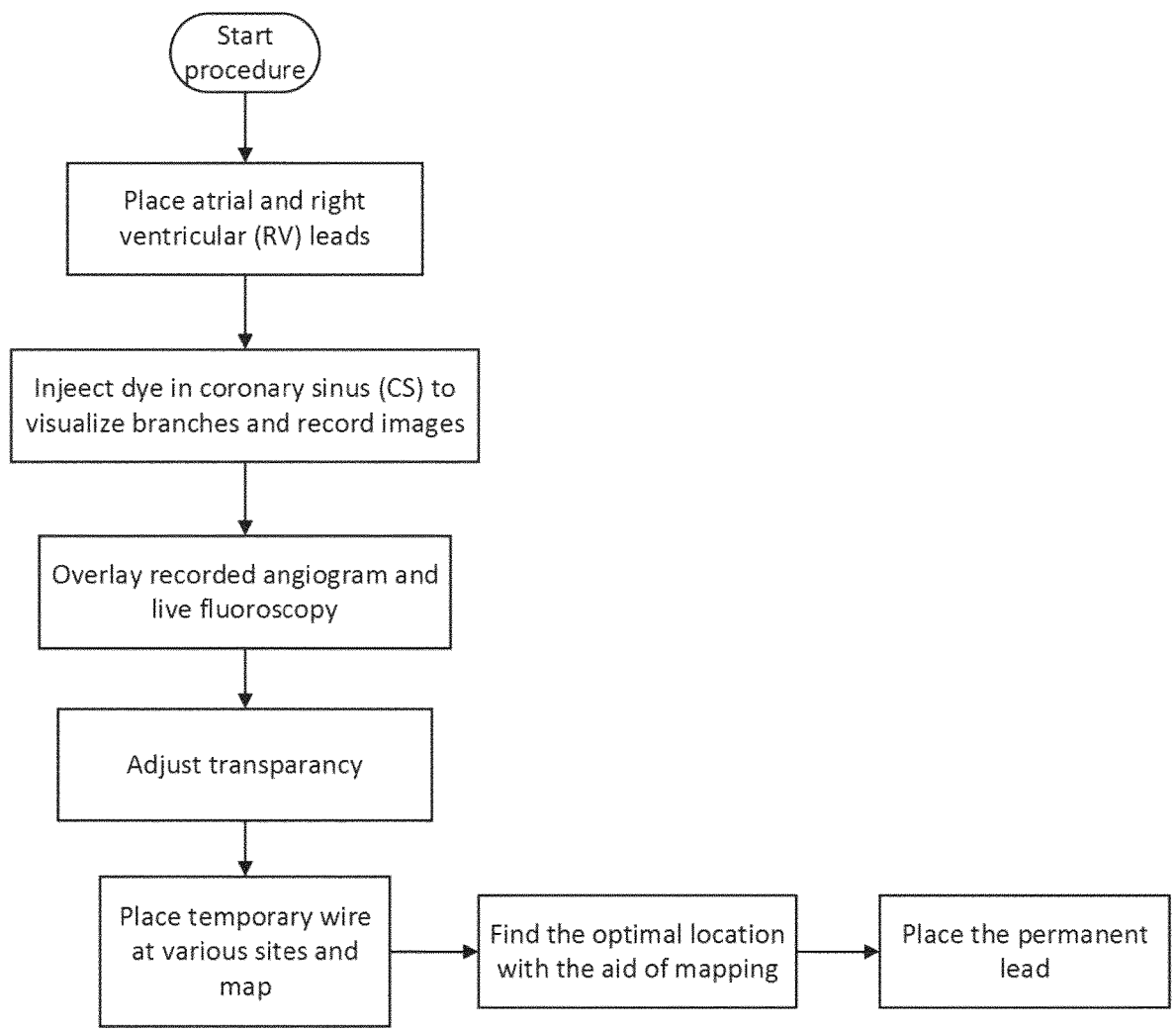
FIG. 55 is a simplified flow diagram of the workflow of the procedure.

The flow diagram shown in FIG. 55 details the steps and workflow. Right atrial and right ventricular leads are generally implanted first. The dye or contrast medium is injected into the coronary sinus. A short video is recorded of the angiogram in the mapping system workstation. The relevant image or segment is selected by the operator. The operator then overlays the live fluoroscopy on top of the recorded detailed image (of the angiogram), shown in. A transparency factor between the two recorded images is adjusted by the operator to a level where the temporary wire can be manipulated utilizing the live fluoroscopy layer while still being able to utilize the detailed anatomy from the angiogram. Using these tools, the physician places the lead at various places in different branches and at different levels within the branches, and the corresponding activation times relative to a reference electrical signal are measured.

Figure 56:
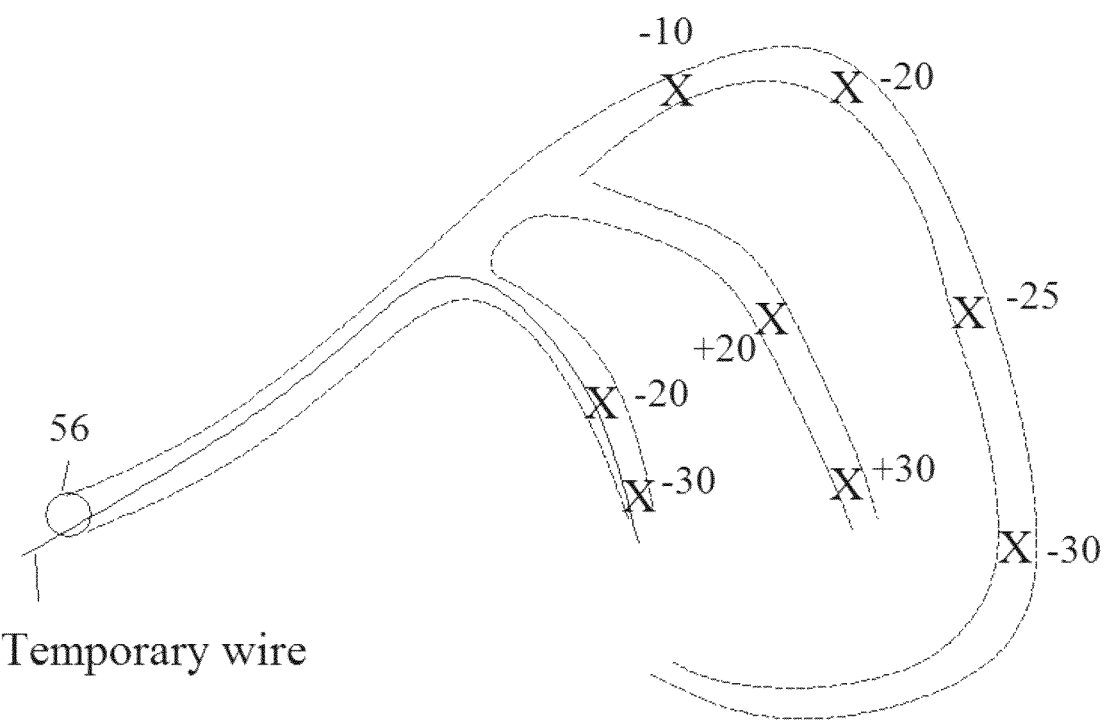
FIG. 56 shows the placement of the pacing lead in different branches of the coronary sinus.

This is also shown in FIG. 56. In FIG. 56, various selected sites and their corresponding local activation times (LAT)

are depicted. Utilizing the mapping system, such information will be displayed on the monitor utilizing a color interpolation algorithm for easy interpretation for the physician. Of the data collected from various sites, the physician is generally looking at the site with the latest activation. That will generally become the site of left ventricular pacing.

Figure 57:
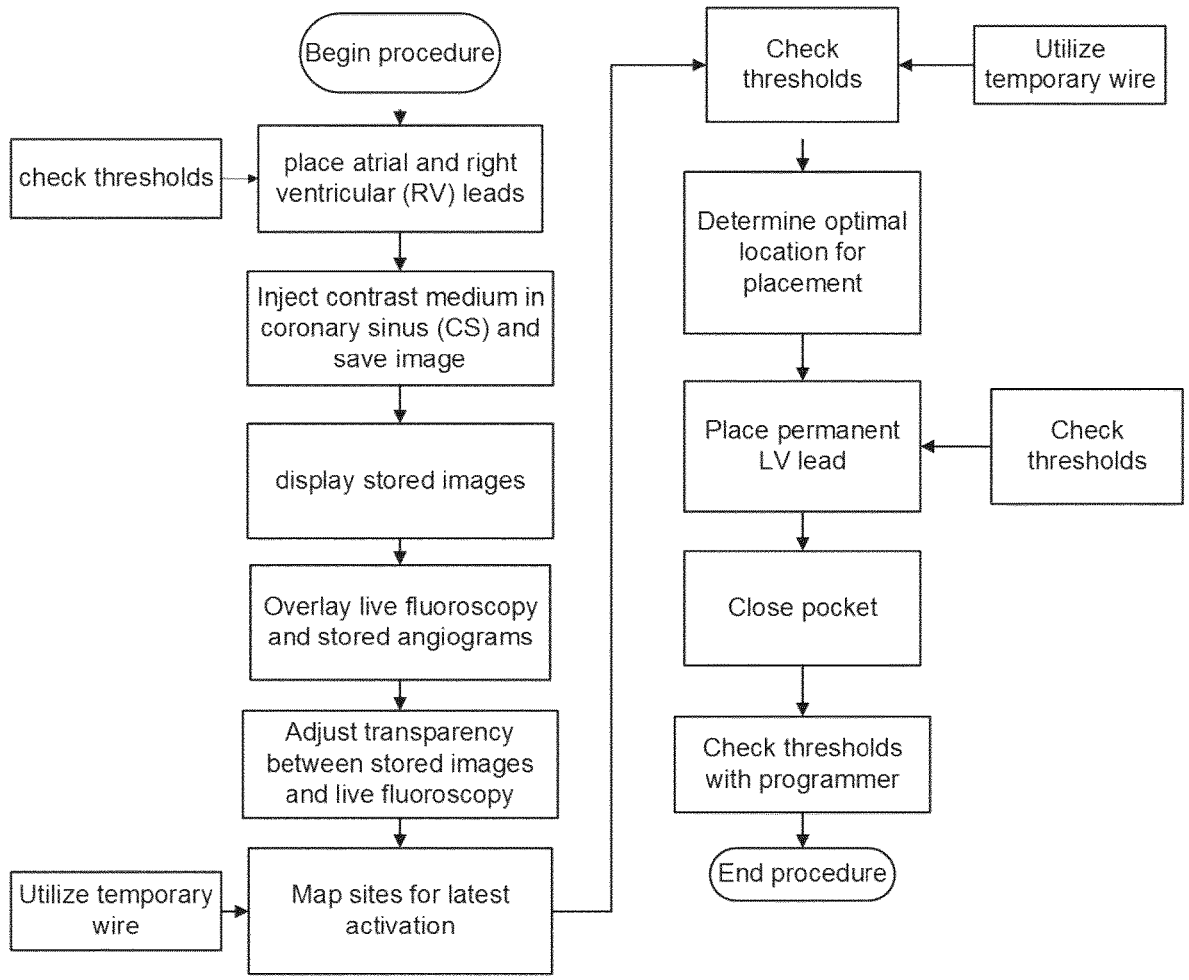
FIG. 57 is a flow diagram of the workflow from beginning to end of the procedure.

The flow diagram in FIG. 57 details the general workflow for the implant procedure. Atrial and ventricular leads are implanted in the normal fashion and the thresholds are checked. The physician generally injects dye or contrast medium into the coronary sinus (CS) and the images are recorded and stored. These recorded images are also brought into the mapping system computer and stored in the mapping system workstation. The appropriate recorded image(s) is/are selected by the operator and within the appropriate menu of the software, live fluoroscopy is overlaid on the recorded image(s) of the flow diagram. The transparency between the images is then adjusted by the operator. With the transparency adjusted such that live fluoroscopy and recorded detailed angiogram are both visible, and the physician is able to map several appropriate sites for activation times utilizing a temporary wire or a temporary lead specifically designed for this purpose. Alternatively, the physician can also perform the activation mapping utilizing the permanent lead that is going to be implanted. Once the appropriate position is determined by the physician, the permanent lead is implanted there, and the threshold is checked again with the permanent lead. Once the physician is satisfied with the placement of the leads, the pacemaker is connected to the lead, placed in the pocket. Before the procedure is finished, the thresholds are generally checked through the implanted device utilizing a programmer.

For the implementation of the above, a computerized system comprising a hardware, software, and capable of utilizing medical image(s) for guidance and/or navigation for a cardiac procedure and configured and programmed for overlaying two or more images on top of each other, wherein a transparency factor between the two or more images can be adjusted for visualization, such a system can be used and is within the scope of this disclosure. Such a computerized system is further capable of tabulating activation timings from the selected sites, which may be any number of sites. Typically 2-50 sites may be tabulated.

A fluoroscopy (and other medical images) based cardiac mapping system has been developed and is disclosed below. It will be clear to one of ordinary skill in the art that the exact functionality can be incorporated in a cardiac monitoring/recording system, or any computer based cardiac system whether or not it is considered a cardiac mapping system. Therefore, these terms may be used interchangeably in this disclosure.

Figure 58:
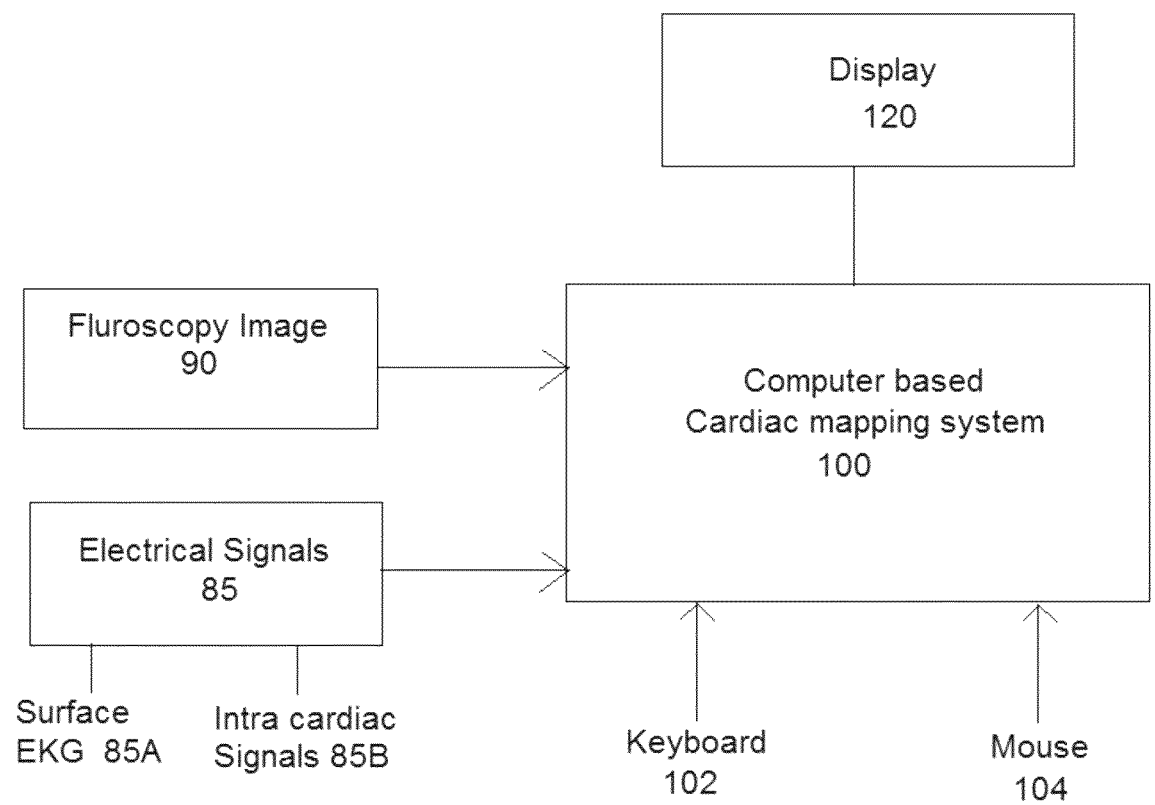
FIG. 58 depicts in a simplified block diagram form the connections of the computer system of this disclosure.

In the fluoroscopy based cardiac mapping system 100, fluoroscopy images 90 and electrical signals 85 are brought into a computer based cardiac mapping system 100. This is shown in conjunction with FIG. 8. It will be clear to one skilled in the art, that the electrical signals comprise both body surface EKG signals 85A, as well as, intra-cardiac signals 85B. Further, the intracardiac signals may comprise both unipolar signals and bipolar signals. Unipolar signals in the art refer to pacing with a pacing electrode vs a remote ground. Bipolar pacing in the art refer to pacing from an electrode pair that is relatively close to each other. As is also shown in FIG. 58, the cardiac mapping system is connected to a display 120. Typically keyboard 102 and mouse 104 are also connected to the mapping system 100.

In the method and system of this invention, fluoroscopy image(s) 90 and electrical signals 85 are brought into the mapping system. Using a keyboard and/or mouse, visual tags are placed on the various electrodes or electrode pairs for determining local activation time (LAT) relative to the QRS on a surface EKG.

Figure 59:
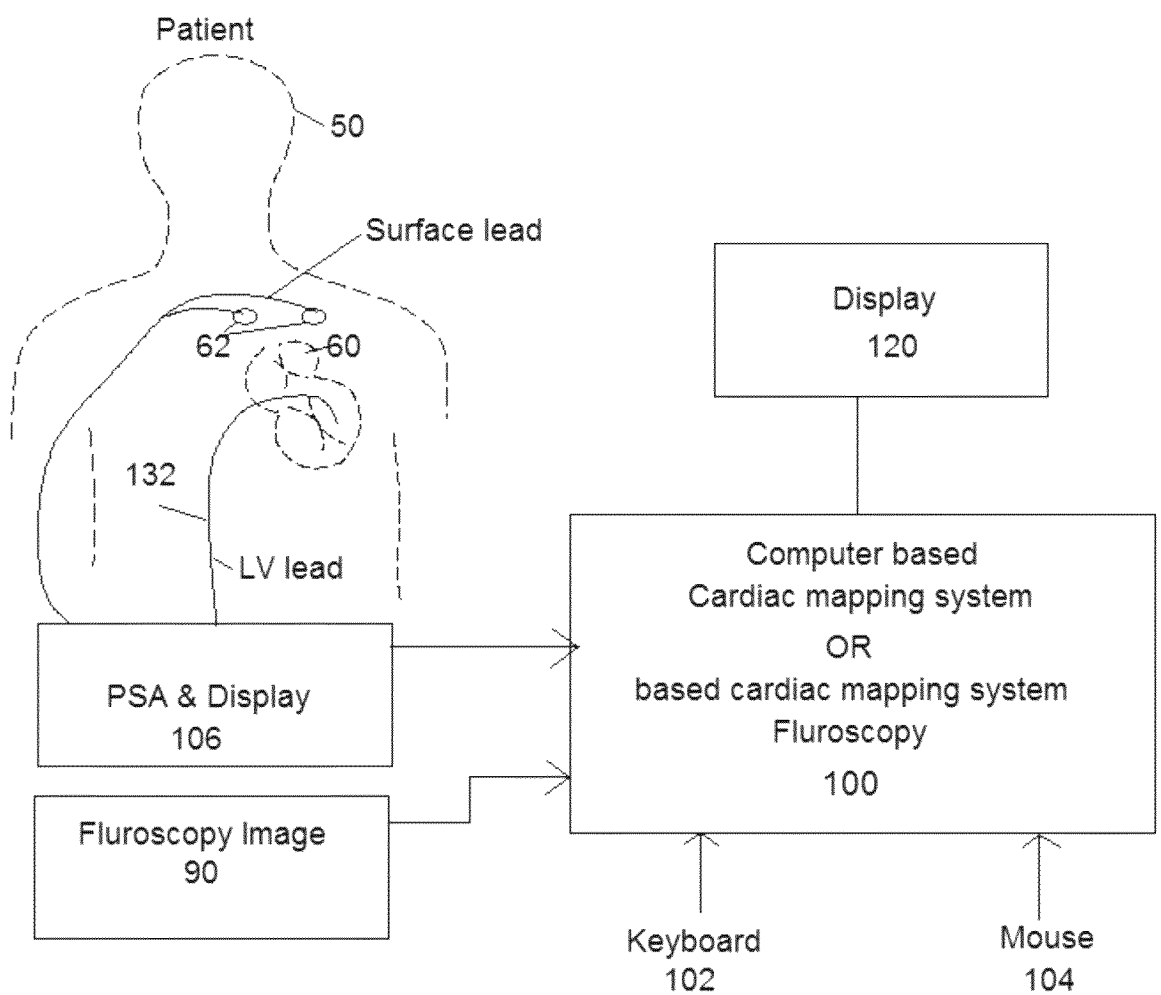
FIG. 59 is a simplified diagram showing the connection of the equipment to the patient.
Figure 60:
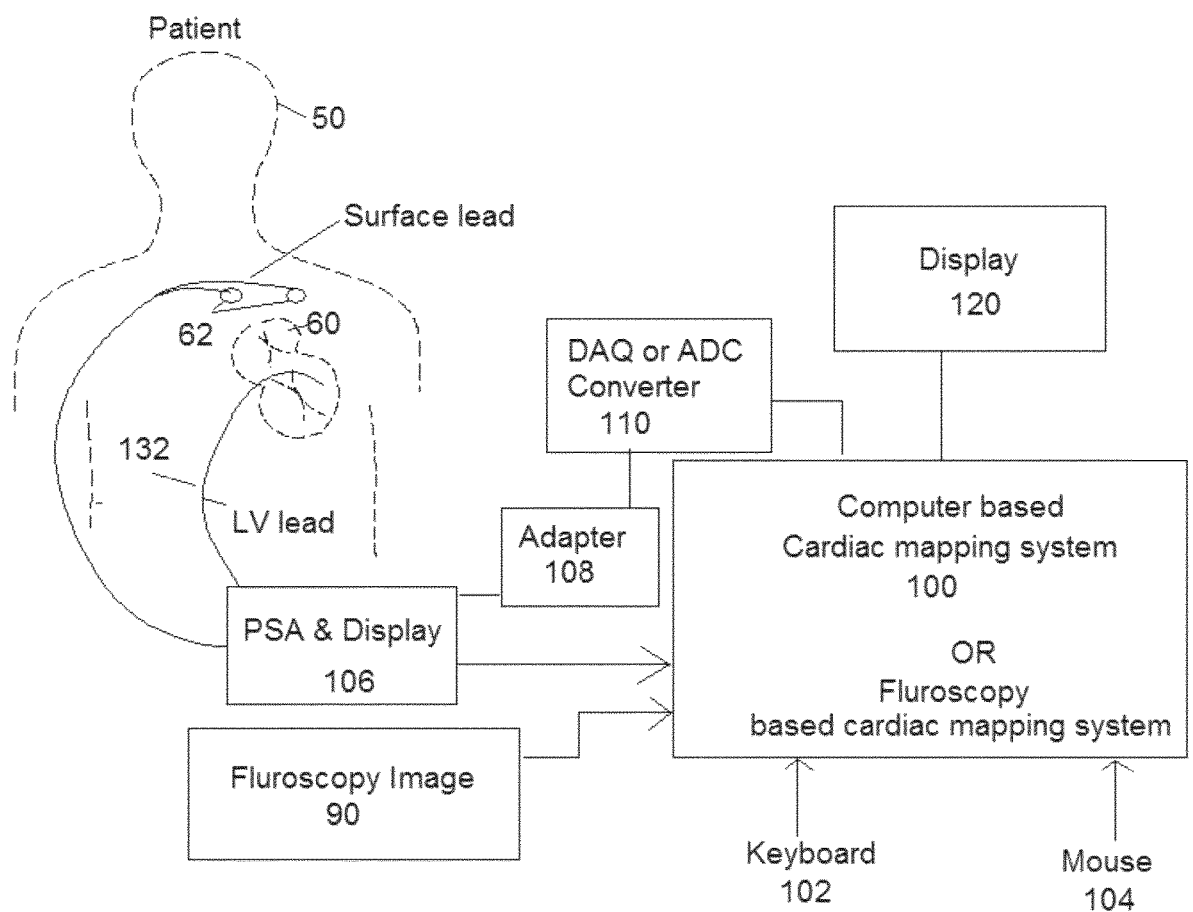
FIG. 60 is a simplified diagram showing the Cardiac Mapping System and its connection to the patient and other equipment.

As shown in FIG. 59, in one embodiment the body surface signals are brought into a pacing system analyzer (PSA) 106 via surface electrodes 62 and intracardiac signals are brought into the PSA 106 from an implantable LV lead 132 placed in the appropriate branch of the coronary venous structure. In this embodiment, the signals from the PSA 106 are brought into the cardiac mapping system 100 along with the fluoroscopy image(s) 90. This is shown in more detail in FIG. 60. As shown in FIG. 60, the signals are connected via an adaptor 108 to an analog-to-digital converter 110 which connects to the mapping system computer 100.

Figure 61:
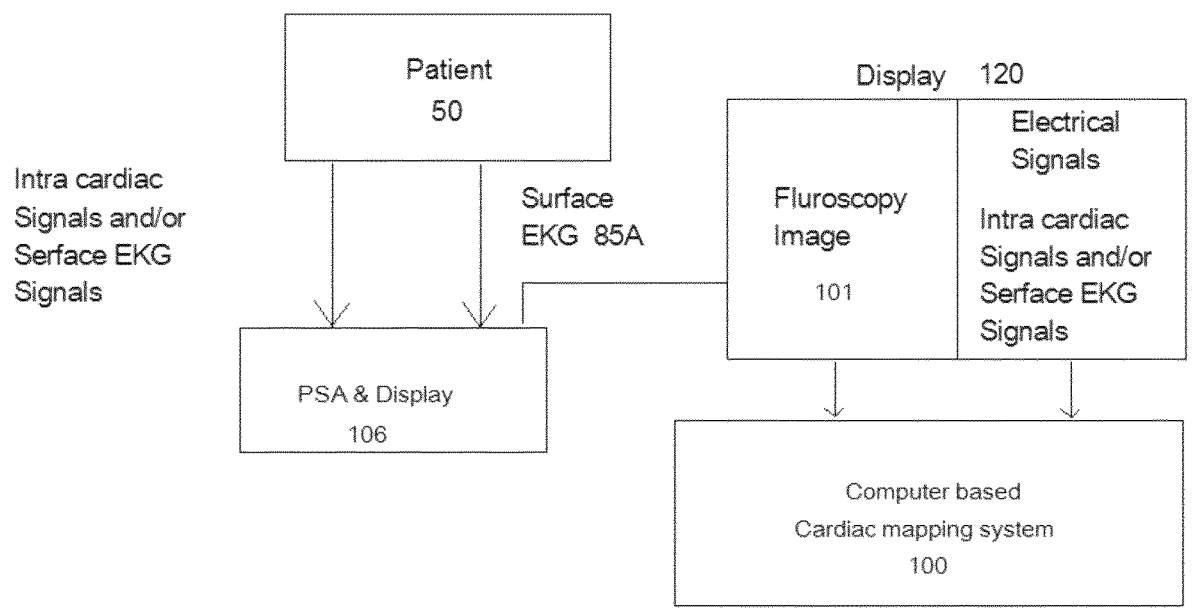
FIG. 61 is a simplified block diagram showing the interconnection of the patient to various equipment.
Figure 62:
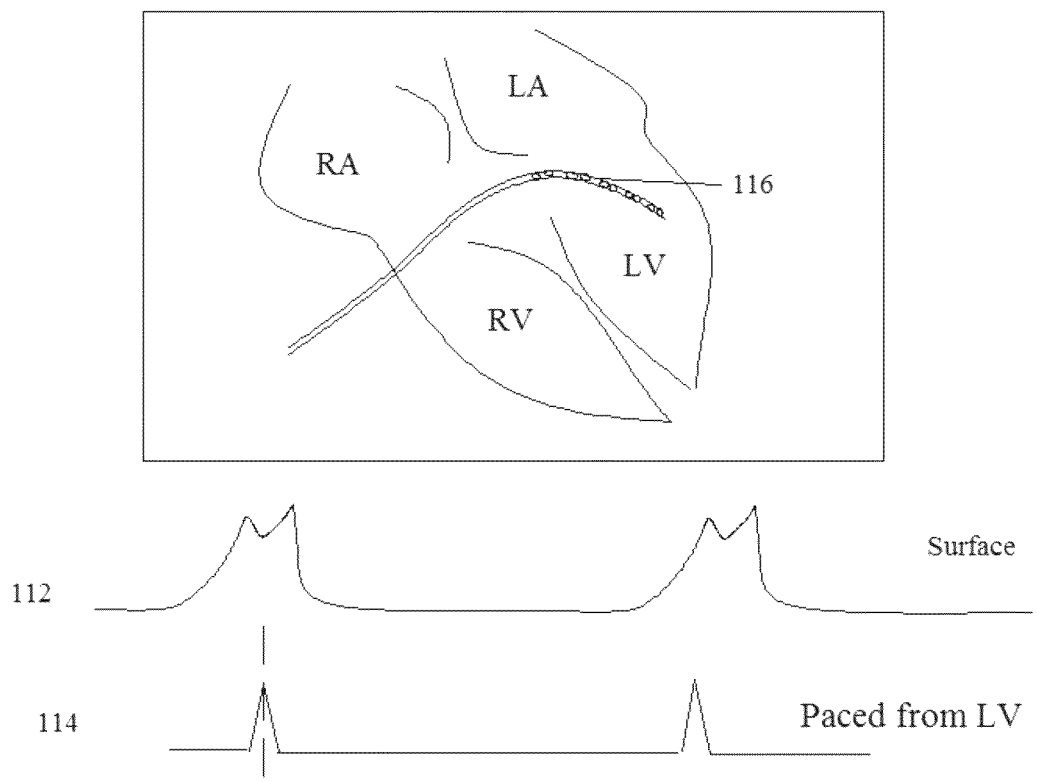
FIG. 62 is a diagram showing timing measurements from paced LV lead.

In an alternative embodiment, shown in FIG. 61, the signals from pacing system analyzer (PSA) 106 are brought into a monitor in the EP lab suite. Signals from the display monitor are then brought into the cardiac mapping system 100. There may be other ways to bring the signals in the cardiac mapping system 100. In any case, pacing is tried from different electrodes or electrode pairs and the relative electrical timing information is recorded. As shown in FIG. 62, a surface EKG lead QRS signal may be used as the reference signal which by definition is defined as time=0 (T=0). As shown in the figure, multiple channels of information may be displayed. The QRS signal from a surface lead is generally taken to be time zero (T=0), and paced signals from the LV lead are placed on the same time base and are compared relative to the fiducial point of the QRS of the surface.

This is also shown in more detail in FIG. 63. In one preferred embodiment, visual indicators are placed on the electrode pairs for bipolar pacing and/or individual electrodes for unipolar pacing configuration. The software in the mapping system is configured and programmed such that the visual indicators can be color coded for organization and displaying the relative activation timing information. In this embodiment, the visual indictors correspond to an electrode pair. As pacing is performed utilizing various combinations and permutations, a table is generated which lists the electrode pairs or individual electrodes for unipolar and the relative timing information corresponding to that electrode or electrode pair. The software is configured and programmed such that the various visual indicators are color coded based on a predetermined scheme. For example, in one embodiment as is frequently used in cardiac mapping the earliest activation may be defined as red, and the latest activation may be color coded as purple, and timings in between may be shown as the colors of the rainbow. Based on this color scheme, the purple or latest activation site would be of clinical interest as the desirable site to pace from, for programming and optimizing the CRT therapy and device programming. Of course, the physician choice for programming also takes into account the pacing threshold values and whether or not there is diaphragmatic pacing from that site.

In the method and system of this disclosure, at each site a vertical line may be drawn at a consistent fiducial point on the surface EKG. This point serves as the reference (REF) or T=0. Relative to this fiducial point, the timing of the paced signal is measured on the same time base. Before the point is accepted, the value of local activation time may be adjusted in the mapping system, to get a more accurate measurement. This is repeated for each electrode and/or each electrode pair. A Table is generated for activation time values vs each electrode location or electrode pair location.

Shown in conjunction with FIG. 64, the permutations and combinations of unipolar and bipolar configurations may be tried. In this example there are five bipolar pairs. An LV lead may have any number of bipolar pairs. Two, three, four and five pairs are coming to the market. Five pairs in FIG. 64 is by way of example only. LV leads with four pacing pairs are already on the market. Various other LV leads are being introduced into the market or are planned to be introduced in the market.

In this example, the ten electrodes on the LV lead provide the 5 pairs for pacing in the bipolar configuration, and ten additional electrodes for unipolar pacing configuration. Additionally, various other combinations are also possible, for example the implantable device may be configured to pace from electrode 1 vs electrode 3. Large number of permutations and combinations are possible.

Figure 65:
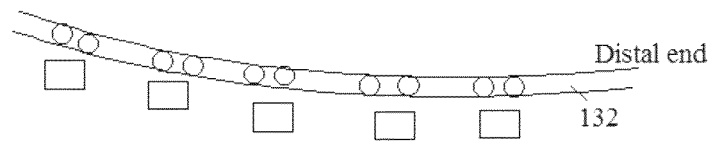
FIG. 65 is a diagram showing relative timing from different electrode pairs (bipolar) and different electrodes (unipolar).

As shown in conjunction with FIG. 65, in the method and system of this disclosure, LEDs or visual indicators may be placed on the fluoroscopic display of the heart and lead. As each electrode or electrode pair is tried, a visual indicator is placed utilizing a computer "mouse" in one embodiment. Additionally, a table is generated where each electrode (or electrode pair) is matched with the relative time, relative to a surface lead. As the table is populated with values which are obtained by testing the lead or pacing from the lead. The software in the mapping system is configured and programmed to display color coded information to the visual indicators.

Generally, the physician is looking for the latest relative time, i.e. where the activation is the latest. The physician is also concerned with level of diaphragmatic stimulation and threshold numbers. This way the mapping system provides useful information which is color coded. In one embodiment.

It is known in the art that the LV lead can be paced in either the Unipolar or the Bipolar configuration. It is also generally known in the art, that an LV lead may have several electrode pairs. Based on the number of electrode there will generally be large number of permutations and combinations of unipolar and bipolar configuration pairs. For example, if an LV lead has 10 electrodes, then there will be at least 5 bipolar pairs plus additional at least 10 unipolar configuration. This is also shown in FIG. 64.

As shown in FIG. 64, an LV lead having 10 electrodes will have at least 5 bipolar pairs for pacing and 10 electrodes for unipolar pacing configurations. Plus there may be other bipolar pacing configurations.

In the method and system of this disclosure, visual tags are overlaid on the fluoroscopy image of the LV venous structure LV lead with multiple electrode. As pacing from different electrodes and electrode pairs are tried, a table is constructed in the mapping system computer. At each configuration of electrode or electrode pair a visual indicator is placed. In one embodiment the visual indicator may be an LED (light emitting diode). In another embodiment the visual indicator may be other than or LED. As pacing from each electrode or electrode pair is tried, a visual indicator is placed on that electrode for unipolar configuration or on the electrode pair for bipolar configuration. As pacing is tried, a table is constructed in the mapping system computer. An example of this is shown in FIG. 65.

Shown in FIG. 66 is an example of table that is generated as mapping is tried from various sites using a temporary wire or lead.

Figure 67:
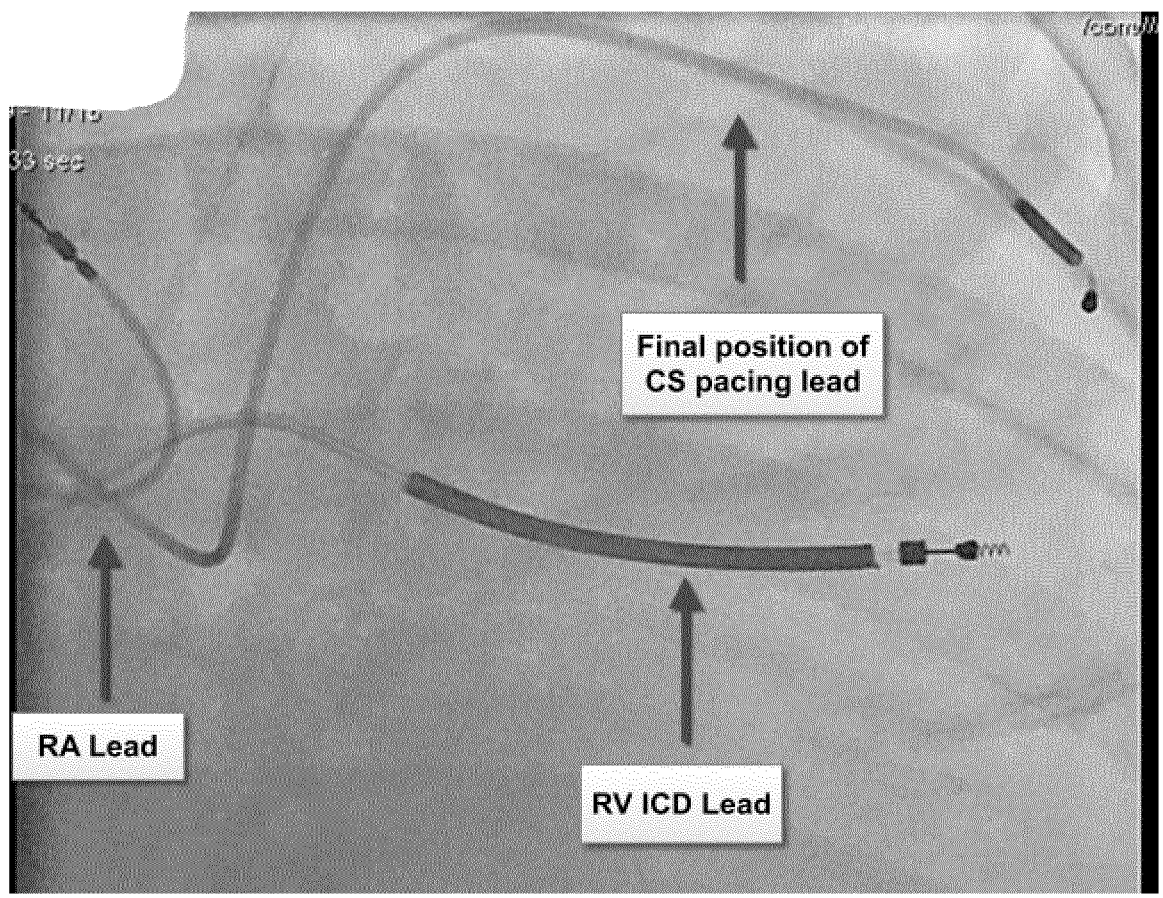
FIG. 67 is a picture showing the final placement of a right ventricular (RV) and left ventricular (LV) lead.

FIG. 67 shows an example of the left ventricular as it is finally placed in the optional location for providing therapy.

While this disclosure has been described with reference to preferred embodiments, it will be understood by those skilled in the art that various changes may be made without departing from the scope of the invention. In addition, many modifications may be made to adapt a particular situation or material to the teaching of the invention with departing from the essential scope thereof. Therefore, it is intended that the disclosure not be limited to the particular embodiments disclosed for carrying out this invention, but that the invention will include all embodiments falling within the scope of the appended claims.

The invention claimed is:

1. A method of guidance and/or navigation for lead placement for cardiac re-synchronization therapy (CRT), comprising the steps of:
   providing an implantable lead adopted for implanting in a coronary sinus and/or its branch(s) for pacing the left ventricle, and comprising at least one electrode;
   overlaying a live fluoroscopy image(s) and recorded high resolution angiogram image(s), and adjusting a transparency between two images to visualize the position of said implantable lead in the said coronary sinus and/or its branch(s) by utilizing a computer based system capable of acquiring a patient's electrical signals and medical image(s);
   placing a visual tag on a selected site in the said coronary sinus and/or its branch(s) by utilizing the position of said implantable lead;
   measuring and recording the activation timing information relative to a reference time for said site;
   placing at least a second tag on at least a second selected site in the said coronary sinus and/or its branch(s) and measuring and recording the activation timing information relative to a reference point of said second site;
   tabulating said activation timing information relative to a reference timing of said sites; and
   displaying said activation timing information relative to a reference timing of said sites on a screen.

2. The method of claim 1 wherein, said selected sites can range from 2-50.

3. The method of claim 1 wherein, said implantable lead can be a temporary lead used for collecting selecting said sites.

4. The method of claim 1 wherein, said computer based system can be a cardiac mapping system or a monitoring system or a recording system.

5. The method of claim 1 wherein, activation timing is based on comparing timing to a fixed electrical signal reference.

6. A method of lead placement for cardiac resynchronization therapy (CRT), comprising the steps of:
   placing a implantable lead adopted for implanting in a coronary sinus and/or its branch(s) for pacing the left ventricle, and comprising at least one electrode;
   overlaying the live fluoroscopy image and recorded angiogram by adjusting transparency to visualize the position of said lead in the said coronary sinus and/or its branch(s) by utilizing a computer based system capable of acquiring a patient's electrical signals and medical image(s);
   selecting at least two sites in said coronary sinus and/or its branch(s) and placing visual tags on said selected sites;
   recording relative activation timing information relative to a reference timing for said sites;
   tabulating said activation timing information relative to a reference timing for said sites;

displaying said activation timing information relative to a reference timing for said sites on a screen; and selecting said site with that has the latest activation timing information for lead placement.

7. The method of claim 6 wherein, said implantable lead adopted for implanting in said coronary sinus or its branch (s) for pacing the left ventricle can be a unipolar or bipolar lead.

8. The method of claim 6 wherein, said selected sites can range from 2-50.

9. The method of claim 6 wherein, said implantable lead can be a temporary lead used for collecting selecting said sites.

10. The method of claim 6 wherein, wherein said computer system is capable of tabulating variable data values.

11. The method of claim 6 wherein, said computer based system can furthermore be a cardiac mapping system or a monitoring system or a recording system.

12. The method of claim 6 wherein, activation timing is based on comparing timing to a fixed electrical signal reference.

13. The method of claim 6 wherein, said images comprises at least one from a group comprising live fluoroscopy, stored fluoroscopy images, stored fluoroscopy video, recorded high resolution fluoroscopy with contrast medium (dye) injection.

14. A computer based system for guiding and/or navigating lead placement for cardiac resynchronization therapy (CRT) comprises:

an implantable lead adopted for implanting in said coronary sinus or its branch(s) for pacing the left ventricle, and comprising at least one electrode;

a computer based cardiac system comprising a software, a hardware, and capable of utilizing medical image(s) for guidance and/or navigation for a cardiac procedure and configured and programmed for overlaying two or more image(s) on top of each other, wherein a transparency factor between said two or more images can be adjusted;

an interface electronics connected to said computer based cardiac system for acquiring a patient's electrical signals and medical image(s) wherein said medical images comprises at least one from a group comprising live fluoroscopy, stored fluoroscopy images, stored fluoroscopy video, recorded high resolution fluoroscopy with contrast medium (dye) injection or recorded angiogram image(s); and said software is programmed and configured for tabulating activation timing information of various selected sites in the coronary sinus and/or its branch(s).

15. The system of claim 14 wherein, said implantable lead can be a temporary lead used for collecting selecting said sites.

16. The system of claim 14 wherein, said computer based system is further a cardiac mapping system used for navigation in atrial fibrillation balloon based catheter ablation procedures.

17. The system of claim 14 wherein, said software is capable of tabulating said activation timing information of various selected sites ranging from 2-50 in said coronary sinus and/or its branches.

18. The system of claim 14 wherein, said activation timing is based on comparing timing to a fixed electrical signal reference.

19. The system of claim 14 wherein, said implantable lead is a unipolar or bipolar lead.

20. The system of claim 14 wherein, said transparency factor between said two or more images can be adjusted such that between two layers of said image(s) at one end of the range only the bottom image(s) is visible, or at the opposite end of the range only the top image(s) is visible, or all different levels in-between the two ends where both the top and bottom image(s) are visible.

\* \* \* \* \*